US009839720B2

(12) United States Patent
Gan et al.

(10) Patent No.: US 9,839,720 B2
(45) Date of Patent: *Dec. 12, 2017

(54) COATING AND COATING METHOD

(71) Applicant: Smith & Nephew, Inc., Memphis, TN (US)

(72) Inventors: Lu Gan, Memphis, TN (US); Marcus L. Scott, Memphis, TN (US); Shilesh C. Jani, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,510

(22) Filed: Sep. 2, 2014

(65) Prior Publication Data

US 2015/0056264 A1 Feb. 26, 2015

Related U.S. Application Data

(63) Continuation of application No. 12/919,986, filed as application No. PCT/US2009/035467 on Feb. 27, 2009, now Pat. No. 8,821,911.

(60) Provisional application No. 61/032,621, filed on Feb. 29, 2008, provisional application No. 61/051,783, filed on May 9, 2008.

(51) Int. Cl.
| | | |
|---|---|---|
| *A61K 33/00* | (2006.01) | |
| *A61K 33/38* | (2006.01) | |
| *A61K 33/24* | (2006.01) | |
| *C23C 4/06* | (2016.01) | |
| *A61L 27/30* | (2006.01) | |
| *A61L 27/32* | (2006.01) | |
| *A61L 27/54* | (2006.01) | |

(52) U.S. Cl.
CPC .............. *A61L 27/30* (2013.01); *A61L 27/32* (2013.01); *A61L 27/54* (2013.01); *C23C 4/06* (2013.01); *A61L 2300/104* (2013.01); *A61L 2300/112* (2013.01); *A61L 2300/404* (2013.01); *A61L 2300/412* (2013.01); *A61L 2300/45* (2013.01); *A61L 2300/606* (2013.01); *A61L 2300/622* (2013.01); *A61L 2420/06* (2013.01); *A61L 2430/02* (2013.01)

(58) Field of Classification Search
CPC ............... C23C 4/06; A61L 2300/606; A61L 2300/622; A61L 2420/06; A61L 2430/02; A61L 27/30; A61L 37/32; A61L 27/54; A61L 2300/104; A61L 2300/112; A61L 2300/404; A61L 2300/412; A61L 2300/45

See application file for complete search history.

(56) References Cited

U.S. PATENT DOCUMENTS

| | | | |
|---|---|---|---|
| 5,009,898 A | 4/1991 | Sakuma et al. | |
| 5,151,122 A | 9/1992 | Atsumi et al. | |
| 5,266,534 A | 11/1993 | Atsumi et al. | |
| 5,268,174 A | 12/1993 | Sakuma et al. | |
| 5,348,577 A | 9/1994 | Atsumi et al. | |
| 6,113,993 A * | 9/2000 | Gao | C23C 14/06 427/2.27 |
| 6,129,928 A | 10/2000 | Sarangapani et al. | |
| 6,344,061 B1 | 2/2002 | Leitao et al. | |
| 6,419,708 B1 | 7/2002 | Hall et al. | |
| 6,482,444 B1 * | 11/2002 | Bellantone | A61K 9/70 424/618 |
| 6,582,715 B1 | 6/2003 | Barry et al. | |
| 6,719,897 B1 | 4/2004 | Maltin | |
| 6,719,987 B2 | 4/2004 | Burrell et al. | |
| 8,821,911 B2 * | 9/2014 | Gan | A61L 27/32 424/423 |
| 9,011,965 B2 * | 4/2015 | Gan | A61L 27/30 427/2.26 |
| 2001/0024662 A1 * | 9/2001 | Yang | A61L 24/02 424/489 |
| 2002/0018798 A1 | 2/2002 | Sewing et al. | |
| 2003/0165556 A1 | 9/2003 | Bechert et al. | |
| 2004/0074568 A1 | 4/2004 | Jennissen | |
| 2004/0153165 A1 | 8/2004 | Li et al. | |
| 2005/0221259 A1 | 10/2005 | Anderson | |
| 2006/0161256 A1 | 7/2006 | Ziegler et al. | |
| 2006/0198903 A1 | 9/2006 | Storey et al. | |
| 2006/0286140 A1 | 12/2006 | Wickstrom et al. | |
| 2007/0287129 A1 | 12/2007 | Ihde | |
| 2007/0298377 A1 | 12/2007 | Kenealy et al. | |
| 2009/0280156 A1 | 11/2009 | Hotokebuchi et al. | |
| 2011/0008407 A1 | 1/2011 | Gan et al. | |
| 2011/0014258 A1 | 1/2011 | Gan et al. | |

FOREIGN PATENT DOCUMENTS

| | | |
|---|---|---|
| EP | 1 764 119 A1 | 3/2007 |
| JP | 2000143219 A | 5/2000 |
| JP | 2003208807 A | 7/2003 |

(Continued)

OTHER PUBLICATIONS

Notice of Reexamination, Chinese Patent Office, Chinese Patent Application No. 200980115899.9, May 21, 2015, 15 pages.

(Continued)

*Primary Examiner* — Abigail Vanhorn

(74) *Attorney, Agent, or Firm* — Taft Stettinius & Hollister LLP

(57) ABSTRACT

The present invention discloses a coating for a medical implant, wherein at least a part of said coating contains an osseointegration agent and the same and/or a different part of the coating contains an antimicrobial metal agent.

19 Claims, 32 Drawing Sheets

(56) References Cited

FOREIGN PATENT DOCUMENTS

| JP | 2003218765 A | 7/2003 |
|---|---|---|
| JP | 2005132659 A | 5/2005 |
| JP | 2005-525165 A | 8/2005 |
| JP | 2005270945 A | 10/2005 |
| JP | 20061708 A | 1/2006 |
| JP | 20072505 A | 1/2007 |
| JP | 200873098 A | 4/2008 |
| WO | 00/76486 A1 | 12/2000 |
| WO | 03/094774 A1 | 11/2003 |
| WO | 2007/022211 A2 | 2/2007 |
| WO | 2007022211 A2 | 2/2007 |
| WO | 2007/048812 A1 | 3/2007 |
| WO | 2007/048817 A1 | 5/2007 |
| WO | 2007/085852 A3 | 8/2007 |
| WO | 2009/111300 A3 | 9/2009 |
| WO | 2009111307 A2 | 9/2009 |

OTHER PUBLICATIONS

Roger J. Narayan et al., "The Use of Functionality Gradient Materials in Medicine", JOM, vol. 58, No. 7, Jul. 2006, pp. 52-56.
Communication pursuant to Article 94(3) EPC, European Patent Office, European Patent Application No. 09717323.1, Dec. 6, 2013, 6 pages.
First European Office Action, European Patent Office, European Patent Application No. 09717323.1, Mar. 22, 2013, 6 pages.
First Office Action, Chinese Patent Office, Chinese Patent Application No. 200980114900.8, Jan. 29, 2013, 19 pages.
First Office Action, Japanese Patent Office, Japanese Patent Application No. 2010-548902, Aug. 13, 2013, 8 pages.
Giuseppe Pezzotti et al., "Study of the Toughening Mechanisms in Bone and Biomimetic Hydroxyapatite Materials Using Raman Microprobe Spectroscopy," Journal of Biomedical Materials Research Part A, vol. 65A, Issue 2, 2003, pp. 229-236 (8 pages).
International Search Report issued in PCT/US2009/035467, mailed on Oct. 13, 2009, 3 pages.
N. Rameshbabu et al., "Antibacterial Nanosized Silver Substituted Hydroxyapatite: Synthesis and Characterization," 2006, Wiley Periodicals, Inc., pp. 581-591 (11 pages).
Patent Examination Report No. 1, Austrailian Patent Office, Australian Patent Application No. 2009222172, dated Sep. 23, 2013, 5 pages.
Q.L. Feng et al., "Antibacterial Effects of Ag—HPp Thin Film on Alumina Substrates," Thin Solid Films 335, 1998, pp. 214-219 (6 pages).
Second Office Action, Chinese Patent Office, Chinese Patent Application No. 200980115900.8, Aug. 22, 2013, 15 pages.
Supplementary European Search Report, European Patent Office, European Patent Application No. 09717323.1, Mar. 15, 2013, 2 pages.
T. N. Kim et al., "Antimicrobial Effects of Metal Ions (ag+, Cu2+, Zn2+) in Hydroxyapatite," Journal of Materials Science: Materials in Medicine, Chapman & Hall, Issue vol. 9 No. 3, Mar. 1998, pp. 129-134 (6 pages).
W. Chen et al., "Antibacterial and Osteogenic Properties of Silver-Containing Hydroxyapatite Coatings Produced Using a Sol Gel Process," J Biomed Mater Res A., Sep. 15, 2007, 82(4): pp. 899-906 (8 pages).
W. Chen et al., "In Vitro Anti-bacterial and Biological Properties of Magnetron Co-Sputtered Silver-Containing Hydroxyapatite Coating," Biomaterials, vol. 27, Issue 32, Nov. 2006, pp. 5512-5517 (6 pages).
Y. Ando et al., "In Vitro Antibacterial Properties of Thermal Sprayed Silver-Containing Hydroxyapatite Coating Against Methicillin-Resistant Staphylococcus Aureus," Trans 54th Annual Mtg of the Orthopaedic Research Society, Japan (1 page).
X. Zhang et al., "Toughening of Calcium Hydroxyapatite with Silver Particles," Journal of Materials Science, Publisher Springer Netherlands, Issue vol. 32, No. 1, Jan. 1997, pp. 235-243 (9 pages).
T. K. Chaki et al., "Densification and Strenghtening of Silver-Reinforced Hydroxyapatite-Matrix Composite Prepared by Sintering," Journal of Materials Science: Materials in Medicine, Issue vol. 5, No. 8, Aug. 1994, pp. 533-542 (10 pages).
M. Shirkhanzadeh et al., "Bioactive Delivery Systems for the Slow Release of Antibiotics: Incorporation of Ag+ Ions into Micro-Porous Hydroxyapatite Coatings," Materials Letters, vol. 24, Issues 1-3, Jun. 1995, pp. 7-12 (6 pages).
Q. L. Feng et al., "Ag-Substituted Hydroxyapatite Coatings with Both Antimicrobial Effects and Biocompatibility," Journal of Materials Science Letters, Publisher Springer Netherlands, Issue vol. 18, No. 7, Apr. 1999, pp. 559-561 (3 pages).
First Canadian Office Action, Canadian Patent Office, Canadian Patent Application No. 2,761,589, Mar. 16, 2015, 6 pages.
European Office Action; European Patent Office; European Patent Application No. 09717323.1; Feb. 10, 2016; 6 pages.
Japanese Office Action; Japanese Patent Office; Japanese Patent Application No. 2015-022429; Jan. 25, 2016; 8 pages.
Canadian Office Action; Canadian Intellectual Property Office; Canadian Patent Application No. 2716589; Nov. 18, 2015; 3 pages.
Notice of Reexamination; Chinese Patent Office; Chinese Patent Application No. 200980115900.8; Sep. 9, 2015; 13 pages.
Indian Examination Report; Government of India Patent Office; Indian Patent Application No. 5959/DELNP/2010; Feb. 4, 2016; 2 pages.
Chinese Reexamination Decision; Chinese Patent Office (State Intellectual Property Office, P.R. China); Chinese Patent Application No. 200980115900.8; Mar. 4, 2016; 20 pages.
Japanese Notice of Reasons for Revocation; Japanese Patent Office; Japanese Patent No. 5788179; Jun. 9, 2016; 25 pages.
Badrour et al., Synthesis and Physical and Chemical Characterization of Ca10-xAgx(PO4)6(OH)2-x end of proof x Apatites, Ann. Chem. Sci. Mat, 1998, 4 pages, vol. 23, El Jadida, Morocco.
Ueda et al., Adhesion of Hydroxyapatite Layer Prepared by Thermal Plasma Spraying to Titanium or Titanium (IV) Oxide Substrate, Journal of the Ceramic Society of Japan, 2000, 4 pages, vol. 108 - issue 9.
Shi et al., Preparation and Effectiveness of Antibacterial Hydroxyapatite Powder Containing Silver, Key Engineering Materials, 2005, 4 pages, vol. 280-283, copyright 2005 Trans Tech Publications, Switzerland.
Chung et al., Anti-Microbial Hydroxyapatite Particles Synthesized by a Sol-Gel Route, Journal of Sol-Gel Science and Technology 33, 2005, 11 pages, copyright 2005 Springer Science + Business Media, Inc.
N. Rameshbabu et al., Antibacterial nanosized silver substituted hydroxyapatite: Synthesis and characterization, Journal of Biomedical Materials Research Part A, Oct. 9, 2006, 11 pages, Copyright 2006 Wiley Periodicals, Inc.
Xue et al., Preparation and cell-materials interactions of plasma sprayed strontium-containing hydroxyapatite coating, Surface and Coatings Technology, Jan. 15, 2007, 1 page, vol. 201—issue 8, copyright 2006 Elsevier B.V.
Zheng et al., Study on Silver-Containing Ha Coatings Prepared by Vacuum Plasma Spraying, Materials Science Form, 2007, 4 pages, vols. 544-545, copyright 2007 Trans Tech Publications, Switzerland.
Chen et al., Anti-bacterial and cytotoxic properties of plasma sprayed silver-containing Ha coatings, J. Mater. Sci. Mater. Med., Jul. 19, 2008, 7 pages, vol. 19, copyright 2008 Springer Science—Business Media, LLC.
Roy et al., Mechanical, in Vitro Antimicrobial and Biological Properties of Plasma Sprayed Silver-Doped Hydroxyapatite Coating, ACS Appl. Mater. Interfaces, Feb. 28, 2012, 11 pages, vol. 4—issue 3, US National Library of Medicine National Institutes of Health.
U.S. Appl. No. 61/032,621, filed Feb. 29, 2008, 9 pages.
U.S. Appl. No. 61/051,783, filed May 9, 2008, 10 pages.
Australian Patent Examination Report No. 1; Australian Patent Office; Australian Patent Application No. 2015227489; Nov. 11, 2016; 4 pages.

(56) References Cited

OTHER PUBLICATIONS

Japanese Decision of Rejection; Japanese Patent Office; Japanese Patent Application No. 2015-022429; Oct. 3, 2016; 2 pages.

* cited by examiner

HA    Ag-HA-H (a) (b)

(a) (b)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

COATING AND COATING METHOD

CROSS-REFERENCE TO RELATED APPLICATIONS

This application is a continuation of U.S. patent application Ser. No. 12/919,986, filed 27 Aug. 2010, which is a U.S. National Stage patent application filed under 35 U.S.C. §371 from PCT International Application Number PCT/US2009035467, International Filing Date 27 Feb. 2009, International Publication Number WO 2009111307, International Publication Date 11 Sep. 2009, which is incorporated herein by reference in its entirety, which PCT application, and this application, claim priority to U.S. Provisional Patent Application Ser. No. 61/032,621, filed 29 Feb. 2008, and to U.S. Provisional Patent Application Ser. No. 61/051,783, filed 9 May 2008, both of which U.S. Provisional Patent Applications are incorporated herein by reference in their entireties.

The present invention relates generally to coating processes and more particularly to coating processes for implantable prosthesis for mineralized body parts.

BACKGROUND OF THE INVENTION

Medical implants for use in human and animal bodies is known in the arts to serve numerous purposes, both short-term and long-term. One common complication associated with medical implants is infection at the implantation site. Implant related infection is managed by a number of different means, including use of prophylactic systemic antibiotics administered to the patient during set periods before and after implantation surgery. However, infection of the host site remains a common problem, most often requiring a second surgery to remove the implant. The reason for implant removal is that when an infection occurs, the implant acts as the site preferred by the invading bacteria to colonize. When bacterial floras thus colonize the implant, they are extremely resistant to eradication via delivery of antibiotic drugs through systemic means (such as oral or intravenous). The only means to manage such an infection is revision surgery to remove the colonized implant, to be replaced by another implant system. Revision surgery is associated with all of the complications of any surgery, which include infection. Additionally, the patient body now has to deal with morbidities of two surgeries. Other undesirable aspects of revision surgery include blood loss and thrombosis. Revision surgery is also associated with greater risk of implant failure, and the medical prognosis of a revision surgery is never as good as primary surgery. Revision surgery is more costly than primary surgery, and it requires additional longer recovery time for the patient to become fully functional, which can result in loss of productivity. As can be seen in the preceding, revision surgery due to implant site infection is a major medical problem for the patient, and a major drain on the cost of treatment. A technology that reduces or eliminates implant related infection will make an important positive contribution to the patient's well being and the economics of delivering medical care.

It is well known in medicinal arts that the metal silver and its compounds are good antibacterial agents. As such, silver and its compounds are routinely used to treat superficial skin infections. Silver compounds are typically administered to a new born baby's eyes to ward off potential infections. One major advantage of silver compounds over traditional antibiotic drugs is that infectious bacteria do not form resistance to silver. Drug resistant bacteria are a major cause for concern in the field of treating infections. Silver compounds, therefore, have the potential for preventing bacterial infections in medical implants, without the risk of developing resistant strains of bacteria.

Numerous attempts have been made in the past to incorporate metallic silver and/or its compounds into the outer surfaces of medical implants. These attempts and limitations thereof are summarized below.

Silver can be plated (coated) onto medical implants by any number of means known in the arts, including electro-plating, electro-deposition, and painting with an organic polymer carrier. Other techniques for coating include chemical vapor deposition (CVD) and physical vapor deposition (PVD). CVD and PVD techniques are very expensive and require highly sophisticated, controlled manufacturing processes. All of these coating techniques have limited use in implants because the biological interface, i.e., the interface between the implant and the host tissue is completely different for the coated implant versus the uncoated implant. This limitation can have a profound impact on the success of the medical implant, whose biological interface is usually engineered for integration with the host tissue. This need for the implant biological interface to have antimicrobial properties simultaneous with tissue integration properties forms an important aspect of this invention as will be shown later.

Attempts have been made to "implant" ions of silver onto surfaces of medical implants. This technique utilizes energetic beams (high velocity) of ionized silver which are impinged upon the surface of the implant. This technique is referred to as "ion implantation". Silver ion implantation affects only a very thin surface layer (typically in the range of nanometers thick), and therefore has limited use for long-term effectiveness against infectious agents. The "implanted" silver ions may be so well incorporated into the medical implant surface that very little would leach out into the surrounding tissue for effective kill of bacteria. Similar limitations are present in the technique called "ion beam assisted deposition" (IBAD). Ion implantation techniques are also very expensive and require sophisticated, controlled manufacturing processes.

It was discussed previously that the biological interface of the implant, effectively the surface of the implant in contact with host tissue, is typically engineered to integrate with the host tissue. A common surface engineering technology used in medical implants, particularly bone contacting orthopaedic, spinal, and dental implants is hydroxyapatite (HA) coating.

Hydroxyapatite (HA) coatings are applied to medical implants using a number of different methods, including plasma spray, electrodeposition, solution precipitation, and sol-gels methods. Attempts have also been made to incorporate silver into HA. Mainly, the prior art has used the following two different methods to provide a silver-doped HA coating:

One method of incorporating a silver derivative into HA includes the steps of sequentially applying layers of stable silver oxide and HA powder to an implant. However, this method does not form a homogeneous silver-doped HA coating. Consequently, coverage is not uniform, and ion release is not steadily maintained after implantation. Even if the silver oxide is mixed with the HA powder prior to plasma-spraying, the oxide cannot chemically react and combine with conventional HA powder to form a homogenous formulation.

The second method has been to soak an implant having a hydroxyapatite coating in a silver nitrate solution for approximately 24 hours and then dry the implant, in air or an inert environment. This method relies on applying silver into an implant that has already been coated with HA. This post hoc method has the potential of perturbing the physical and mechanical characteristics of the existing HA coating, which may not be desirable from the stand-point of HA attachment to the substrate medical implant. Additionally, this technique does not allow sufficient silver nitrate to soak deep into the HA coating. HA coatings on medical implants can range in thickness from a few to many hundreds of microns. Incorporation of silver by this method requires an ion exchange reaction between silver nitrate and HA coating. This ion-exchange reaction only occurs at the outer surface, where the HA coated implant makes contact with silver nitrate solution. Therefore, although silver is incorporated throughout the HA matrix at the surface, it is not incorporated into the HA matrix at the full thickness of the HA coating. Because silver is incorporated only at the surface and near surface region of the HA coating (and not throughout the thickness), the release of silver ions into the host tissue is likely to be shortlived; that is release of silver ions will not be sustained for very long periods required to ward-off infections a few months after implantation. Moreover, the ion exchange reaction requires careful control of the pH of the silver nitrate solution. The ideal pH of the silver nitrate solution may not be amenable to preservation of the HA structure already coated on the implant. In such a method, the HA coating attachment to the substrate medical implant may be compromised during the soaking process if the pH of the silver salt solution is not controlled.

The preceding discussion shows the limitations of prior art methods of incorporating silver and its compounds into the biological interfaces of medical implants. There is a need for commercially viable means of achieving antimicrobial coatings of medical implants. The ideal medical implant with antimicrobial properties would be such that the manufacturing of the same would not deviate from currently practiced manufacturing processes such as plasma spray.

SUMMARY OF THE INVENTION

In one embodiment of the invention there is provided a coating suitable for a medical implant. Such implants may have beneficial effects, such as they may be able to promote osseointegration and/or simultaneously reduce or eliminate the risk of infection at the implant site.

According to some embodiments, there is provided a coating for a medical implant, in which at least a part of said coating contains an osseointegration agent and the same and/or a different part of the coating contains an antimicrobial metal agent.

According to some embodiments of the present invention, the medical implant has a coating that interfaces with the host biological environment. Such a coating preferably comprises an agent which promotes osseointegration or osteoconductivity, such as a calcium derivative. The term "osseointegration agent" as used herein refers to any agent that has the capability of encouraging the integration of an implant with bone. The term "osteoconductivity" refers to the situation where the implant is able to support the attachment of new osteoblasts and osteoprogenitor cells, providing a structure through which new cells can migrate and new vessels can form.

It is to be understood that the term "calcium derivative" as used throughout the description is used as a representative term for an agent that may promote osseointegration or osseoconductivity, and is frequently referred to as hydroxyapatite (HA), but can be any suitable derivative, examples of which the skilled person is well aware. One example is HA, but other derivatives such as calcium phosphate, calcium orthophosphate, tricalcium phosphate, ceramic bioglass can all serve the function of this invention, and are incorporated herein without limitation. Other forms of surface engineering to enhance integration of the implant to host tissue include coatings apatites such as calcium phosphate, hydroxyapatite, β tricalcium phosphate, a mixture of hydroxyapatite and β tricalcium phosphate, resorbable polymers, bioglass, derivatised phosphate-based compound, orthophosphates, monocalcium phosphates, octacalcium phosphates, dicalcium phosphate hydrate (brushite), dicalcium phosphate anhydrous (monetite), anhydrous tricalcium phosphates, whitlocktite, tetracalcium phosphate, amorphous calcium phosphates, fluoroapatite, chloroapatite, non-stoichiometric apatites, carbonate apatites, biologically-derived apatite, calcium hydrogen phosphate, calcium hydrogen apatite, water insoluble ceramics, phosphates, polyphosphates, carbonates, silicates, aluminates, borates, zeolites, bentonite, kaolin, and combinations thereof. These techniques of surface engineering are incorporated herein without limitation.

In some embodiments, the calcium derivative is one, or a combination, of hydroxyapatite and/or β tricalcium phosphate.

According to some embodiments of the present invention, the antibacterial efficacy of the native calcium derivative (e.g. HA) coating is improved by the addition of silver.

The silver may be present as one or more of a silver-substituted calcium derivative (such as HA) and/or discrete metallic silver particles.

Preferably, the antimicrobial metal agent is present in at least a part of said coating as discrete particles. The antimicrobial metal may comprise one or more of silver, copper, and/or zinc. The discrete particles (e.g. silver particles) may preferably be distributed throughout the entire coating thickness.

The present inventors have found that it is preferable to have metallic silver incorporated into the medical implant rather than a discrete compound of silver (such as silver oxide).

The use of silver (or other antimicrobial metallic species such as copper) can be engineered in a number of ways. Because the metallic anti microbial is to be used in host animal (including human) tissue, its properties should serve the following non-limiting important functions:

(a) The antimicrobial treated medical implant should resist bacterial colonization. The chemical form of silver present in the coating can influence this. For instance, silver can be present in the coating on the implant surface as a chemical compound, such as silver phosphate, silver oxide, silver nitrate, and other compounds. Silver can also be present in the metallic silver form. Additionally, a mixture of silver compounds and/or metallic silver can be present. The exact composition will influence the ability of the implant to resist microbial colonization upon implantation, and over time as the antimicrobial coating reacts in the host tissue environment.

(b) The antimicrobial treated medical implant should release the antimicrobial metal into the host tissue to affect its antimicrobial properties. The antimicrobial metal can be released into the host tissue as ions of silver or as metallic silver, or as a compound of silver (e.g., silver phosphate or silver oxide). The chemical nature of antimicrobial release will depend on the composition of the coating. It is appreciated that the preferred type of release (ionic, metallic, or compound) can be controlled by the composition of the antimicrobial coating.

(c) The release kinetics of silver into the host environment may be in the form of a burst release (bolus) or sustained over a long period of time or a combination of burst and sustained release. The release kinetics and duration of release can be engineered by the selection of the chemical nature of the silver and its compounds in the coating, as discussed above.

(d) The release of silver in the forms discussed above should be in doses that are well tolerated by the host living tissue, organ, and organism. The release should not interfere to appreciable degree with other biological and mechanical functions of the implant and the coating. The coating and the release of silver should be biocompatible and should not present a cytotoxic challenge to the host environment. This can be controlled, as listed above.

The type and concentration of silver and its compounds present in the antimicrobial coating can be controlled by any number of means. Silver can be incorporated into coating particulate (such as HA) by an ion exchange reaction with silver nitrate or other silver compound as known in the arts. After the ion exchange reaction, the excess silver compound can be completely rinsed out of the HA powder, or just partially rinsed. Therefore the HA powders can contain no unreacted silver compounds or can retain all of the unreacted excess silver compounds, or can retain partial quantities of unreacted silver.

In some embodiments, the discrete metal particles (e.g. metallic silver particles) are present in a coating having an osseointegration agent that is not itself substituted with an antimicrobial metal agent. Optionally, the metal particles are distributed in a coating having an osseointegration agent which has also been substituted with an antimicrobial metal agent. Preferably the metal agent is silver and is present in the coating as silver substituted into the osseointegration agent.

Optionally, one method of providing a coating to a medical implant is by a technique called "plasma spray". The thickness of the plasma sprayed coating on a medical implant can typically be from about 1 micron, and typically is in the range of 10 or a few tens to a few hundreds of microns. Coating thickness in excess of a few thousand microns (one millimeter or greater) are also possible. Other methods of applying calcium-derivative coatings onto medical implants include sol-gel methods, electrodeposition, solution precipitation, and biomimetic coatings.

According to some embodiments of the present invention the implant is plasma-sprayed with a powder of an osseointegration agent (e.g. calcium derivative such as HA). Preferably, the osseointegration agent is at least partially substituted with an antimicrobial metal agent (e.g. silver) prior to plasma spraying.

Plasma spray coating can be applied under atmospheric conditions or under reducing conditions, or in a vacuum. Additionally, the plasma spray equipment can be under controlled environmental conditions. For instance the environment may contain argon, or other inert gases. Or the environment may contain reactive gases. The environment under which the plasma spray equipment is operated under can determine the type of silver (or compound thereof) that is incorporated into the HA coating. For instance, atmospheric (uncontrolled environment) HA coating can lead to oxidation of silver (and compounds thereof) already present in the HA particles via the ion exchange reaction as they exit the plasma and before they are coated onto the implant surface. Vacuum plasma spraying can ameliorate this oxidation reaction. If specific silver compounds are desirable, then the environment of the plasma spray equipment can be controlled to affect production of such compounds. If, for instance it is desirable to have silver fluoride as the silver compound in the HA coating, then the environment can be enriched in fluorine by any number of means known in the arts.

In one embodiment, no post-process heat treatment is required to further consolidate the coating or bond it to the substrate.

If plasma spraying is to be utilised in the present invention, the plasma spraying is preferably of at least one layer of the coating which contains an antimicrobial agent (such as silver) is conducted in a reducing environment.

Thus, in one embodiment of the invention there is provided a plasma sprayed coating for a medical implant, in which at least a part of said coating contains an osseointegration agent and the same and/or a different part of the coating contains an antimicrobial agent.

Preferably the osseointegration agent is a calcium derivative.

Preferably at least a part of the coating containing the antimicrobial agent has been plasma sprayed under reducing conditions, and preferably plasma spraying is conducted in a vacuum.

Without wishing to be bound by theory, it is believed that when powders such as HA contain unreacted silver compounds, these compounds will dissociate into metallic (elemental) silver in the highly reducing environment (hydrogen and inert gas mixture) of the plasma. Therefore, if the plasma spraying is conducted in a vacuum condition, the reduced metallic silver will be coated onto the medical implant as discrete metallic particles along with the HA and silver-containing HA. On the other hand if the plasma spray process was conducted under atmospheric conditions, the metallic silver formed in the reducing atmosphere of the plasma will react with oxygen to form an oxide. These oxides then are coated onto the medical implant along with HA and silver containing HA. It can be appreciated from the previous discussion that the type of silver present on the medical implant can be controlled by the process of applying the coating onto the medical implant.

In some embodiments of the present invention, at least a part of said coating contains discrete particles of an antimicrobial metal. In some embodiments, said antimicrobial metal comprises one or more of metallic silver, copper, and/or zinc.

Preferably the antimicrobial metal comprises metallic silver. In some embodiments, the metallic silver particles are spherical or irregular in shape. Further, the diameter of the metallic silver particles range from about 15 nm to about 10 um in size.

In some embodiments of the invention, the silver concentration is sufficient to have an anti-bacterial effect, such as having a concentration from about 0.1 to about 10 weight percent.

In some embodiments, said calcium derivative contained in said at least a part of said coating containing a calcium derivative is silver-substituted, and preferably that silver-substituted calcium derivative has a silver concentration that is homogenously distributed throughout the thickness of the coating. The silver-substituted calcium derivative may contain from about 0.1 to about 10% by weight of silver, preferably from about 0.5 to about 3.0% by weight of silver.

In some embodiments, the at least a part of said coating that contains the antimicrobial agent has the agent distributed throughout the entire thickness of the part of the coating.

With careful control of the manufacturing process, then, it is possible to create plasma sprayed HA coated medical implants, which contain any one or a combination of two or more of the following types of silver in the HA coating:
(1) The silver can be present up to a fixed depth from the outer surface of the HA coating, or it can be present at the full thickness of the HA coating.
(2) The silver can be in the form of a silver compound (e.g., silver phosphate, silver oxide) that is fully reacted with the HA and homogeneously distributed throughout the HA coating. Alternatively the silver compound can be distributed discretely into the matrix of the HA coating.
(3) The silver can be fully incorporated into the native HA crystal structure as silver-modified HA, and homogeneously distributed throughout the HA coating.
(4) The silver can be in the form of metallic silver that forms in the reducing atmosphere of the plasma. Such silver is distributed as discrete particles of silver in the matrix of the HA coating. The metallic silver can be present up to a fixed depth from the outer surface of the HA coating, or it can be present at the full thickness of the HA coating.

In some embodiments of the invention, the coating is preferably greater than about 1 nm in thickness, preferably from about 10 μm to about 200 μm, and most preferably from about 30 μm to about 100 μm. Said coating is preferably well-adhered to the substrate material (e.g. Ti6Al4V, cp-Ti, CoCrMo, Ta, and other biomedical materials) and possesses a tensile bonding strength for example of at least 15 MPa.

According to some embodiments of the present invention, the osseointegration of native calcium derivative (e.g. HA) coating is not compromised by the addition of silver.

In some embodiments of the present invention, the coating has one or more osteoconductive, osteopromotive and/or antimicrobial properties.

According to some embodiments of the present invention the coating is formed from a homogeneous formulation of a calcium derivative (e.g. HA) powder containing silver. In some embodiments, no blending of the silver-containing calcium-derivative powder with other silver-containing powders is required to incorporate silver into the coating. For example, in one embodiment, no blending of HA powder with other powders (e.g. silver oxide powder) is required to incorporate silver into the HA coating.

According to some embodiments of the present invention the osteointegration agent (e.g. HA) powder contains at least partially excess silver reactant adsorbed onto the surface.

According to some embodiments of the present invention the HA powder contains both silver substitution and excess silver reactants.

According to some embodiments of the present invention the silver reactant for substitution into osseointegration agent (e.g. HA) powder is one or more of a silver salt, such as silver nitrate ($AgNO_3$) and/or silver fluoride (AgF). Alternatively, or in addition, the silver reactant can be one or more of a silver halide, such as silver iodide.

In some embodiments of the present invention, the calcium derivative, in addition to silver, is also substituted with one or more of the following: carbonate, fluoride, silicon, magnesium, strontium, vanadium, lithium, copper, and/or zinc.

According to some embodiments of the present invention, the silver containing calcium derivation (e.g. HA) powder is formed by first soaking conventional HA powder in a silver nitrate-containing and/or silver fluoride-containing aqueous or organic solution for a period of time. In some embodiments the aqueous or organic solution may comprise both silver fluoride and silver nitrate.

It is preferred that the calcium derivative (e.g. HA) powder soaks and stirs in the solution for a suitable time to allow sufficient ion exchange reaction between HA powders and Ag Salt(s) solution. Such a time period can range from a few hours (e.g. 10 hours) to a week, such as a period of approximately one day to three days. The reaction is more preferably about two days. For best results, it may be necessary to avoid excessive exposure of the mixture to light.

The osseointegration agent (e.g. HA) powder may soak at room temperature, however, a slightly warmer temperature is preferred in order to increase solubility of the solution into the HA. The temperature should not be elevated so much as to break down the composition.

It is also generally important to maintain a proper pH level of the solution during the time in which the HA powder is reacting with Ag Salts in the aqueous or organic solution. The pH should generally be kept at level such that there is a minimum of HA dissolution but at the same time reduce the possibility that the silver nitrate will react with OH and precipitate to form silver hydroxide and eventually becomes silver oxide. The pH level may be maintained in the range of 6.5-8.5, but is preferably above 6.7 to prevent the HA from dissolving. More preferably, the pH level of the mixture is in the range of 6.8-7.2, but other levels may be acceptable.

After the ion exchange reaction, the mixture may be left to air dry or may be rinsed and/or washed with deionized and distilled water ($DDH_2O$) and then allowed to air dry.

In some embodiments of the present inventions, there is provided a method for preparing an antimicrobial coating, in which a silver-containing calcium derivative powder is produced by ion-exchange or sol-gel methods and subsequently plasma sprayed onto a substrate material.

In some embodiments, the silver-containing calcium derivative powders are produced by: a. suspending calcium derivative powder in a silver salt solution for a time and temperature sufficient to exchange calcium ions for silver ions, and b. drying said ion-exchanged and washed calcium derivative.

In some embodiments, an additional step is performed between steps (a) and (b) of washing said ion-exchanged calcium derivative powders.

In some embodiments, the ion exchange reaction between the calcium derivative powder and silver salt solution occurs for about 24 to 168 hours at a temperature of from about 20° C. to 95° C. In some embodiments, the silver salt solution is silver nitrate or silver fluoride with a concentration of $10^{-2}$-$10^{-4}$ M and the mass ratio of silver nitrate to HA powder is within the range of 0.01-0.1.

Further, in some embodiments, the silver-containing calcium derivative powders are produced by a sol-gel method by:
(a) Mixing a combination of calcium, silver, and/or phosphorus precursors to obtain a homogenous sol-gel solution;
(b) Aging the sol-gel solution at the temperature between 20-95° C. for a suitable time period;
(c) Drying and calcining the sol-gel solution at a temperature above room temperature for a suitable time period;
(d) Processing the calcined powders to a desired particle size distribution for subsequent plasma spraying process.

In some embodiments, the calcium precursor is calcium nitrate. In some embodiments, the silver precursor is silver nitrate. In some embodiments, the phosphorus precursor is ammonium dihydrogen phosphate. In some embodiments, the silver precursor concentration range is from about 0.1 wt % to 10 wt %, preferably from 0.5 wt % to 3.0 wt %.

In certain embodiments, fluorine and carbonate precursors are mixed with the calcium, silver, and phosphorous precursors to obtain a homogenous sol-gel solution. In some embodiments, the fluorine precursor is ammonium fluoride. In some embodiments, the carbonate precursor is ammonium carbonate. In some embodiments, the F and/or carbonate precursor concentration is about $10^{-2}$-$10^{-3}$M.

In certain embodiments, carbonate, fluoride, silicon, magnesium, strontium, vanadium, lithium, copper, or zinc precursors, or combinations thereof, are mixed with the calcium, silver, and phosphorous precursors to obtain a homogenous sol-gel solution.

The remaining solid mixture comprises a homogenous HA powder formulation having silver and/or fluoride therein. The homogenous HA powder formulation may or may not be ground up and then used in a conventional plasma spray process to coat a biomedical implant or medical device as would normal HA powder. The soaking and grinding process of the present invention generally only negligibly increases the mean particle size of the HA powder, and thereby does not interfere with subsequent plasma spray processes that may be dependent on conventional equipment.

In some embodiments, the size distribution of the silver-containing calcium derivative powder formulation prior to spraying is substantially equivalent to native pure calcium derivative powder.

One possible advantage of using the aforementioned air drying process without rinsing is that by not rinsing there may be a small amount of excess silver nitrate or silver fluoride in addition to the homogeneous HA/silver powder formulation after the aqueous/organic solution evaporates. This might ensure that after the extremely high temperatures present during the plasma spraying process, some residual (i.e. "extra") silver is present in the coating, even if some of the silver in the homogeneous HA powder vaporizes. The silver content and degradation profile in the final plasma sprayed coating can be tailored using different concentration of silver salts.

In one embodiment of the invention, there is provided a method of treating a patient requiring a surgical implant, the method comprising the steps of operating on the patient, inserting a medical implant having a coating of any of the embodiments described herein into the operating site, and leaving the implant in situ after the operation, in which the implant reduces the risk of, or eliminates, post-operative infection at the site of the implant.

As used herein, the term "silver" may comprise substantially pure silver, a composition having a silver-based component, a precursor having a silver-based component, a silver compound, or an alloy having silver. From the preceding discussion, it is possible that silver and/or silver compounds can be incorporated into the biological interface (such as HA coating) of the medical implant, in such a manner that the surface simultaneously serves an antimicrobial function.

Other metallic species are also known to have similar antimicrobial effects. These include, but are not limited to, copper, zinc, mercury, lead, and other metals. These metallic species have a wide range of effectiveness depending on the dose delivered. Additionally, some of these metallic species may be toxic to the host tissue, also depending on the dose used and the tissue site in which they are applied. Although this invention relates to silver as the preferred antimicrobial metallic species, it is not limited solely to silver. Mixtures of different metallic species can also be used. For instance varying amounts of silver and copper compounds can be used.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

Figure 1:
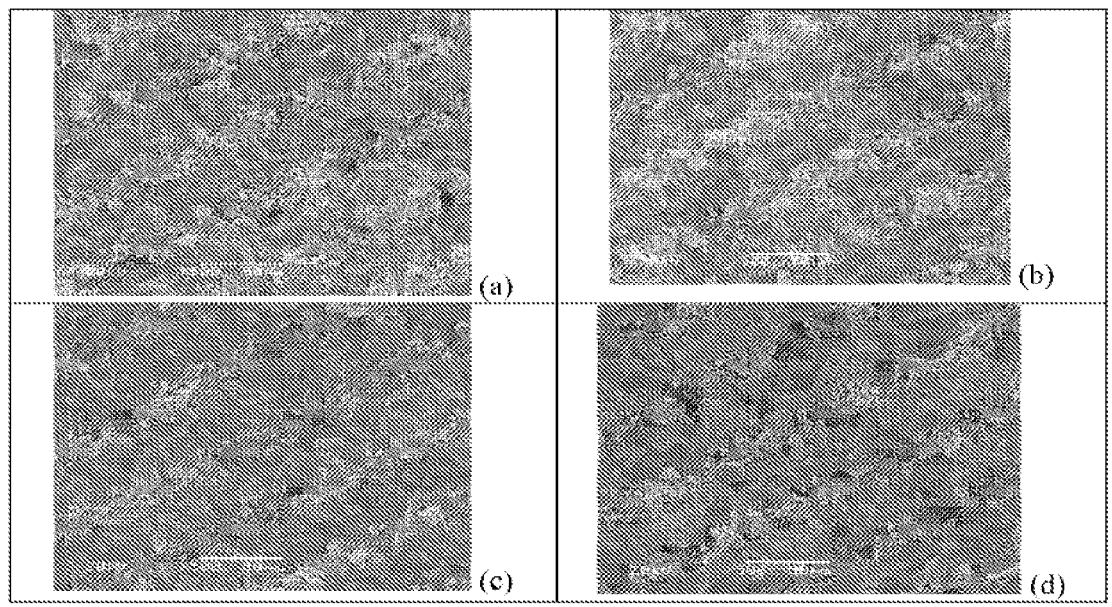
FIG. 1 is a scanning electron micrograph of HA (a), Ag-HA-L (b), Ag-HA-M (c) and Ag-HA-H (d)-coated Ti6Al4V discs.

The following description of the depicted embodiment(s) is merely exemplary in nature and is in no way intended to limit the invention, its application, or uses.

An antimicrobial HA powder formulation is formed by first soaking conventional hydroxyapatite (HA) powder (such as a commercially available HA powder having an average particle size of about 45 to about 125 microns) in a silver nitrate-containing and/or silver fluoride-containing aqueous or organic solution for a period of time. In some embodiments the aqueous or organic solution may comprise both silver fluoride and silver nitrate. In some embodiments, beta tricalcium phosphate may be used or HA may be combined with beta tricalcium phosphate. The calcium phosphate mixture includes about 0.1 percent to about ten percent by weight of silver, from about 0.1 wt % to about 7 wt %, or from about 0.1 wt % to about 5 wt %. In one particular embodiment, the calcium phosphate mixture includes about 0.5 percent to about three percent by weight of silver, or from about 0.5 wt % to about 2 wt %.

The term "wt %" or "weight percent" refers to the % of the weight of the coat or the layers within the coat, and does not include the weight of the implant itself.

In some embodiments, one or more of carbonate, fluoride, silicon, magnesium, strontium, vanadium, lithium, copper, and zinc may be added to the calcium phosphate mixture.

The HA powder soaks and stirs in the solution for a period of about one day to about seven days. It is preferred that the HA powder soaks and stirs in the solution for a period of approximately one day to three days to allow sufficient ion exchange reaction between HA powders and Ag Salt(s) solution. The reaction is more preferably about two days. Further, for best results, it may be necessary to avoid excessive exposure of the mixture to light.

The HA powder may soak at room temperature, however, a slightly warmer temperature is preferred in order to increase solubility of the solution into the HA. The temperature should not be elevated so much as to break down the composition. In some embodiments, a temperature range of about 20 degrees Celsius to about 95 degrees Celsius may be used. In other embodiments, a temperature range of about 60 degrees Celsius to about 80 degrees Celsius may be used.

It is also generally important to maintain a proper pH level of the solution during the time in which the HA powder is reacting with Ag Salts in the aqueous or organic solution. The pH should generally be kept at level such that there is a minimum of HA dissolution but at the same time reduce the possibility that the silver nitrate will react with OH and precipitate to form silver hydroxide and eventually becomes silver oxide. The pH level may be maintained in the range of 6.5-8.5, but is preferably above 6.7 to prevent the HA from dissolving. More preferably, the pH level of the mixture is in the range of 6.8-7.2, but other levels may be acceptable.

After the ion exchange reaction, the mixture may be left to air dry or may be rinsed and/or washed with deionized and distilled water ($DDH_2O$) and then allowed to air dry.

The remaining solid mixture comprises a homogenous HA powder formulation having silver and/or fluoride therein. The homogenous HA powder formulation may be ground up and then used in a conventional plasma spray process to coat a biomedical implant or medical device as would normal HA powder. The soaking process of the present invention generally only negligibly increases the mean particle size of the HA powder, and thereby does not interfere with subsequent plasma spray processes that may be dependent on conventional equipment.

In a first method, HA powder is combined with an AgF solution. The mixture soaks and is stirred for one to three days. The mixture is dried. The resulting formulation may be plasma sprayed onto a medical implant. As an example, the silver fluoride may have a concentration of about $1 \times 10^{-2}$ to about $1 \times 10^{-4}$ M. As an example, the mass ratio of silver fluoride to HA powder is within the range of about 0.01 to about 0.1. In one embodiment, the mixture is dried in air for about one day to about three days at a temperature of between about 50 degrees Celsius to about 95 degrees Celsius. In yet another embodiment, the silver solution has a concentration in the range of $1 \times 10^{-3}$ to about $1 \times 10^{-4}$ M.

In a second method, HA powder is combined with an $AgNO_3$ solution. The mixture soaks and is stirred for one to three days. The mixture is dried. The resulting formulation may be plasma sprayed onto a medical implant. As an example, the silver nitrate may have a concentration of about $1 \times 10^{-2}$ to about $1 \times 10^{-4}$ M. As an example, the mass ratio of silver nitrate to HA powder is within the range of about 0.01 to about 0.1. In one embodiment, the mixture is dried in air for about one day to about three days at a temperature of between about 50 degrees Celsius to about 95 degrees Celsius.

In a third method, HA powder is combined with an AgF and $AgNO_3$ solution. The mixture soaks and is stirred for one to three days. The mixture is dried. The resulting formulation may be plasma sprayed onto a medical implant.

In a fourth method, HA powder is combined with an AgF solution. The mixture soaks and is stirred for one to three days. The mixture is rinsed. The mixture is then dried. The resulting formulation may be plasma sprayed onto a medical implant.

In a fifth method, HA powder is combined with an $AgNO_3$ solution. The mixture soaks and is stirred for one to three days. The mixture is rinsed. The mixture is then dried. The resulting formulation may be plasma sprayed onto a medical implant.

In a sixth method, HA powder is combined with an AgF and $AgNO_3$ solution. The mixture soaks and is stirred for one to three days. The mixture is rinsed. The mixture is then dried. The resulting formulation may be plasma sprayed onto a medical implant.

In some embodiments, the silver-containing HA powders are produced by sol-gel method by (a) mixing calcium, silver, and/or phosphorus precursors to obtain a homogenous sol-gel solution; (b) aging the sol-gel solution at a temperature between about 20 degrees to about 95 degrees Celsius for about seven to about 9 days; (c) drying and calcining the sol-gel solution at an elevated temperature ranging from about 500 to about 800 degrees Celsius for about 2 to about 4 hours; and (d) grinding and sieving the calcined powders above to a desired particle size distribution for subsequent plasma spraying process. In some embodiments, the average particle size is about 45 to about 150 microns. As examples, the calcium precursor may be calcium nitrate, the silver precursor may be silver nitrate, and the phosphorus precursor may be ammonium dihydrogen phosphate. The silver precursor concentration may be in the range from about 0.1 weight percent to about 10 weight percent, from about 0.1 wt % to about 7 wt %, or from about 0.1 wt % to about 5 wt % and more preferably from about 0.5 weight percent to about three weight percent or from about 0.5 wt % to about 2 wt %.

In some embodiments, a base layer or primer layer may be applied to the substrate prior to application of the calcium phosphate coating. The base layer may be used to avoid or reduce a reaction between the substrate and the coating. Alternatively, the base layer may improve the tensile bonding strength at the coating-substrate interface. The base layer may be applied using a vacuum plasma spraying process. Alternatively, the base layer may be applied using atmospheric plasma spraying, ion sputtering, sol-gel dip coating method, solution precipitation, biomimetic method, or electrodeposition. The base layer may be any number of compounds. As examples, the base layer may be a metallic coating, a ceramic coating, or a biodegradable bioceramic coating. In particular, the base layer may include calcium phosphate, bioglass, calcium polyphosphate, tetracalcium phosphate (TTCP), 3-tricalcium phosphate (TCP), 3-calcium pyrophosphate (CPP), 3-calcium metaphosphate (CMP), or substantially pure HA. In one particular embodiment, the base layer thickness is about 1 to about 50 microns, and more preferably about 10 to about 20 microns. In one specific embodiment, the total thickness of base layer and the antimicrobial coating is about 30 to about 300 microns, and more preferably about 50 to about 100 microns.

In some embodiments, fluorine and carbonate precursors may be mixed with the calcium, silver, and phosphorous precursors to obtain a homogenous sol-gel solution. As examples, the fluorine precursor may be ammonium fluoride and the carbonate precursor may be ammonium carbonate. The fluorine precursor concentration may be in the range from about $10^{-2}$ to about $10^{-3}$ M. The carbonate precursor concentration may be in the range from about 0.1 to about $10^{-3}$ M.

In some embodiments, bone stimulating materials are mixed with the calcium, silver, and phosphorous precursors to obtain a homogenous sol-gel solution. As examples, salts, minerals, metals, metal oxides, carbonate, fluoride, silicon, magnesium, strontium, vanadium, lithium, copper, or zinc precursors, or a combination thereof, may be mixed with the calcium, silver, and phosphorous precursors to obtain a homogenous sol-gel solution.

One of ordinary skill in the art may readily appreciate that the exact amount or concentration of silver nitrate and/or silver fluoride in the solution may vary. Only a small portion of the silver nitrate and/or silver fluoride may be absorbed into the HA powder, and therefore, concentration of the solution may be optimized for reduction of silver nitrate or silver fluoride waste. Alternatively, extra silver fluoride and/or silver nitrate may be added to the solution to compensate for some evaporation/vaporization of silver and/or fluorine during plasma spray.

In addition, strontium and/or vanadium may be used alone or in combination with the silver and/or fluoride of the present invention, as well as other metals like copper and zinc.

By adding a small amount of silver and/or fluoride to conventional HA powder, the present invention provides improved antimicrobial/anti-infection/osteointegration properties to a biomedical implant. Moreover, the prior art fails to provide a homogeneous formulation HA powder capable of being plasma sprayed as does the present invention. The homogenous HA/silver powder formulation of the present invention may provide a much more uniform and controlled degradation coating after plasma-spraying than the non-homogeneous application of silver and HA separately.

Although the examples above include hydroxyapatite, those having ordinary skill in the art would understand that other forms of calcium phosphate may be used. As examples, apatites non-stoichiometric apatites, calcium phosphates, orthophosphates, monocalcium phosphates, dicalcium phosphates, tricalcium phosphates, whitlockite, tetracalcium phosphates, amorphous calcium phosphates may be substituted for HA.

The present invention also provides a variety of medical implants, preferably coated using any of the methods and techniques as described herein. The coating of the medical implant can comprise one or more layers, in which each layer may comprise the same or different composition as another layer. Each layer is preferably plasma sprayed in a reducing environment (e.g. in a vacuum).

Optionally, the medical implant has a coating which comprises a number of layers, and in which the concentration of antimicrobial agent is different in at least two coating layers.

The implants of the present invention are preferably manufactured to increase the chances of successful integration into the host environment, whilst at the same time providing an antimicrobial environment to reduce the risk of, or prevent, infection.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

EXAMPLES

Example 1

Methods

Three different concentrations of silver nitrate solutions were prepared in distilled and de-ionized water ($DDH_2O$) for the ion exchange reaction between silver nitrate solution and HA powders. Some Ag ions from the silver nitrate solution will substitute Ca ions from the HA structure, meanwhile, some silver compounds will be physically adsorbed on the HA surface. The target silver content in the HA powders was 0.3 wt %, 1 wt %, and 3 wt %, respectively. The mass of the silver nitrate and the HA powder was listed in Table 1.

TABLE 1

The mass of silver nitrate and HA powder used for the ion exchange reaction

| | $AgNO_3$ | HA | $DDH_2O$ | Target Ag wt % |
|---|---|---|---|---|
| Pure HA | — | 250 g | — | 0 |
| Ag-HA-L | 1.25 g | 250 g | 750 mL | 0.3 |
| Ag-HA-M | 4.0 g | 250 g | 1500 mL | 1.0 |
| Ag-HA-H | 12.0 g | 250 g | 3000 mL | 3.0 |

Silver nitrate (BDH, Cat.# BDH0276-125G) was first dissolved in $DDH_2O$ contained within a 3 liter glass beaker, and then the HA powders (MEDIPURE®, MEDICOAT AG, particle size: −125 μm+45 μm) were added into the prepared silver nitrate solution according to Table 1. The HA and silver nitrate solution was stirred at 180 RPM in an orbital shaker at room temperature for 3 days to allow a homogeneous ion exchange reaction.

After the ion exchange reaction, the solution was left to dry at 80° C. in an oven to evaporate the water. The dried and modified HA powders were then slightly ground manually using pestle and mortar to break the agglomerates formed during the drying process. The ground modified HA powders were then sieved through 100-325 mesh sieve (W.S. Tyler, Inc., USA). Any HA powders that were larger than 150 nm or smaller than 45 nm were discarded. At least 98% HA powders were collected between 100-325 mesh sieves.

The silver modified HA powders were further characterized using a Laser Diffraction Particle Size Analyzer (Model LS 13 320, Beckman Coulter, USA). All the measurements were listed in Table 2. The average particle size was slightly increased with the increase of the silver content in the HA powders. The particle size distribution of the low and medium silver HA powders were similar to the control pure HA powders.

TABLE 2

Particle size and size distribution of pure HA and modified HA powders

| | Mean (μm) | D10 (μm) | D25 (μm) | D50 (μm) | D75 (μm) | D90 (μm) |
|---|---|---|---|---|---|---|
| Pure HA | 96.94 ± 2.07 | 64.68 | 85.96 | 111.6 | 137.5 | 159.2 |
| Ag-HA-L | 96.66 ± 1.85 | 63.08 | 83.13 | 108.4 | 134.1 | 156.0 |
| Ag-HA-M | 99.28 ± 1.71 | 64.06 | 83.80 | 109.0 | 135.0 | 157.4 |
| Ag-HA-H | 106.9 ± 1.71 | 68.89 | 88.45 | 113.4 | 139.2 | 160.8 |

X-ray Diffraction (XRD) was utilized to characterize the structure, phase compositions, and the grain size of the powders (pre-spraying). This analysis was performed at H&M Analytical Services, Inc. (Allentown, N.J., USA). The coated samples were placed on a standard sample holder and put into a Philips PW3020 diffractometer using Cu radiation at 40kV30 mA. Scans were run over the range of 10° to 70° with a step size of 0.02° and a counting time of 8 hours each. Scanning Electron Microscopy coupled with Energy Dispersive X-ray Analysis (JEOL JSM-6460LV, Japan) was used to examine the surface morphology, Ca/P ratio, Ag content of the coating, and the coating thickness.

The silver modified powder was further analyzed for composition by completely dissolving the powder (pre-spraying) in 10% Nitric acid solution. An aliquot was withdrawn from the nitric acid solution for silver ion concentration analysis using inductively coupled plasma (ICP) mass spectroscopy.

These silver modified HA powders were then used in a conventional vacuum plasma spray process at Medicoat (Magenwil, Switzerland) for the silver containing HA coatings. All substrates onto which the powders were sprayed were made from mill-annealed Ti6Al4V alloy. The flat-surfaced disc samples were 12.6 mm in diameter and 3.1 mm in thickness. These coupons were grit blasted and cleaned prior to plasma spraying. All the spray parameters were the same for both pure HA powders and the silver modified HA powders. A stainless steel plate with D12.6 mm holes was used to mount Ti6Al4V coupons. After the coating process, the as-sprayed coatings were rinsed with isopropanol.

X-ray Diffraction (XRD) was utilized to characterize the structure, phase compositions, and the grain size of the coatings in the same manner used for the powders.

Three one-inch diameter Ti6Al4V coupons from each of four groups were used as substrates to deposit HA or Ag doped HA coatings to assess the tensile attachment strength of the coatings in a manner similar to that described in ASTM F1 147.

The back-side of each coupon and the ends of the testing stubs were all lightly sanded with 80-grit paper to enhance epoxy attachment strength. The back-side of the coupons (i.e. no-coated surface) was cleaned with acetone and allowed to air-dry for 2-3 minutes.

Tensile testing stubs were glued to the opposing surfaces of each coupon using one layer of FM1000 adhesive on the back surface and one layer on the coating surface. This was done by assembling the constructs in a curing fixture and placing the fixture in a convection oven for 130 minutes (or 135 minutes if two fixtures were put in the oven simultaneously) at a temperature of 338° F. (170° C.) under a dead weight load of 2.3 lbf (10 N) to thermal cure the glue. After removing the fixture from the oven and allowing it to cool to room temperature, the dead weights were removed and the constructs were taken out of the fixture.

Each construct was tested by subjecting it to a tensile load at a displacement rate of 0.10 in/min (2.5 mm/min) until failure. The peak load and failure mode for each construct was recorded. The tensile attachment strength was determined by dividing the peak load by the cross-sectional area of the coupon. After testing, each coupon was inspected to ensure that glue did not penetrate to the substrate, which would indicate an invalid test.

One sample was used for each condition for silver release evaluation from the coating. The coated disc samples were soaked in 2 mL of PBS (pH=7.4) at 37° C. for 24, 72, and 168 hours. At each time point, 1mL solution was withdrawn and stored in an eppendorf tube at 4° C. refrigerator before Inductively Coupled Plasma (ICP) silver analysis which was carried out at Environmental Testing & Consulting, Inc. Memphis, Tenn. 15 μL of concentrated nitric acid was added into the tube to prevent the silver deposition from the solution.

Results

The XRD and ICP results of the silver modified HA powders are listed in Table 3 below. The Total Ag (XRD) is the result from the powder XRD phase composition analysis. XRD results demonstrated that the silver was present as either metallic silver, silver nitrate (i.e. the original silver ion exchange reaction media containing silver), or silver oxide. It should be noted that XRD only determines crystalline phases of metallic silver or silver compounds. It does not detect silver that has been substituted into the HA crystal. ICP was used to determine the total amount of Ag in the silver modified HA powder. ICP analysis measures all silver present-silver present as substituted in the HA crystals and silver present as a discrete compound separate from the HA crystals (e.g. silver nitrate, silver oxide, and metallic silver). The amount of silver contained in the HA crystals can be determined by subtracting the XRD from the ICP results. For example, for the 1 wt % Ag-HA powder, XRD results showed there was 0.45 wt % of silver in the silver modified HA powder; however, the ICP result of the same powder showed the total Ag content in this modified powder was 0.98 wt %, which was close to the designed total silver concentration. Therefore, this indicates that about 54% of silver was substituted into the HA structure. The excess silver from silver nitrate ion exchange solution was converted to other Ag phases as identified by XRD after VPS process.

TABLE 3

| Phase Identification | After Ion Exchange Reaction (Before VPS) | | |
|---|---|---|---|
| | Ag-HA powder (Low-0.3 wt %) | Ag-HA powder (Med-1 wt %) | Ag-HA powder (High-3 wt %) |
| $Ca_{10}(PO_4)(OH)_2$ | 99.7 ± 1.0% | 99.4 ± 1.0% | 97.2 ± 1.0% |
| Ag | 0.1 ± 0.1% | 0.2 ± 0.1% | |
| $Ag_2O$ | | | 0.9 ± 0.1% |
| $AgNO_3$ | 0.2 ± 0.1% | 0.4 ± 0.1% | 1.8 ± 0.1% |
| $Ca(OH)_2$ | | | 0.2 ± 0.1% |
| Total Ag (XRD) | 0.23 | 0.45 | 1.98 |
| Total Ag (ICP) | 0.22 | 0.98 | 2.81 |

FIG. 1 represents the scanning electron micrograph of the pure HA (a), Ag-HA-L (b), Ag-HA-M (c), and Ag-HA-H (d)-coated Ti6Al4V disc samples showing the surface appearance of the coatings. In general, all the coatings appeared uniform and covered the Ti6Al4V substrate. There was no obvious difference between the silver containing HA coatings and the pure HA coatings. A cross section of the HA and the Ag-HA-H samples indicates the thickness of the coating is about 80 μm, FIG. 2. The silver concentration was measured at different locations throughout the coating for the Ag-HA-H sample, as indicated by the "x" markers.

Quantitative energy dispersive X-ray analysis (EDXA) shows the Ca/P ratio and Ag contents in the coatings in Table 4. At least 10-15 random selected areas were used per sample to collect the spectra for this quantitative analysis. The Ca/P ratio decreased with increasing silver content, which indicates an increasing substitution of Ag in the HA lattice with increasing Ag in the coating. Furthermore, Ag was identified through the thickness of the Ag-doped coatings (FIG. 2; Table 5).

The Ag contents of the doped HA coatings were higher than that measured by ICP (Table 3), which is likely due to surface roughness artifacts associated with EDXA analysis.

TABLE 4

Ca/P ratio and silver content analysis using EDAX

| | Ca/P | Ag (wt %) |
|---|---|---|
| HA | 1.72 | 0 |
| HA-L | 1.65 | 1.2 |
| HA-M | 1.61 | 2.7 |
| HA-H | 1.54 | 6.3 |

TABLE 5

Figure 2:
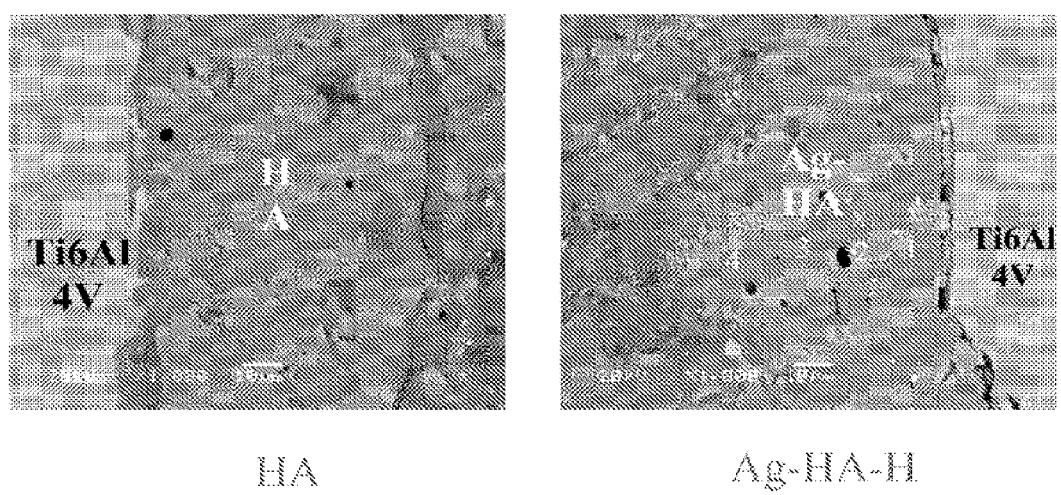
FIG. 2 is a scanning electron micrograph of cross-sectional view of HA (left) and Ag-HA-H (right)-coated Ti6Al4V discs. The silver concentration was measured at different locations throughout the coating for the Ag-HA-H sample, as indicated by the "x" markers.

Ag concentration measured by EDXA across the thickness of the coating. Positions and corresponding locations are shown in FIG. 2 for this sample.

|  | Position 1 | Position 2 | Position 3 | Position 4 |
|---|---|---|---|---|
| Average Ag Concentration (wt %) | 7.4 +/− 0.73 | 9.3 +/− 1.07 | 7.6 +/− 0.56 | 8.4 +/− 0.88 |

The XRD results are presented in Table 6. A quantitative analysis was performed using a Rietveld refinement. Besides HA phase, an impurity phase of $Ca_3(PO_4)_2CaO$ (Tetracalcium Phosphate, TTCP) was identified in all the coated samples. There was no Ag detected in the control pure HA-coated samples. The Ag content in the doped HA coatings was close to the designed Ag content shown in Table 1. The loss or evaporation of Ag during VPS process was minimal. Moreover, the addition of Ag into the HA coatings did not significantly alter the phase compositions for the Ag-HA-L and Ag-HA-M-coated samples; however, the high Ag doped HA coatings (i.e. Ag-HA-H) showed a slightly increased HA phase and decreased TTCP phase than the control pure HA-coated samples.

TABLE 6

Phase determination and composition of VPS-coated samples

| Sample | Quantitative Phase Analysis: Weight Fraction (wt %) | | |
|---|---|---|---|
|  | $Ca_{10}(PO_4)_6(OH)_2$ | $Ca_3(PO_4)_2CaO$ | Ag |
| HA | 83.9 ± 0.6% | 16.1 ± 0.5% | ND* |
| Ag-HA-L | 83.9 ± 0.8% | 15.8 ± 0.6% | 0.3 ± 0.1% |
| Ag-HA-M | 83.3 ± 0.8% | 15.6 ± 0.5% | 1.1 ± 0.2% |
| Ag-HA-H | 85.8 ± 0.9% | 11.6 ± 0.4% | 2.6 ± 0.2% |

*ND: Not Detectable

In addition, the lattice parameters and the grain size of the HA phase and the Ag phase were calculated using Scherrer's formula. These results are described in Table 7. The full width at half-maximum (FWHM) data was used along with Scherrer's formula to determine the average HA and Ag grain size. Schemer's formula is given by:

$$t = \frac{0.9\lambda}{\beta \cos\theta}$$

where $\lambda$ is the X-ray wavelength, $\beta$ is the FWHM and $\theta$ is the Bragg diffraction angle.

TABLE 7

Lattice parameters and grain size of coated samples

| | a (Å) | c (Å) | c/a ratio | V (Å³) | D (Å) HA | D (Å) Ag |
|---|---|---|---|---|---|---|
| STDHA | 9.421 | 6.884 | 0.7307 | 529.1 | — | — |
| HA | 9.4042 ± 0.0007 | 6.8992 ± 0.0005 | 0.7336 | 528.4 | 408 | — |
| HA-Ag-L | 9.3917 ± 0.0012 | 6.8914 ± 0.0009 | 0.7338 | 526.4 | 570 | 376 |
| HA-Ag-M | 9.3948 ± 0.0011 | 6.8920 ± 0.0009 | 0.7336 | 526.8 | 550 | 564 |
| HA-Ag-H | 9.3960 ± 0.0010 | 6.8904 ± 0.0008 | 0.7333 | 526.8 | 437 | 472 |

It is worth noting that all coated samples (including the Ag doped HA coatings) had a significant higher c/a ratio as compared to the stoichiometric standard HA (Table 7). This indicates the HA and Ag-HA-coated samples are non-stoichiometric which was evidenced by the Ca/P ratios shown in Table 4.

Using Scherrer's formula, the average HA grain size in the VPS coatings ranged from 40.8 nm to 57.0 nm. There was no correlation between the grain size and the content of Ag in the coatings. The average Ag grain size in the coatings was also in the nano scale, ranging from 37.6 nm to 56.4 nm. After VPS process, Ag or silver compounds were converted to nanocrystallined metallic Ag. This nanocrystalline HA phase and metallic Ag phase resulted from the fast cooling after the melted or partial melted HA or Ag-HA powders went through the plasma and rapidly deposited onto the substrate. Therefore, there was no time for the grain growth to occur.

Figure 3:
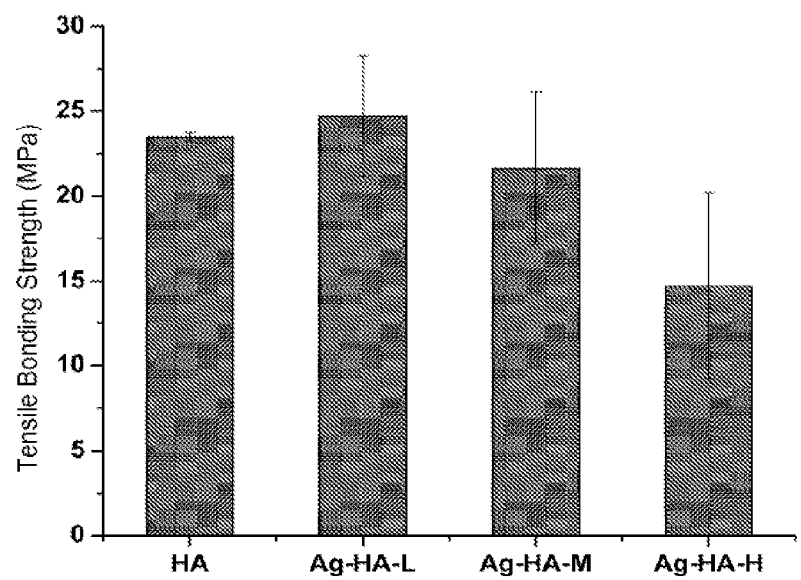
FIG. 3 shows tensile attachment strengths of different coated coupons.
Figure 4:
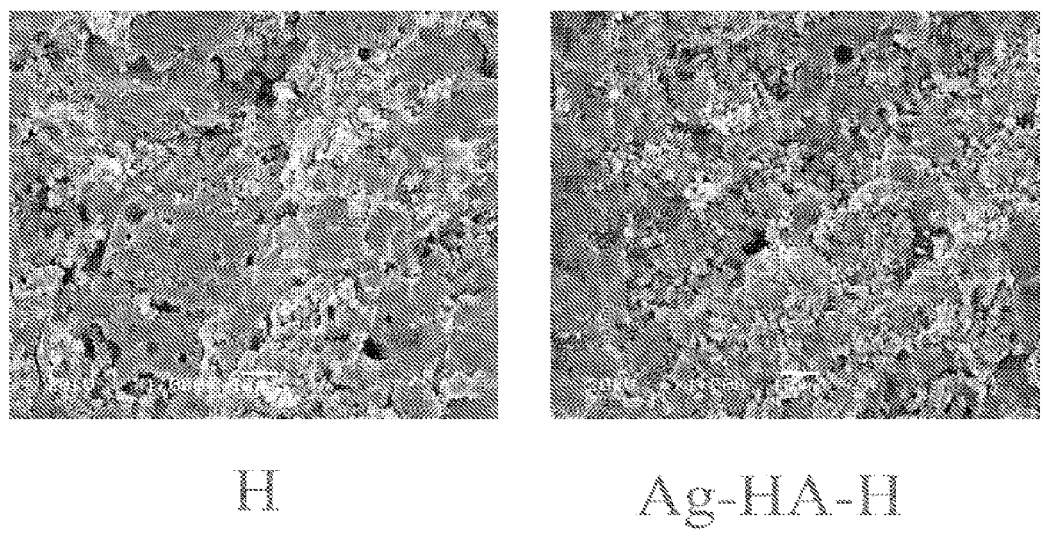
FIG. 4 shows a fracture surface of HA-coated and Ag-HA-H-coated samples.

Tensile attachment strength results are reported in FIG. 3. The tensile attachment strength for the Ag-HA-H-coated samples was the lowest among all the testing samples and did not meet the ISO requirement, which requires the minimum adhesion strength to be 15 MPa. The addition of Ag less than or equal to 1 wt % (i.e. Ag-HA-L and Ag-HA-M) did not significantly affect the tensile attachment strength of the coating. All the failures occurred within the coating. There was no obvious difference in the appearance of the fracture surfaces between the silver containing HA coatings and the pure HA coatings (pure HA and Ag-HA-H shown in FIG. 4).

Figure 5:
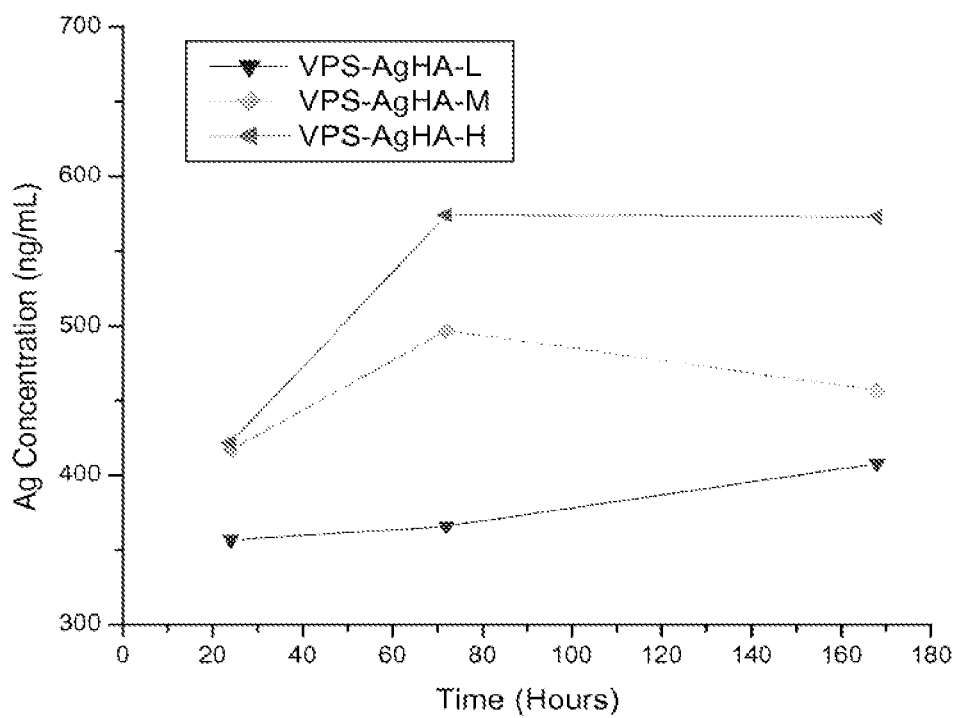
FIG. 5 shows the silver release profile in PBS of a sample.

The silver release profile in PBS is shown in FIG. 5. It shows that all coated samples released Ag into the PBS at 37° C. as early as 24 hours. The released Ag concentration in PBS increased gradually over time up to 7 days. The amount of Ag released into the PBS is Ag dosage dependent. The Ag-HA-H-coated sample released the highest amount of Ag into the PBS, and the Ag-HA-L-coated sample released the lowest amount of Ag.

Example 2

Hydroxyapatite Powder Modification Using Silver Nitrate Solution

Two different concentrations of silver nitrate solutions were prepared in distilled and de-ionized water ($DDH_2O$) for the ion exchange reaction between silver nitrate solution and HA powders. In theory, some Ag ions from the silver nitrate solution will substitute Ca ions from the HA structure, meanwhile, some Ag ions will be physically adsorbed on the HA surface. The target silver content in the HA powders was 1 wt % and 2 wt %, respectively. The mass of the silver nitrate and the HA powder was listed in Table 8.

TABLE 8

The mass of silver nitrate and HA powder used for the ion exchange reaction

| | AgNO$_3$ | HA | DDH$_2$O | Target Ag wt % |
|---|---|---|---|---|
| HA | — | 250 g | — | 0 |
| Ag-HA1 | 4.0 g | 250 g | 1500 mL | 1.0 |
| Ag-HA2 | 8.0 g | 250 g | 3000 mL | 2.0 |

Silver nitrate (BDH, Cat.#BDH0276-125G) was first dissolved in DDH$_2$O contained within a 3 liter glass beaker, and then the HA powders (MEDIPURE®, MEDICOAT AG, particle size: −130 μm+45 μm) were added into the prepared silver nitrate solution according to Table 8. The HA and silver nitrate solution was stirred at 180 RPM in an orbital shaker at room temperature for 3 days to allow a homogeneous ion exchange reaction.

After the ion exchange reaction, the solution was left to dry at 80° C. in an oven to evaporate the water. The dried and modified HA powders were then slightly ground using an automated pestle and mortar (Retsch, Mortar Grinder RM200, Newtown, Pa.) to break the agglomerates formed during the drying process. The ground modified HA powders were then sieved through 100-325 mesh sieve (W.S. Tyler, Inc., USA). Any HA powders that were larger than 150 μm or smaller than 45 m were discarded. At least 98% HA powders were collected between 100-325 mesh sieves.

The silver modified HA powders were further characterized using a Laser Diffraction Particle Size Analyzer (Model LS 13 320, Beckman Coulter, USA). All the measurements were listed in Table 9. The average particle size was slightly increased with the increase of the silver content in the HA powders. The particle size distribution of the low and medium silver HA powders were similar to the control pure HA powders.

TABLE 9

Particle size and size distribution of pure HA and modified HA powders

| | Mean (μm) | D10 (μm) | D25 (μm) | D50 (μm) | D75 (μm) | D90 (μm) |
|---|---|---|---|---|---|---|
| HA | 92.24 ± 2.02 | 57.81 | 79.17 | 106.4 | 132.8 | 155.1 |
| Ag-HA1 | 101.6 ± 1.66 | 65.93 | 85.80 | 111.1 | 136.5 | 157.2 |
| Ag-HA2 | 96.34 ± 1.61 | 58.85 | 78.52 | 105.0 | 131.5 | 153.1 |

These silver modified HA powders were then used in a conventional vacuum plasma spray process at Medicoat (Magenwil, Switzerland) for the silver containing HA coatings.

Substrate Preparation

All substrates were made from mill-annealed Ti6Al4V alloy. The flat-surfaced disc samples were 12.6 mm in diameter and 3.1 mm in thickness. These coupons were grit blasted and cleaned at S&N in Aarau, Switzerland.

Coating Deposition

The coating was applied using the conventional vacuum plasma spray system at Medicoat in Magenwil, Switzerland. All the spray parameters were the same for both pure HA powders and the silver modified HA powders. A stainless steel plate with Φ12.6 mm holes was used to mount Ti6Al4V coupons. After the coating process, the as-sprayed coatings were rinsed with isopropanol.

Coating Characterization Techniques

Field Emission Scanning Electron Microscopy

The samples were examined using a FEI Nova NanoSEM 200 Scanning Electron Microscope (SEM) equipped with a dual backscatter detector (Dual BSD) and an EDAX Genesis 4000 Energy Dispersive X-ray microanalysis (EDX) system according to SOP/MS/131. All three examples of each sample coupon were mounted on a 25 mm diameter aluminium pin stub by means of self adhesive carbon rich discs. The samples were examined uncoated (no sputter coating) using low vacuum conditions (0.6-1.0 Torr, water vapour) at a moderate accelerating voltage of 10 KV to minimize surface charging and to maximise surface information (minimised electron beam penetration).

The analytical conditions used to obtain EDX data were a 10 KV accelerating voltage, spot size 5.5, with the final aperture in position 3 and X-ray count rates of between approximately 1500 and 4000 counts per second at 20% to 39% detection system dead-time (approximately optimal conditions). EDX microanalysis was carried out at 10 KV accelerating voltage, because this provides the minimum electron beam energy required to excite x-rays from the chemical elements of interest to this study, whilst attempting to minimise penetration of the sample past the surface of the material. High resolution imaging was achieved with a Low Vacuum Detector (LVD) for secondary electrons and a Gaseous Analytical Detector (GAD) for backscattered electrons. Digital images of representative areas were recorded in uncompressed TIFF format. Image Pro Plus software was used to estimate the size of silver rich material in samples HA1-Ag/HA (TO035B) and HA2-Ag/HA (TO035C), using the SEM image scale bar to provide a spatial calibration.

X-ray Diffraction

X-ray Diffraction (XRD) was utilized to characterize the structure and phase compositions. This analysis was performed at Swiss Federal Laboratories for Materials Testing and Research in Switzerland. The XRD patterns were measured between 20° and 60° at a step size of 0.02° with a copper x-ray source. The signal was measured for 3 seconds at each step and the intensity is given in counts per second (cps). The following slits and filters were used in the following order 1 mm, 0.5 mm, Ni filter, and 0.2 mm. The XRD was measured on the as sprayed coating rather than the powder scrapped from the surface (as stated in the ISO 13779-3). The XRD patterns of the hydroxyapatite coatings were analysed by a modified version of the ASTM F 2024-00 and the ISO 13779-3 standards. The direct application of both standard test methods were not applicable because of the presents of the silver obscured the results. The reasons for the modification of the standards and the methods used to analysis the coatings were discussed in the results section. The reference materials were hydroxyapatite (HAref76/800/7 h), Al$_2$O$_3$ (Alpha Aesar 99.99%) and a silver plate (99.95%).

Tensile Attachment Strength of Coatings to Ti6Al4V Substrate

Five one-inch diameter Ti6Al4V coupons from each of three groups were used as substrates to deposit HA or Ag doped HA coatings to assess the tensile attachment strength of the coatings in a manner similar to that described in ASTM F 1147.

The back-side of each coupon and the ends of the testing stubs were all lightly sanded with 80-grit paper to enhance epoxy attachment strength. The back-side of the coupons (i.e. no-coated surface) was cleaned with acetone and allowed to air-dry for 2-3 minutes.

Tensile testing stubs were glued to the opposing surfaces of each coupon using one layer of FM1000 adhesive on the back surface and one layer on the coating surface. This was done by assembling the constructs in a curing fixture and placing the fixture in a convection oven for 130 minutes (or 135 minutes if two fixtures were put in the oven simultaneously) at a temperature of 338° F. (170° C.) under a dead weight load of 2.3 lbf (10 N) to thermal cure the glue. After removing the fixture from the oven and allowing it to cool to room temperature, the dead weights were removed and the constructs were taken out of the fixture.

Each construct was tested by subjecting it to a tensile load at a displacement rate of 0.10 in/min (2.5 mm/min) until failure. The peak load and failure mode for each construct was recorded. The tensile attachment strength was determined by dividing the peak load by the cross-sectional area of the coupon. After testing, each coupon was inspected to ensure that glue did not penetrate to the substrate, which would indicate an invalid test.

Results and Discussion

SEM/EDX

Figure 6:
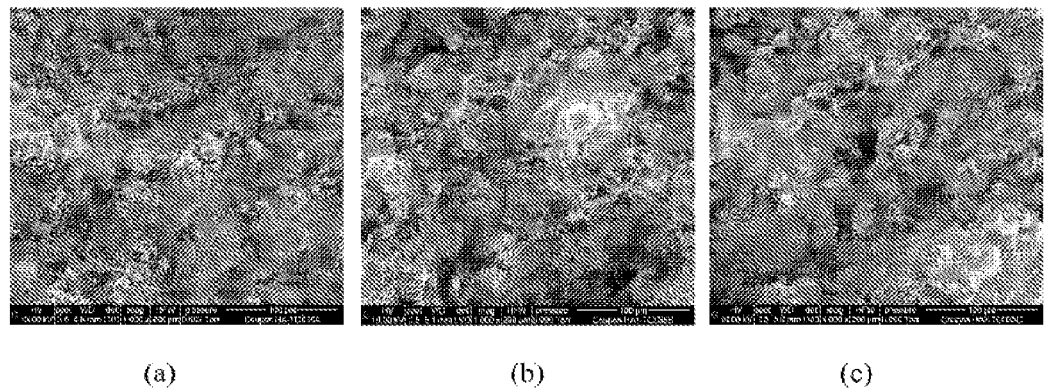
FIGS. 6a (HA) 6b (Ag-HA1) and 6c (Ag-HA2), shows secondary electron images of each different sample at low magnification, providing an overview of each sample type.

FIG. 6a to FIG. 6c, shows secondary electron images of each different sample at low magnification, providing an overview of each sample type. No qualitative differences can be seen in the surface appearance of each sample type. The surfaces had a mixture of rounded, amorphous morphologies, with some areas of aggregated, angular particulates suggestive of incomplete melting of the powder stock used in the coating process. This is consistent with the use of a melt sprayed deposition process such as vacuum plasma deposition, to coat the metal coupons.

Figure 7:
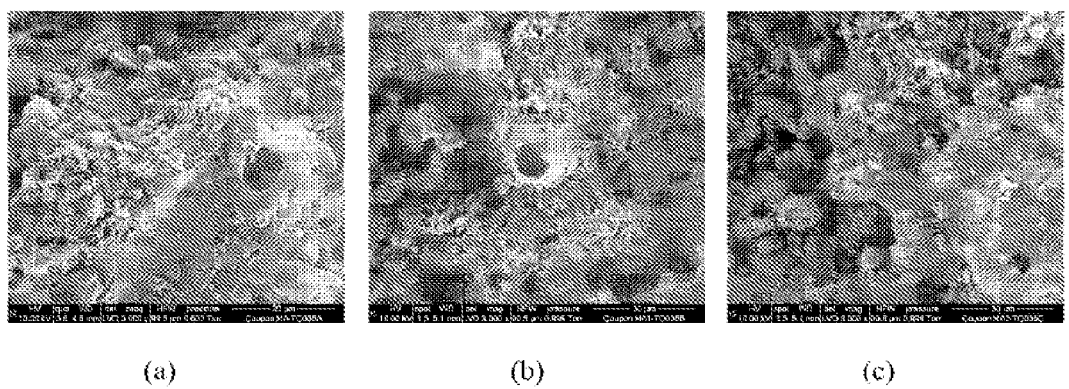
FIGS. 7a (HA), 7b (Ag-HA1) and 7c (Ag-HA2) show higher magnification secondary electron images of the surface morphology of the samples of FIG. 6.

FIG. 7a to FIG. 7c show higher magnification secondary electron images of the surface morphology of each sample. A mixture of morphologies can be seen on each sample, with both amorphous-like material and some fine, angular particulates being present. Microscopic cracks were present on the surface of the HA layer (evident in FIG. 7c). Similar particulate material was observed on all of the samples and there were no apparent qualitative differences in their surface appearance regardless of sample type or magnification, although backscattered electron signals in both secondary and backscatter detector images revealed the additional presence of micro and nano-scale silver particles in samples Ag-HA1 and Ag-HA2.

Figure 8:
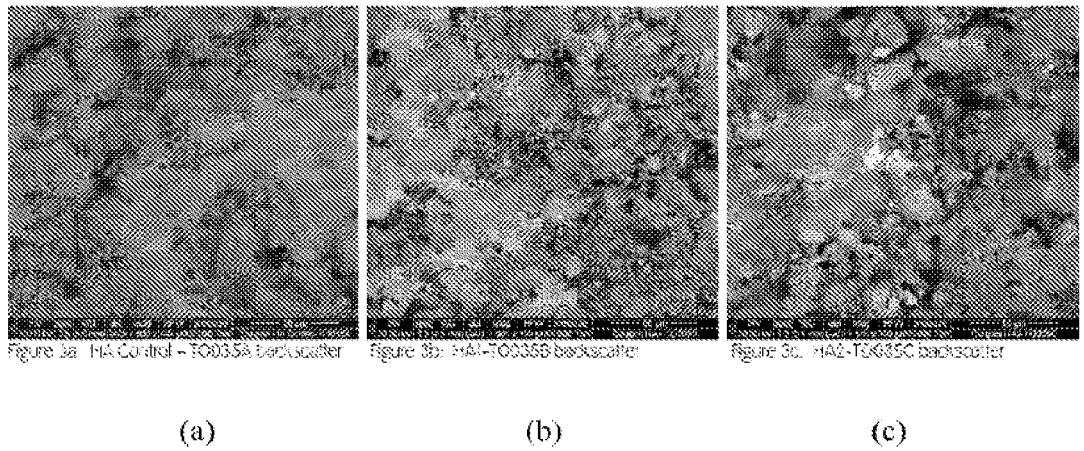
FIGS. 8a (HA), 8b (Ag-HA1) and 8c (Ag-HA2) show backscattered electron images of different samples at low magnification, providing an overview of each sample type.

FIG. 8a to FIG. 8c, show backscattered electron images of each different sample at low magnification, providing an overview of each sample type. Several bright speckles/particles can be seen on the silver-containing samples. More electrons are backscattered from materials composed of higher average Atomic Number (Z), creating bright areas on backscattered electron images. The brighter and very bright areas in FIGS. 8b and 8c correspond to the locations of material rich in silver (silver compounds have a higher average Z than calcium HA, represented as darker areas in backscattered electron images). Higher magnification backscatter images are shown from each sample in FIGS. 9a to 9c, revealing fine detail in the spatial distribution of silver-rich material in the silver-containing samples.

Figure 9:
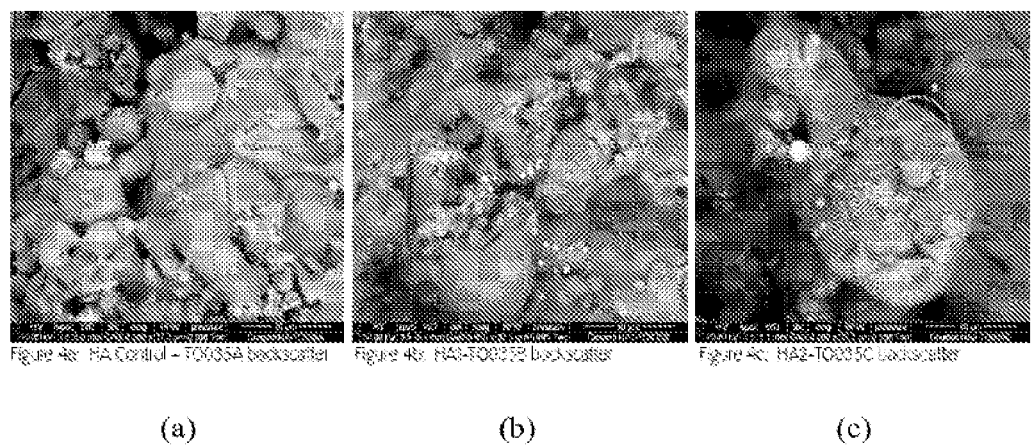
FIGS. 9a (HA), 9b (Ag-HA1) and 9c (Ag-HA2) show higher magnification backscatter images are shown from each of the samples in FIG. 8.
Figure 10:
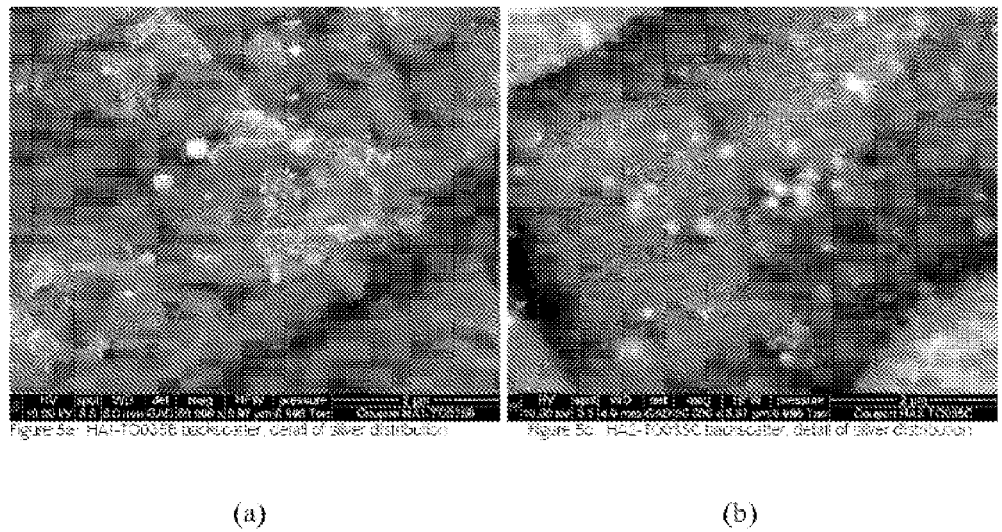
FIGS. 10a (Ag-HA1) and 10b (Ag-HA2) and FIGS. 11a (Ag-HA1) and 11b (Ag-HA2) show higher magnification examination of samples of FIGS. 8 and 9.
Figure 11:
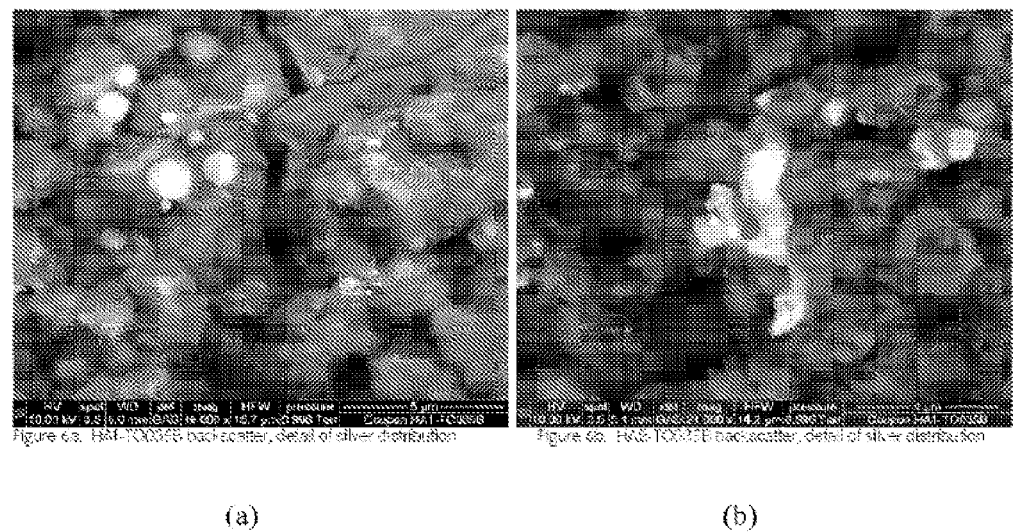
Figure 12:
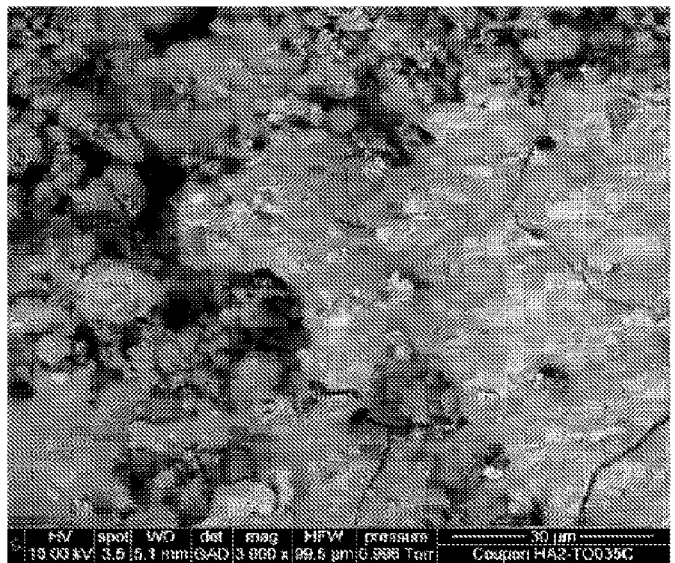
FIG. 12 is a backscatter EM of a sample of the present invention.

The composition of the HA Control sample is homogeneous as visualised by backscattered electrons (FIG. 9a). Samples Ag-HA1 and Ag-HA2 containing silver are shown to be heterogeneous in terms of composition in FIGS. 9b and 9c. A range of different sizes of silver-rich material can be seen, with more silver-rich material present in sample Ag-HA2. Image analysis estimates of the sizes of the silver-rich material ranged between approximately 15 nm and 10 μm for the silver-containing samples. Higher magnification examination highlights the different shapes of the silver-based particulates, FIGS. 10a and 10b and FIGS. 11a and 11b. Light grey areas on each sample (such as circled in orange in FIG. 9c and clearly visible in FIG. 12) are shown to be composed of many nanoscale silver particulates dispersed at or under the surface of the calcium HA when viewed at high magnification.

Figure 13:
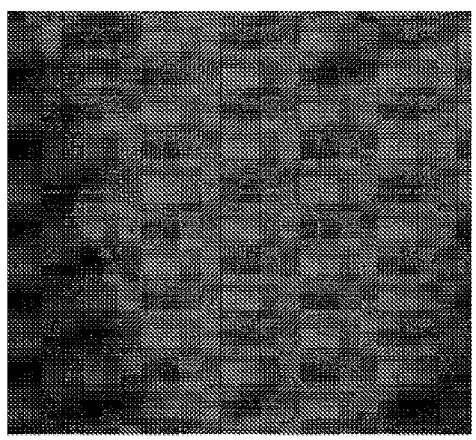
FIG. 13a shows an elemental dot-map obtained by EDX microanalysis, while a backscatter image of the corresponding area of sample Ag-HA2 is shown in FIG. 13b.
Figure 13:
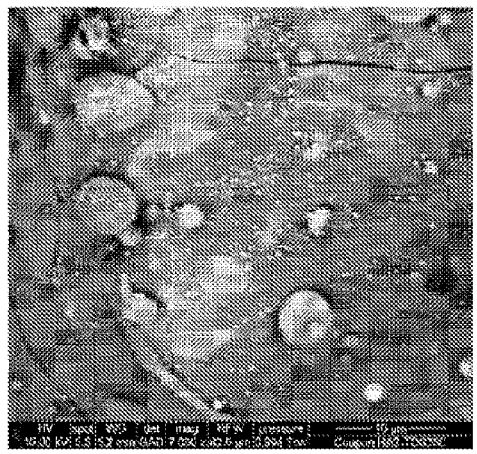

FIG. 13a shows an elemental dot-map obtained by EDX microanalysis, while a backscatter image of the corresponding area of sample Ag-HA2 is shown in FIG. 13b. The dot-map provides confirmation that the bright features and the light grey features shown in backscatter images of the silver doped sample correspond to silver-rich material (blue areas of EDX map).

Figure 14:
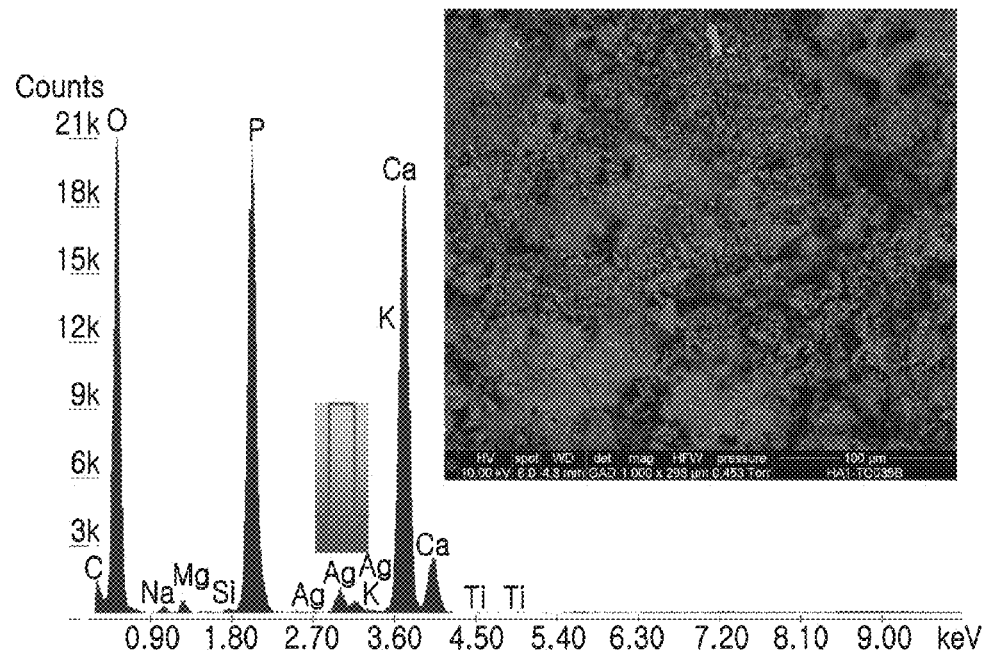
FIGS. 14a (Ag-HA1) and 14b (Ag-HA2) shows the EDS spectra from Ag-HA1 sample and Ag-HA2 sample.
Figure 14:
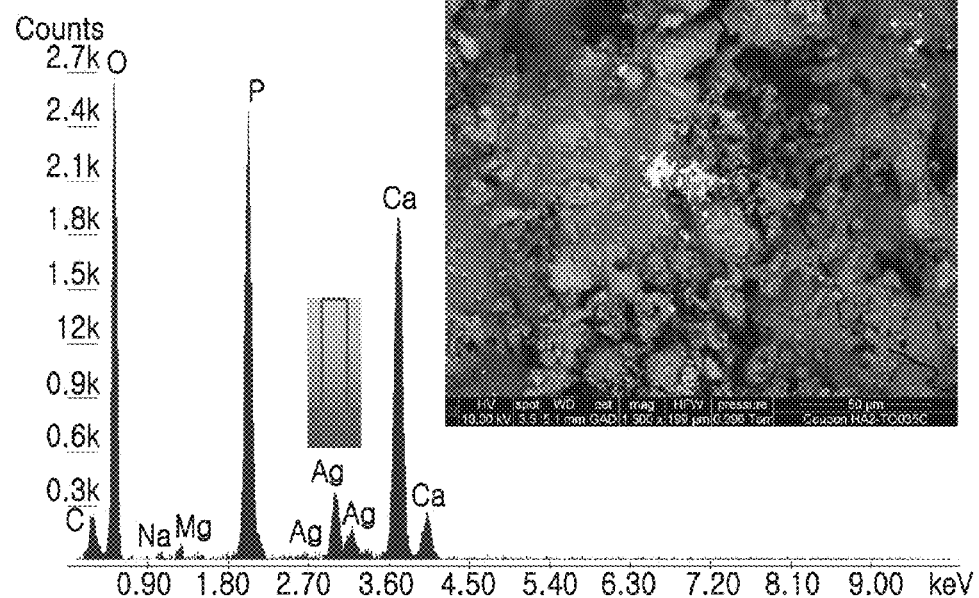

FIGS. 14a-b show the EDS spectra from Ag-HA1 sample and Ag-HA2 sample. The arrow indicates silver peak energies. It showed Ag-HA2 had higher Ag content in the coating.

Figure 15:
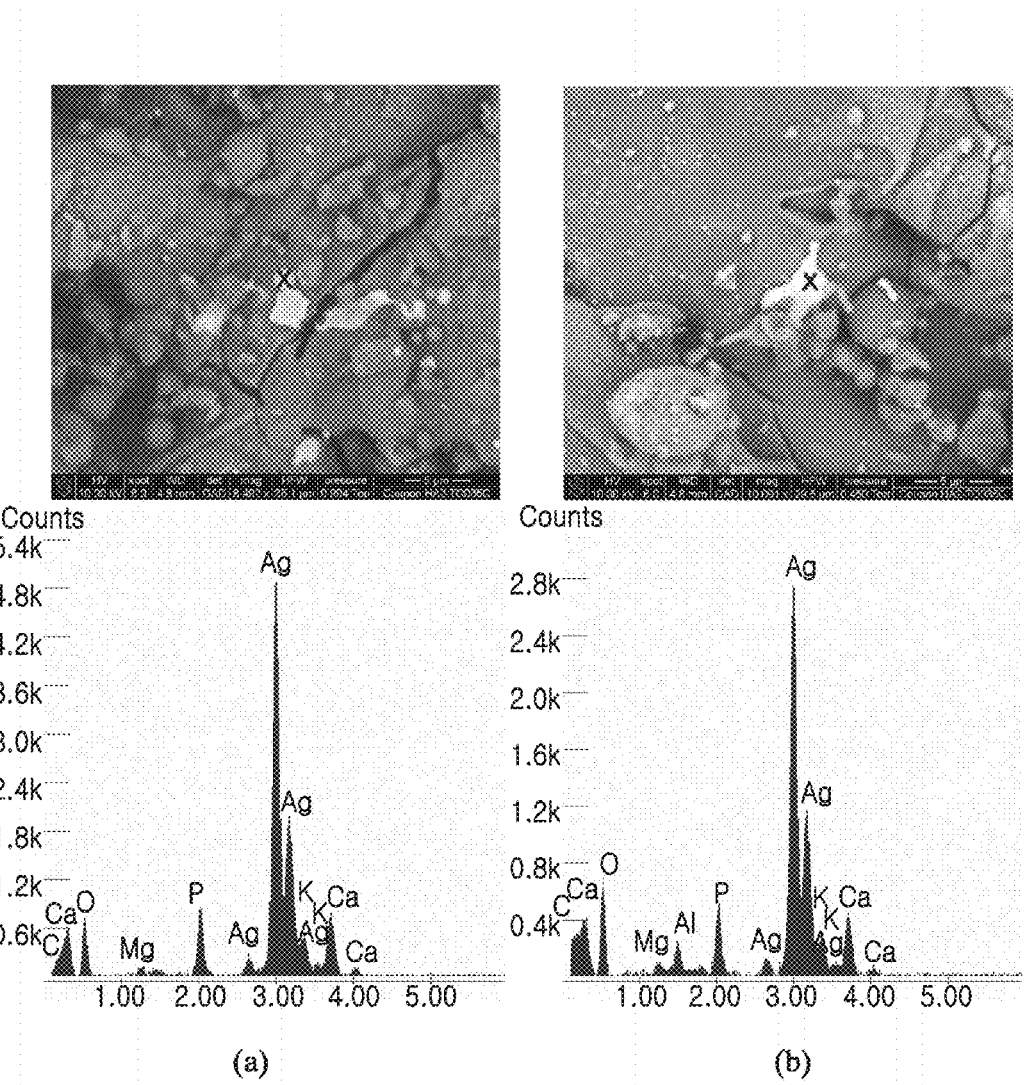
FIGS. 15a and 15b show the EDX spectra of discrete bright particles on HA2 samples (spots marked with "x" in images).

FIGS. 15a-b show the EDX spectra of discrete bright particles on HA2 samples (spots marked with "x" in images). The silver concentrations in these areas were much higher than that of areas without discrete bright particles, as shown in the below images. These bright regions and the attendant EDXA spectra confirm the presence of metallic particles, previously discovered via XRD analyses.

Figure 16:
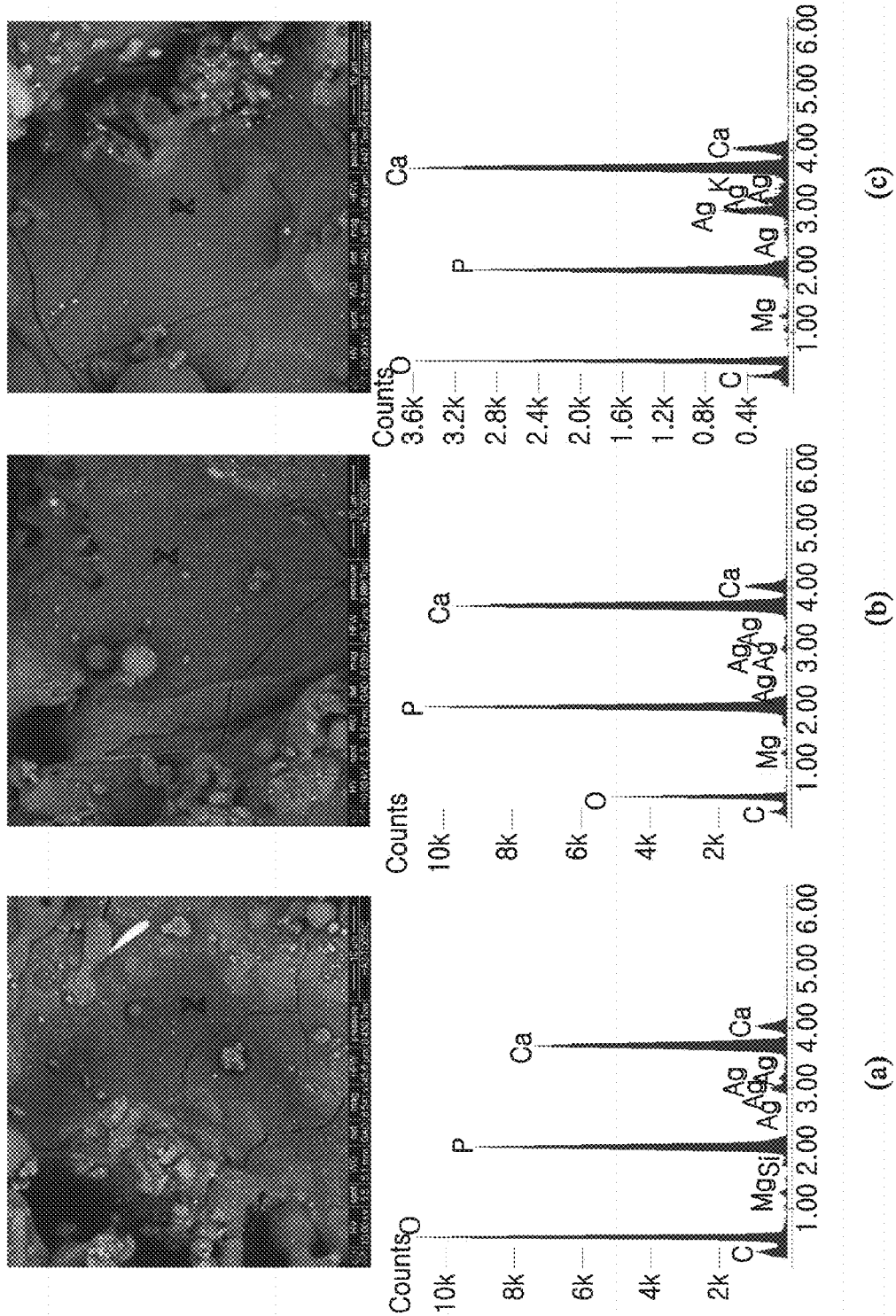
FIGS. 16a-c is an image of the areas of the coating away from discrete bright particles that were also evaluated via EDXA on HA2 samples.

The areas of the coating away from discrete bright particles were also evaluated via EDXA on HA2 samples, as shown in FIGS. 16a-c. These areas, devoid of bright discrete particles, also showed presence of silver, albeit at a much lower concentration. This confirms the presence of silver substitution within the HA matrix, as was demonstrated previously by XRD and ICP analyses.

X-ray Diffraction

Qualitative Analysis.

Figure 17:
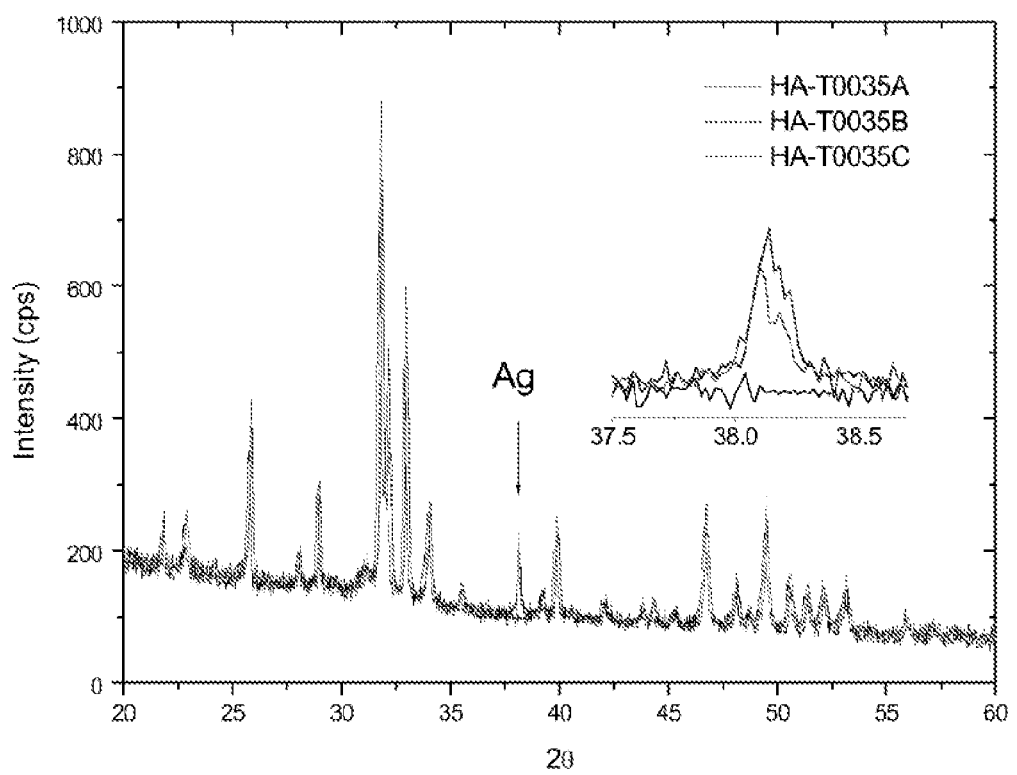
FIG. 17 shows the X-Ray Diffraction pattern of the three samples, HA, Ag-HA1, and Ag-HA2.

The XRD patterns for the three samples are given in FIG. 17. Sample HA shows all the expected peaks for hydroxyapatite. The Ag-HA1 and Ag-HA2 samples show the same HA peaks but with the addition of a peak at 38.15° (arrow indicating the peak in FIG. 17) that is consistent with metallic silver. A broad peak is observed at 31.1°. This peak could be attributed to the amorphous phase or alpha Tricalcium Phosphate ($\alpha$-TCP) or beta Tricalcium ($\beta$-TCP). The peak at 38.15° is the diffraction from silver (Ag) and the insert shows a zoomed in image of this peak.

3.3.2 Crystallinity Analysis

The crystallinity was measured by both the ASTM F 2024-00 and ISO 13779-3 standards. The results for both methods are presented in Table 10. The ASTM F2024-00 measures the relative intensity of the peaks between 38.5° and 59° compared to an external standard ($\alpha$-$Al_2O_3$). These peaks are not convoluted by the common impurities found in hydroxyapatite, but the relative intensities of these peaks are lower then the major peaks and therefore this method is less sensitive. The ISO 13779-3 standard measures relative intensity of the 10 most intense peaks compared to a 100% hydroxyapatite reference. These measurements were conducted on the 'as sprayed' samples, opposed to the powder scraped from the surface (as specified in ISO 13779-3).

3.3.3 Silver Analysis

The silver content of the two samples Ag-HA1 and Ag-HA2 were measured by relative intensity compared to a pure silver sample. The results for the silver content are given in Table 10. The Ag-HA1 samples have a silver content of 2.0±0.5% and the Ag-HA2 samples have a silver content of 2.5±0.5%.

TABLE 10

The Crystallinity, β-TCP, and Silver content

| | Crystallinity | | β-TCP | Ag(%) |
|---|---|---|---|---|
| | ISO 13779-3 | ASTM F2024-00 | ASTM F2024-00 | Relative Intensity |
| HA | 53 ± 1% | 52 ± 1% | 4 ± 0.5% | — |
| Ag-HA1 | 68 ± 1% | 58 ± 1% | <1% | 2.0 ± 0.5% |
| Ag-HA2 | 58 ± 1% | 53 ± 1% | 4 ± 0.5% | 2.5 ± 0.5% |

3.5 Tensile Attachment Strength of Coatings to Ti6Al4V Substrate

Figure 18:
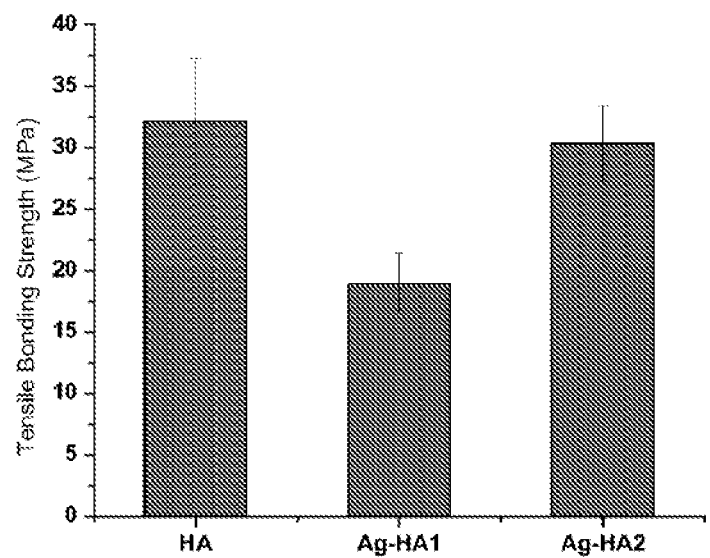
FIG. 18 shows the tensile bonding strength of the three different samples.

Tensile attachment strength results are reported in FIG. 18. The tensile attachment strength for the Ag-HA1-coated samples was the lowest among all the testing samples, but even the lowest value of this group still meets the ISO requirement, which requires the minimum adhesion strength to be 15 MPa. All the failures occurred within the coating. There was no obvious difference in the appearance of the fracture surfaces between the silver containing HA coatings and the pure HA coatings.

Example 3

Gradient Coatings for Biomedical Applications

Figure 19:
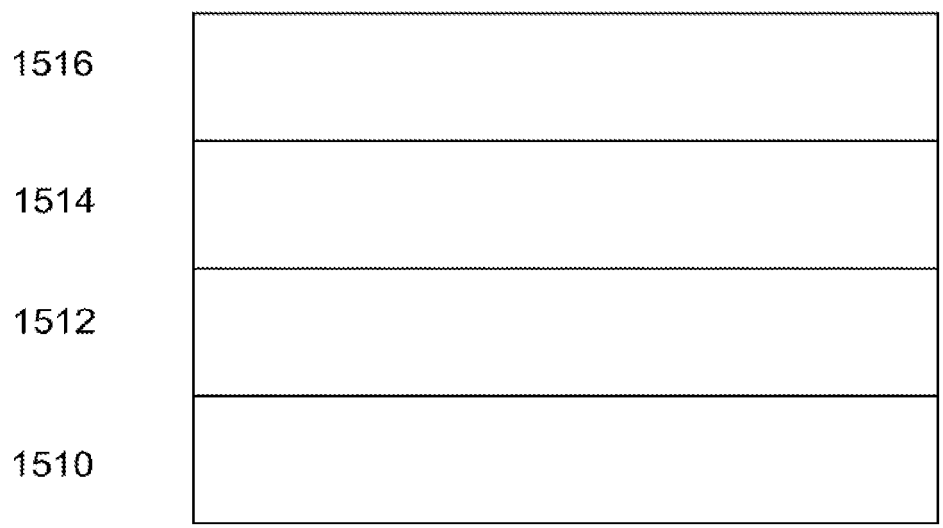
FIG. 19 is a schematic of an embodiment of a coating of the present invention.

FIG. 19 shows an example of an embodiment of the present invention (an implant substrate (1510) [e.g. Ti6Al4V] with a gradient coating containing VPS HA (1512) and VPS AgHA (1514). and a top layer of PLGA coating contains β-TCP, Ag, and Bupivacaine (1516)) prepared by the following method:

1. HA/Ag-HA Coating Preparation:

The Ag-HA powders (45-125 μm) were modified using an ion exchange reaction. The coating process parameters were the same as the standard vacuum plasma sprayed HA coatings produced at our manufacturing facility for medical implants. VPS HA coating was first applied and then followed by the VPS Ag-HA coating. The coated sample was ready for the PLGA coating.

2. Silver Modified β-TCP Powder Preparation:

1). 0.5 g β-TCP powder ($D_{50}$~3 μm) and 145.8 mg silver nitrate were dissolved into 55 mL de-ionized and distilled water and stirred for 1 hour at 60° C.
2). The water was evaporated overnight at 60° C.
3). The dry powder was then ground. Alternatively, the silver modified β-TCP can also be freeze dried to remove the water and the grinding step is not necessary.
4). The silver modified powder was subsequently sintered at 400° C. for 2 hours.

3. PLGA Solution Preparation:

1). 0.75 g PLGA pellets (85:15) were dissolved in 15 mL of dichloromethane and stirred overnight.
2). The 0.25 g silver modified β-TCP and 100 mg Bupivacaine powder were dissolved into the PLGA solution and stirred overnight.Asdasd 4. PLGA Coating Application:

The VPS HA/VPS Ag-HA coated Ti6Al4V substrate was dipped into the PLGA solution and withdrawn vertically and then dry in air overnight.

Figure 20:
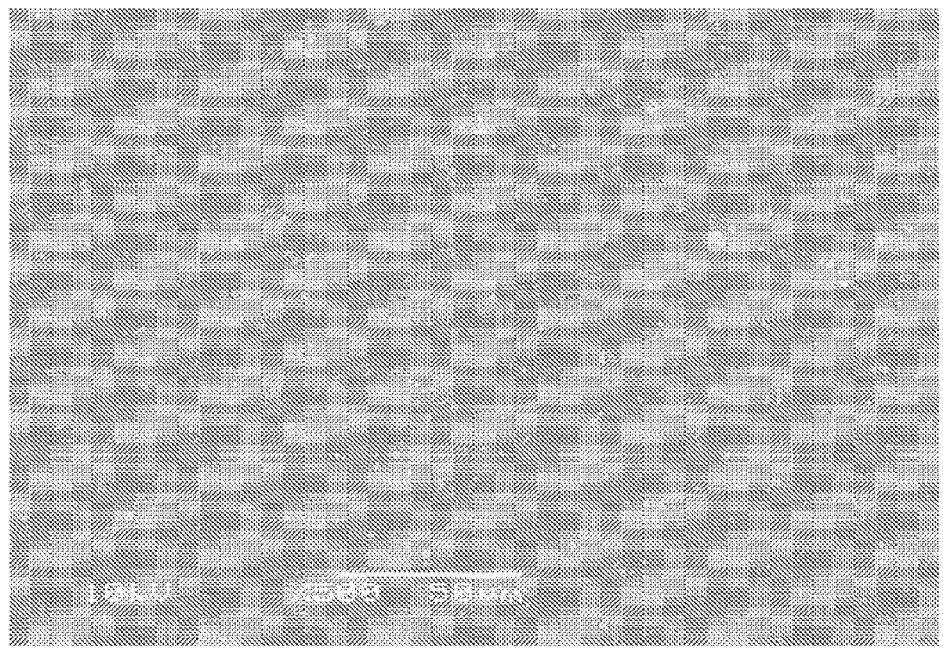
FIG. 20 is a low magnification of the top PLGA coating containing silver modified beta-TCP and Bupivacaine.
Figure 21:
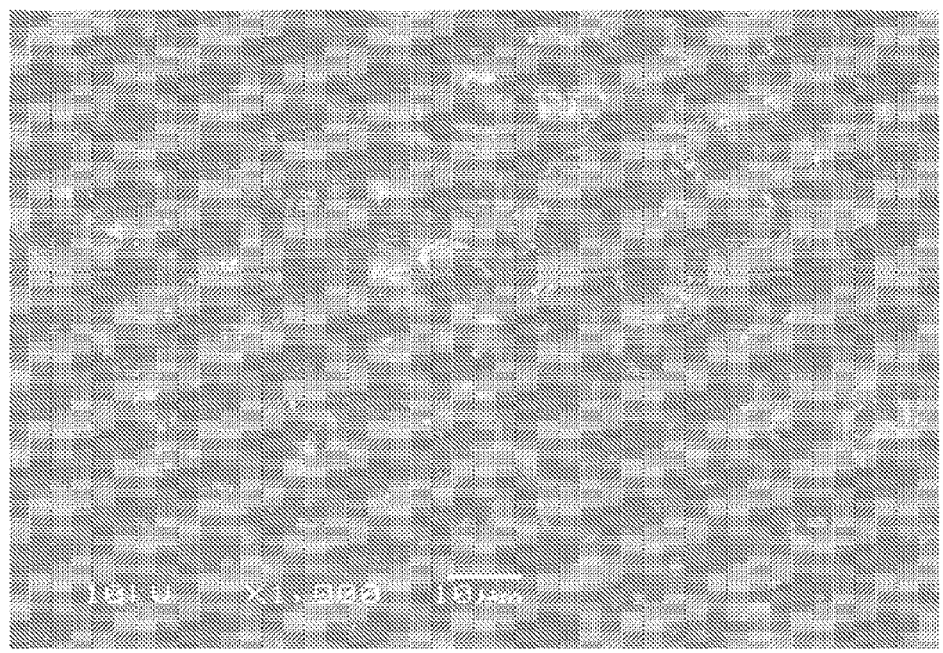
FIG. 21 is a high magnification of the top PLGA coating containing silver modified beta-TCP and Bupivacaine.

Results:

The surface morphology of the top PLGA layer is shown in FIGS. 20 and 21. A quantitative analysis obtained from an EDXA spectrum is shown in Table 11.

TABLE 11

EDXA result of the top PLGA coating

| Element | Wt % |
|---|---|
| CK | 65.23 |
| OK | 26.17 |
| PK | 3.09 |
| AgL | 1.04 |
| CaK | 4.48 |

Example 4

Figure 22:
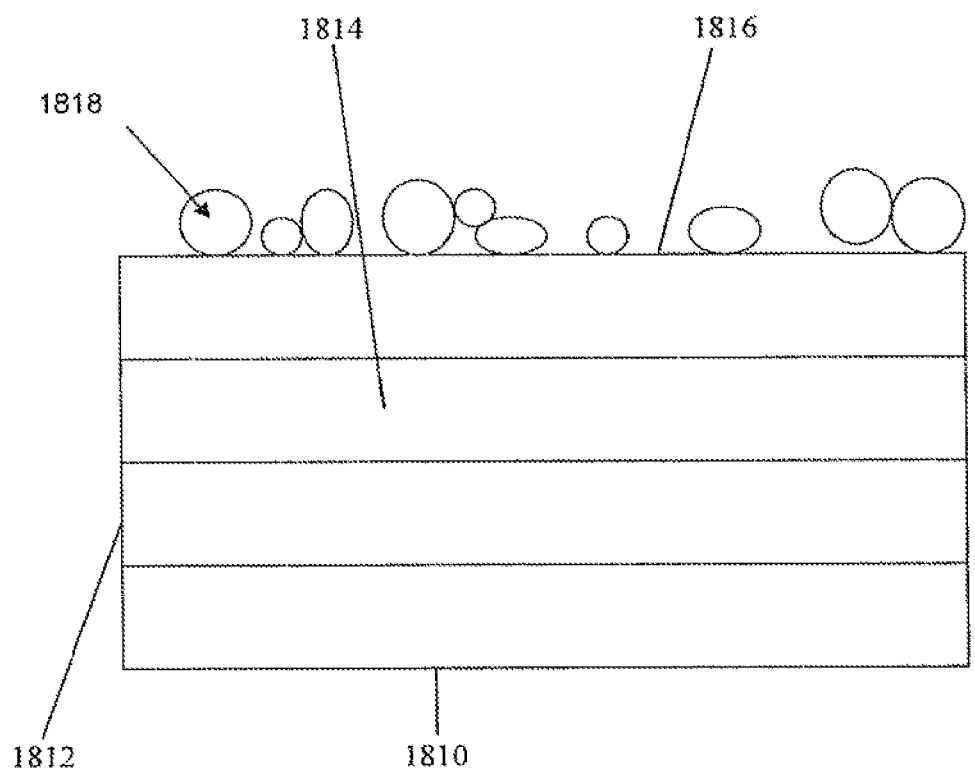
FIG. 22 is a schematic of another embodiment of the present invention.

FIG. 22 shows another embodiment of the present invention (an implant substrate (1810) [e.g. Ti6Al4V] with a gradient coating containing VPS HA (1812) and VPS AgHA (1814), and a layer of PLGA coating contains β-TCP, Ag, and Bupivacaine (1816), and a PLGA beads layer containing β-TCP, Ag, and Bupivacaine (1818)).

This is an example to demonstrate that the amount and release duration of Ag and Bupivacaine can be controlled by increasing the total coating surface area through adding PLGA beads on the top surface of the PLGA coating. Bupivacaine was known to have a quick release profile in the body environment. In order to have a continuous prolonged release, Bupivacaine was incorporated into the PLGA beads to slow down its degradation rate in the body environment.

Method

1. PLGA Beads Preparation:

1) The silver modified β-TCP powder was prepared in the same way as in the Example 3.
2) The 0.25 g silver modified β-TCP and 100 mg Bupivacaine powder were dissolved into the PLGA solution (0.75 g PLGA in 15 mL dichloromethane) and stirred overnight.
3) 5 g Sodium Dodecyl Sulfate (SDS) was dissolved into 500 mL de-ionized and distilled water.
4) The PLGA solution containing the silver modified β-TCP and Bupivacaine powder was added into the SDS solution drop by drop with a vigorous stir. The beads formed from the water-oil-water double emulsification were washed and collected after 24 hours stirring in the 1% SDS.
5) The collected PLGA beads were applied onto the top PLGA coating which also contains silver modified β-TCP and Bupivacaine.
6) The PLGA beads were sintered together and to the PLGA coating at 70° C. for 12 hours.

Figure 23:
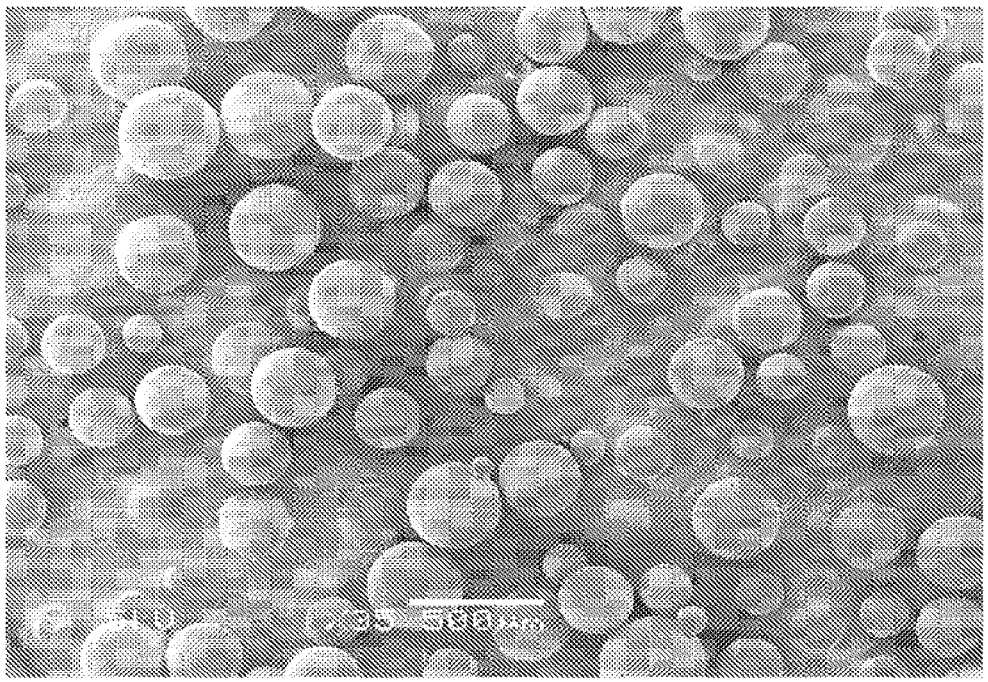
FIG. 23 is a low magnification of the top view of the PLGA beads on a PLGA coating.
Figure 24:
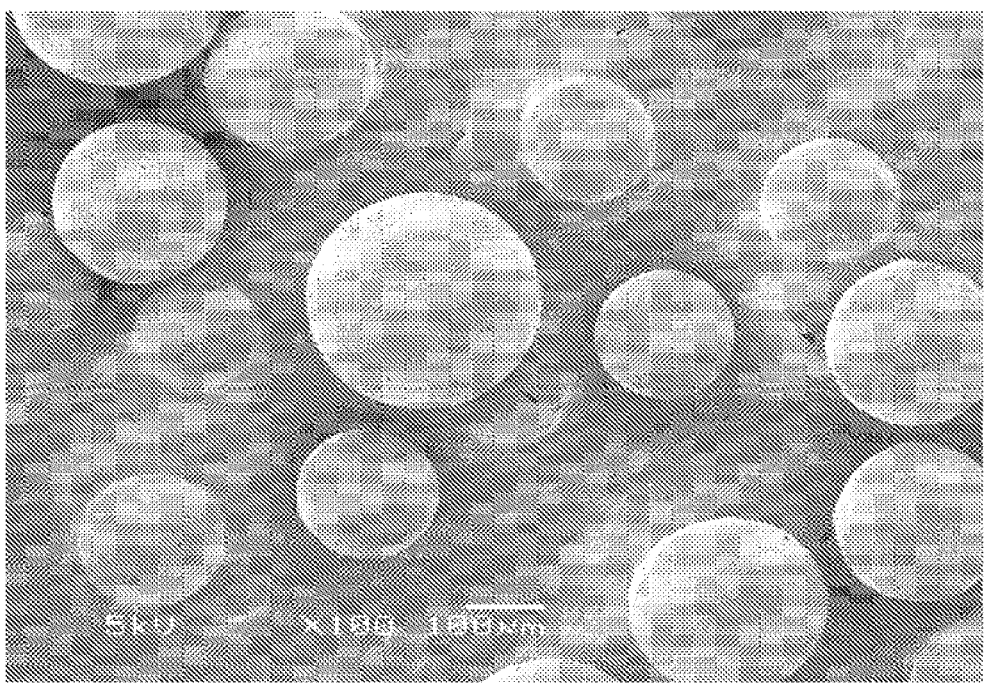
FIG. 24 is a high magnification of the top view of the PLGA beads on a PLGA coating.
Figure 25:
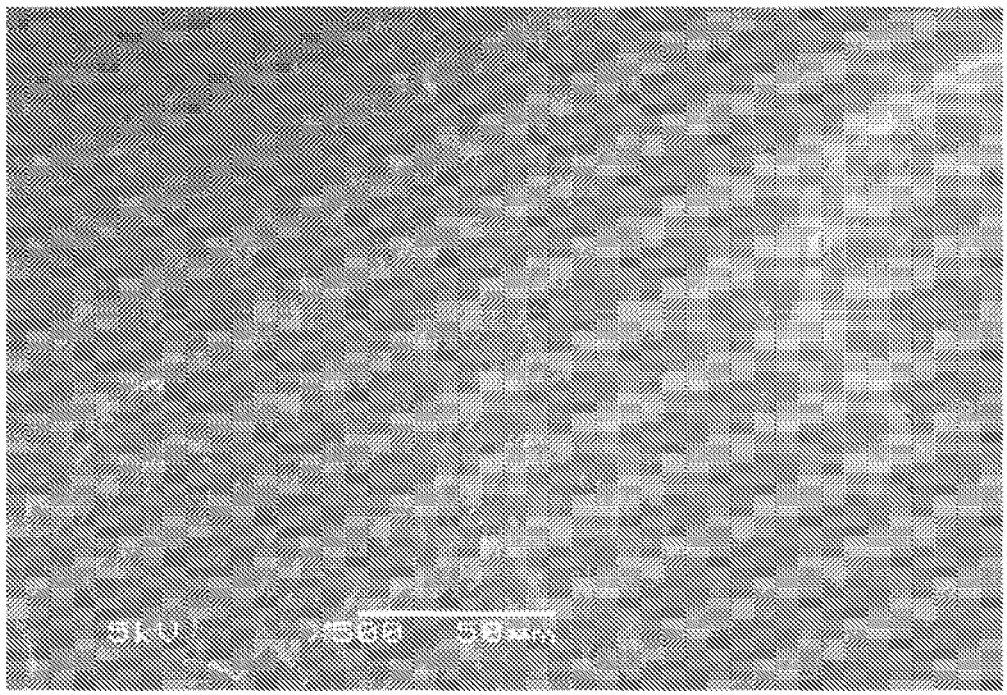
FIG. 25 is a high magnification of the PLGA coating.
Figure 26:
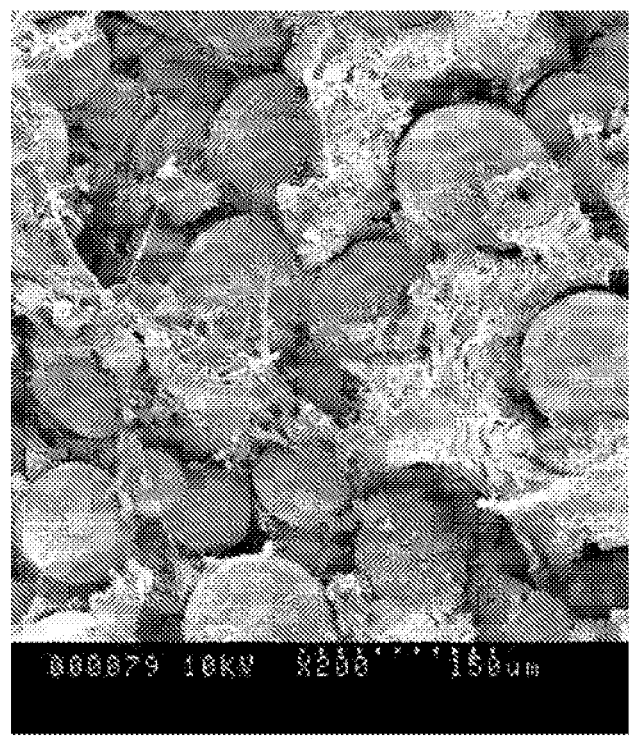
FIGS. 26 (*a*) and (*b*) are SEM images from 9-day pulled out implant: Low Ag-modified calcium phosphate-coated implant from Rabbit #1A.
Figure 26:
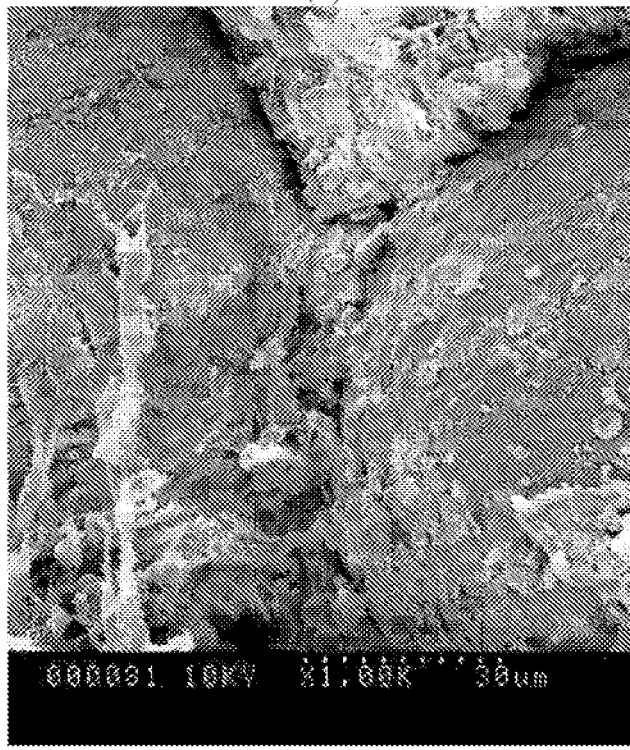
Figure 27:
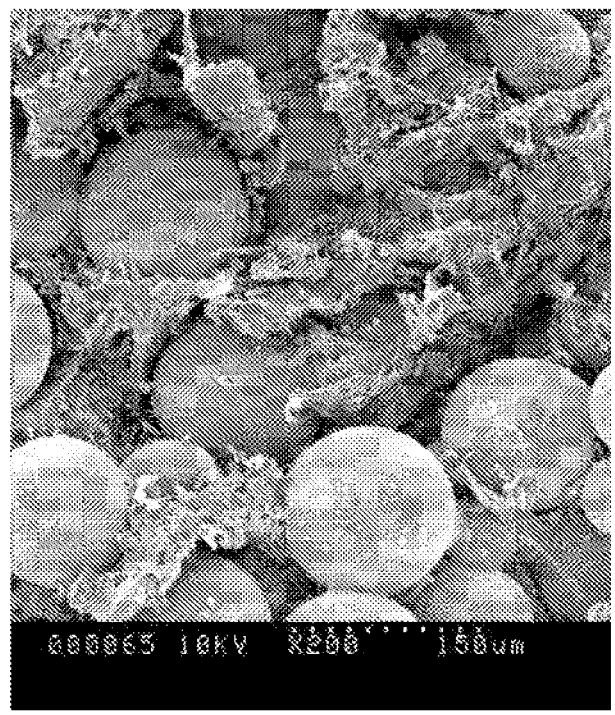
FIGS. 27 (*a*) and (*b*) are SEM images from 9-day pulled out implant: non-calcium phosphate-coated implant from Rabbit #1A.
Figure 27:
Figure 28:
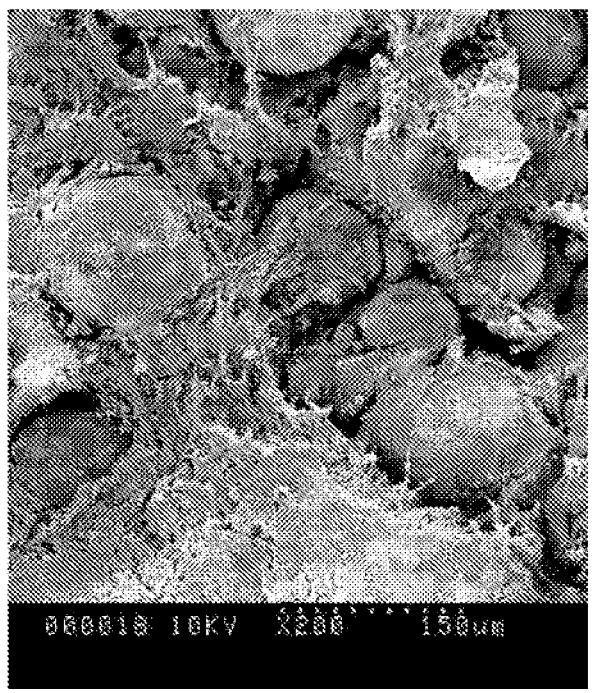
FIGS. 28 (*a*) and (*b*) are SEM images from 9-day pulled out implant: High Ag-modified calcium phosphate-coated implant from Rabbit #1B.
Figure 28:
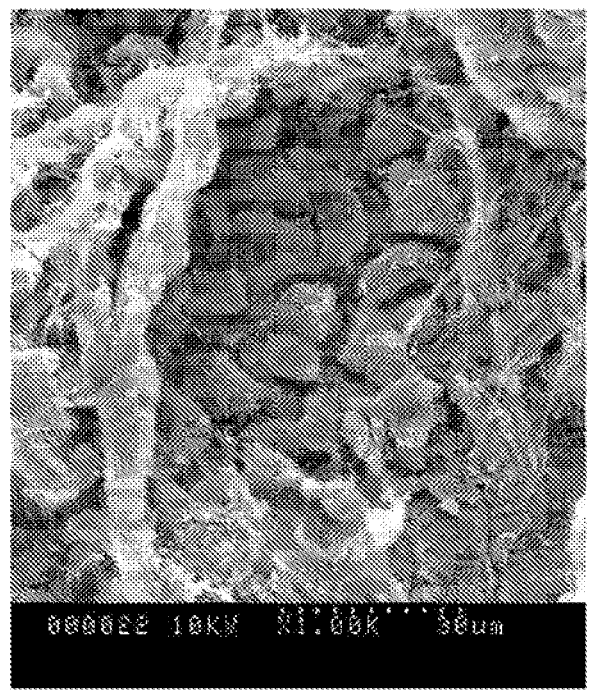
Figure 29:
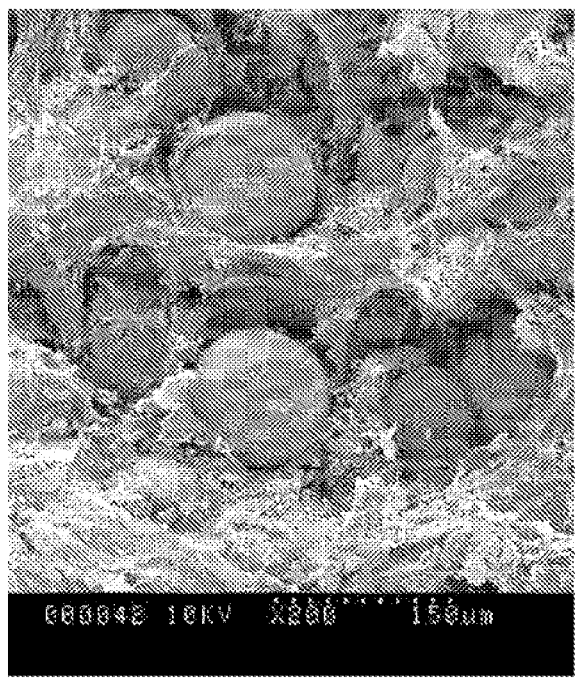
FIGS. 29 (*a*) and (*b*) are SEM images from 9-day pulled out implant: non-calcium phosphate-coated implant from Rabbit #1B.
Figure 29:
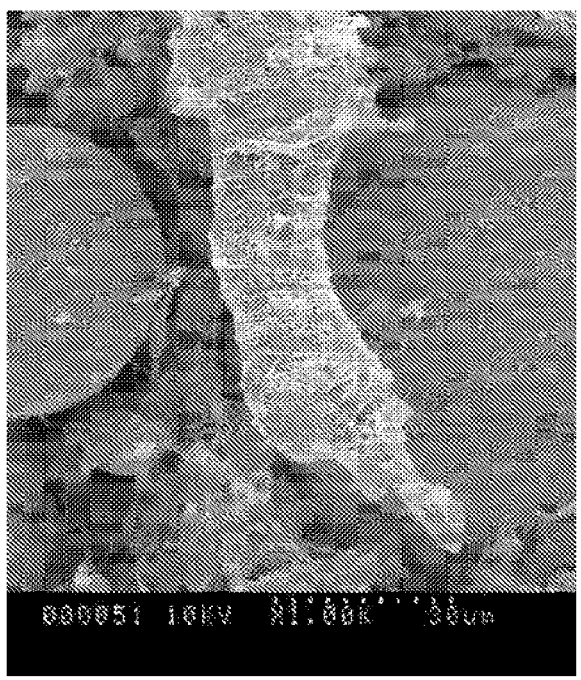
Figure 30:
FIG. 30 is a back-scattering SEM of a 'low' S-CP, 9 days. (Sample 4A Right). Small regions of mineralized tissue (bone) (arrows) within regions of the porous coat. Dashed lines shows the position of host bone after site drilling.
Figure 31:
FIG. 31 is a back-scattering SEM of a 'high' S-CP, 9 days. (Sample 5B Left). Small regions of mineralized tissue (bone) (arrows) within regions of the porous coat. Dashed lines shows the position of host bone after site drilling.
Figure 32:
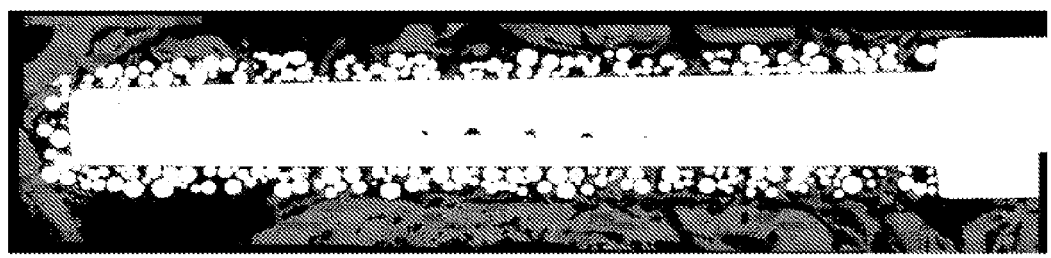
FIG. 32 is a back-scattering SEM of a 'control' (no CP), 9 days. (Sample 5B Right). Small regions of mineralized tissue (bone) (arrows) within regions of the porous coat.
Figure 33:
FIG. 33 is a back-scattering SEM of a 'low' S-CP, 16 days. (Sample 9C Right). Extensive bone ingrowth throughout full porous coat depth. Dashed lines shows initial drilled bone border.
Figure 34:
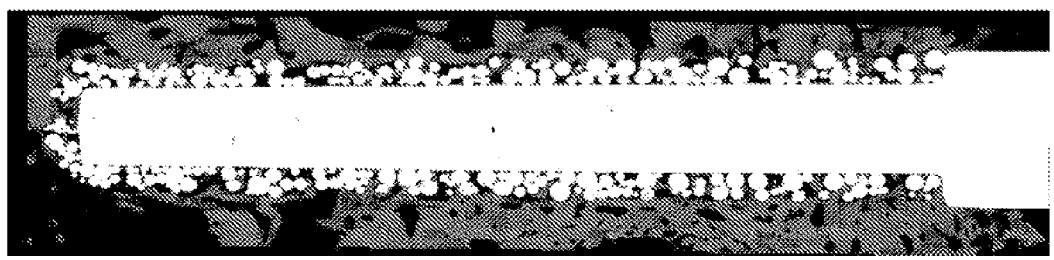
FIG. 34 is a back-scattering SEM of a 'high' S-CP, 16 days. (Sample 8D Right). Extensive bone ingrowth throughout full porous coat depth. Dashed lines show probable initial drilled bone border.
Figure 35:
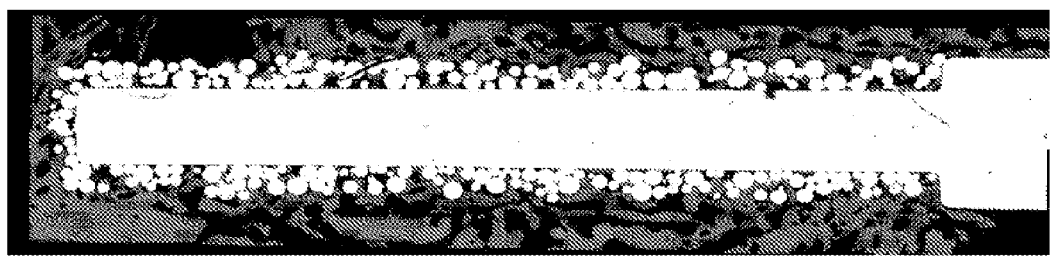
FIG. 35 is a back-scattering SEM of a 'control' (no CP), 16 days. (Sample 2C Left). Bone ingrowth throughout depth of porous coating; difficult to identify initial drilled bone border.
Figure 36:
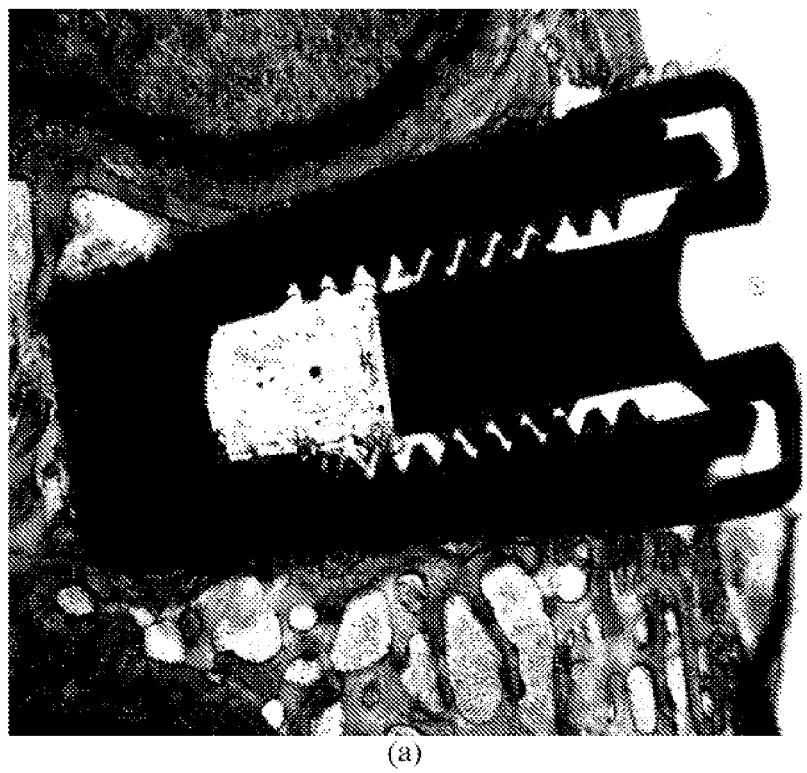
FIGS. 36 (*a*) and (*b*) show a 9-day sintered porous-coated Ti6Al4V 'control' implant—(a) and (b) Sample 5B Right—the blue-green stained areas are bone (old and newly-formed). Due to the section thickness, some bone does not show the staining effect and appears grey. A small amount of fibrous tissue is present near the interface in some regions (arrow).
Figure 36:
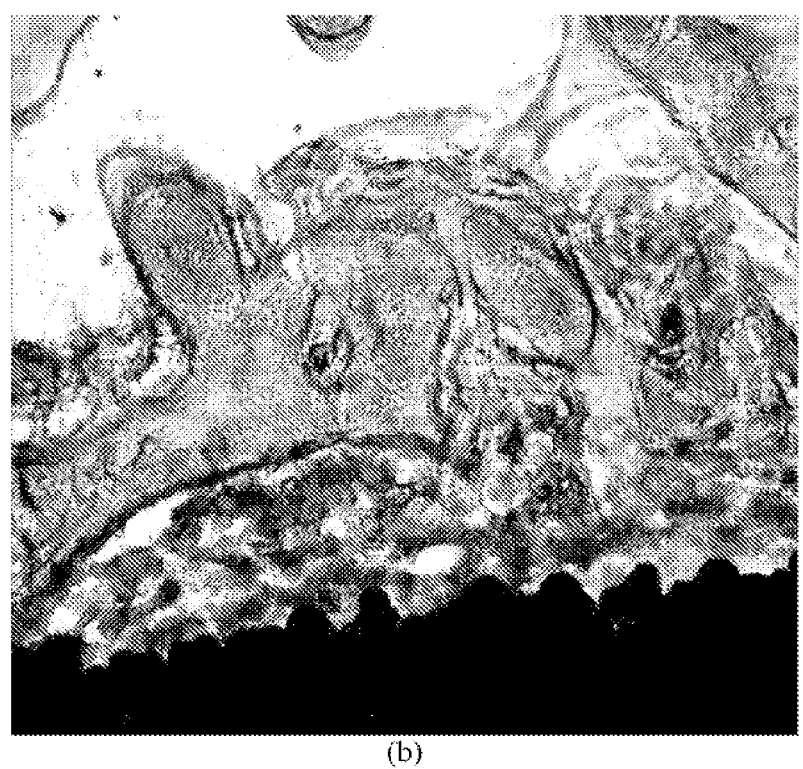
Figure 37:
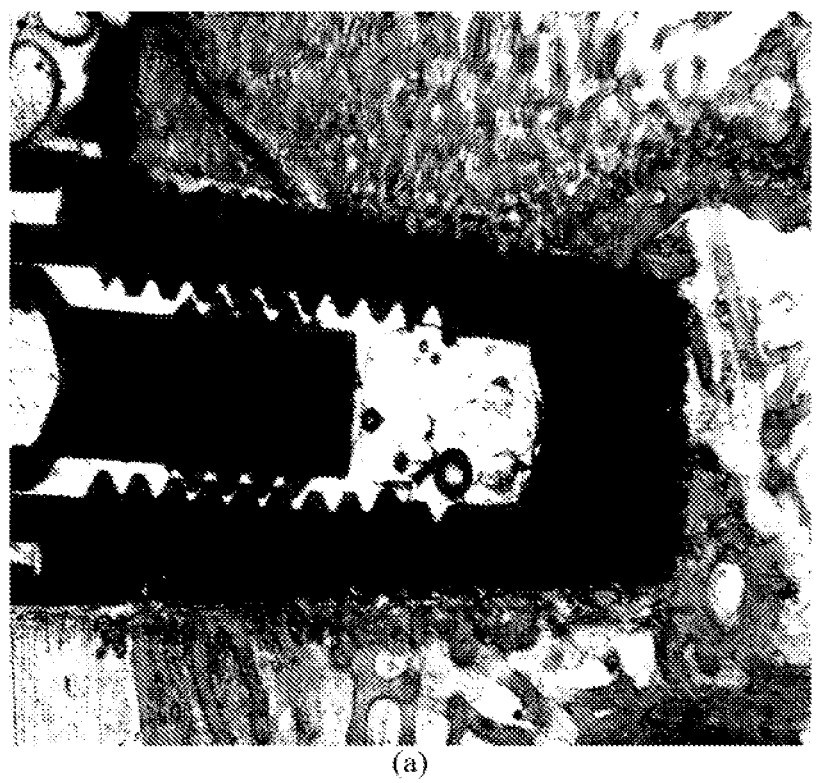
FIGS. 37 (*a*) and (*b*) show the 9-day sintered porous-coated Ti6Al4V implant with 'low' S-CP over-layer—(a) Sample 8A Left, (b) sample 4A Right—In (b), the extent of original bone loss due to drilling (and possibly some bone die-back) is evident by the truncated trabeculae.
Figure 37:
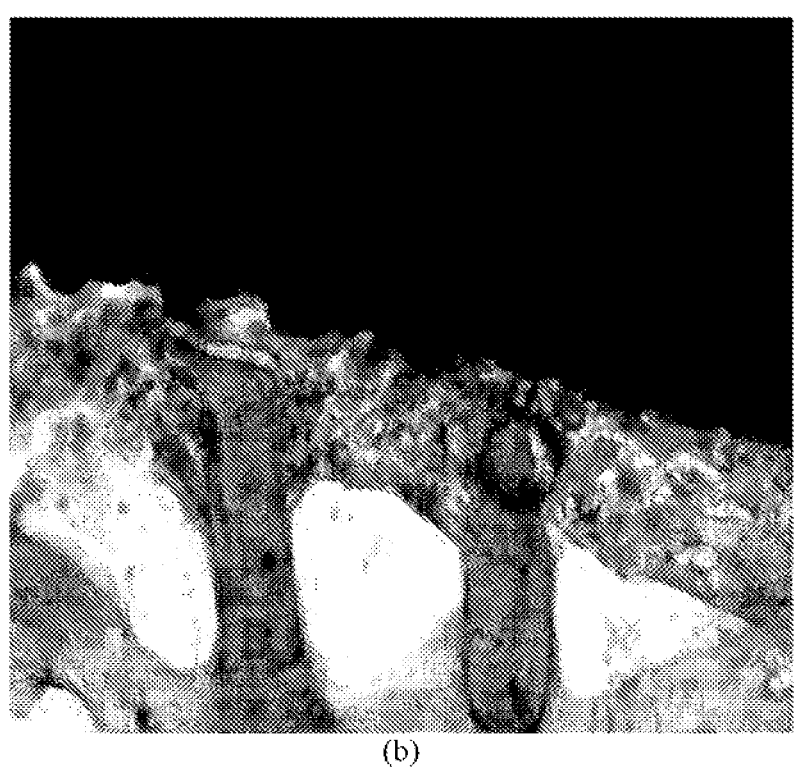
Figure 38:
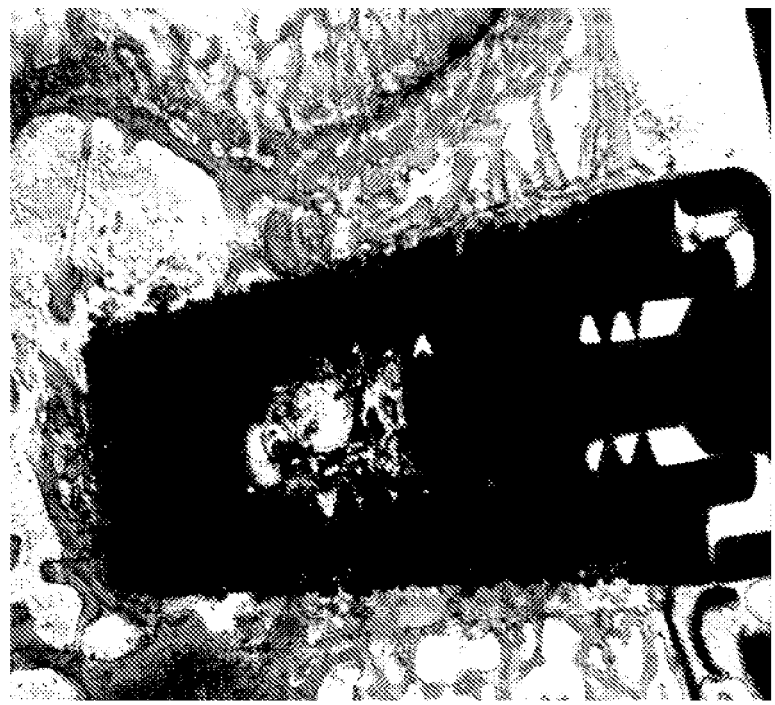
FIGS. 38 (*a*) and (*b*) show the 9-day sintered porous-coated Ti6Al4V implant with 'High' S-CP over-layer—(a) & (b) Sample 8B Left—Both the high and low magnification images show the extent of bone loss due to site preparation (drilling) and possibly subsequent bone die-back (dashed line in (b). Nevertheless, a suitable press-fit was achieved allowing early bone formation within the interface zone and into the porous coat (arrow).
Figure 38:
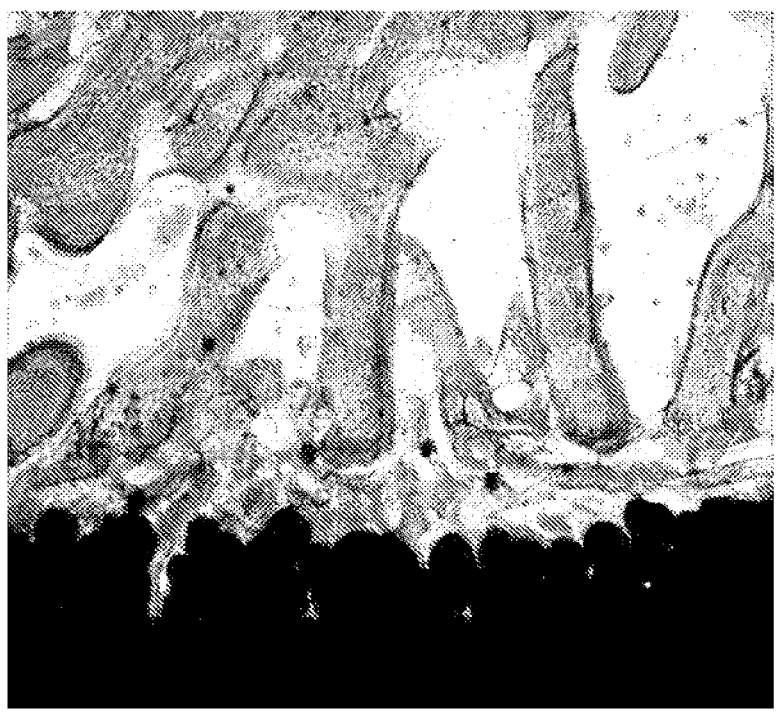
Figure 39:
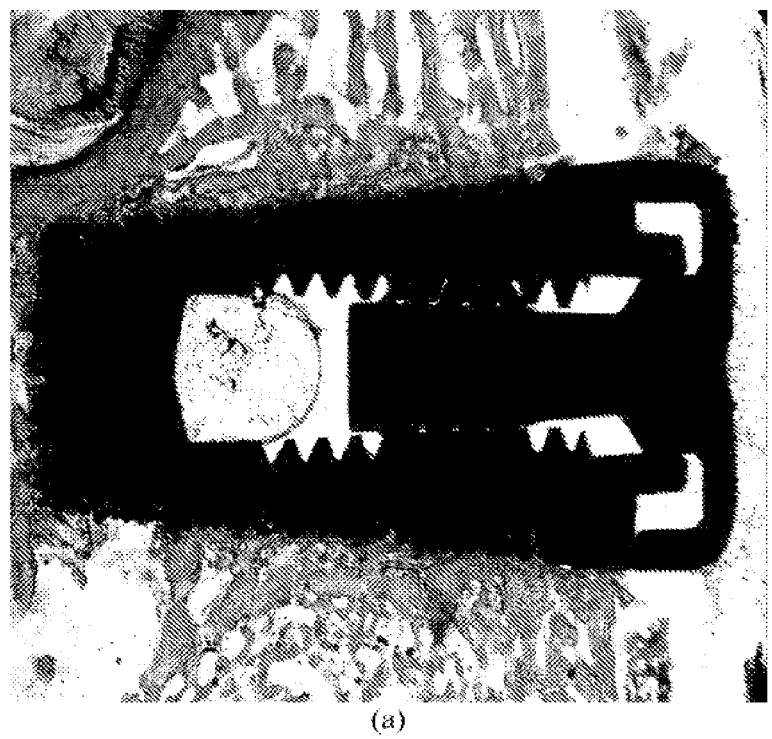
FIGS. 39 (*a*) and (*b*) show the 16-day sintered porous-coated Ti6Al4V implant 'control' implant—(a) & (b) Sample 2C Left—Extensive new bone formation and ingrowth throughout the porous coat (blue-green stained areas).
Figure 39:
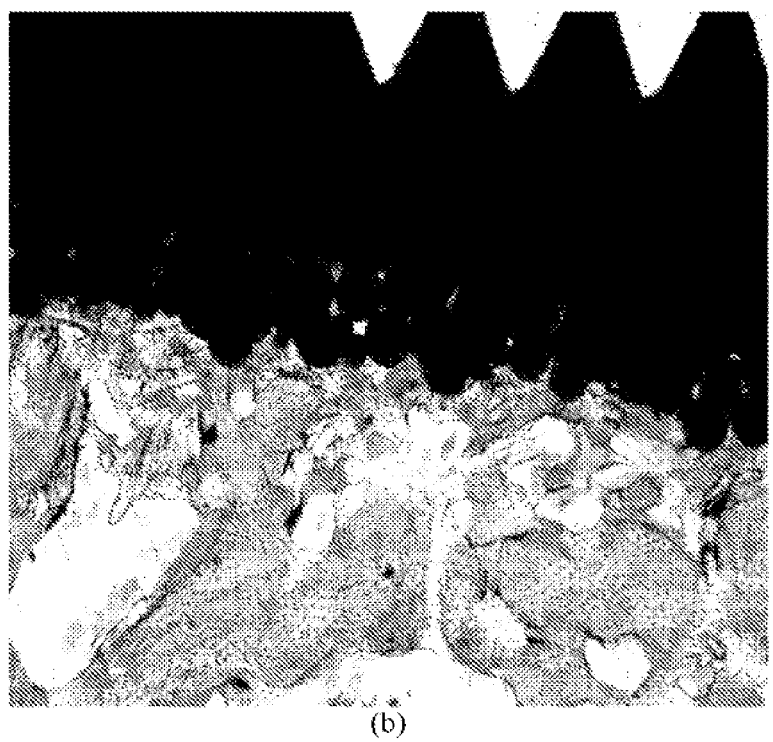
Figure 40:
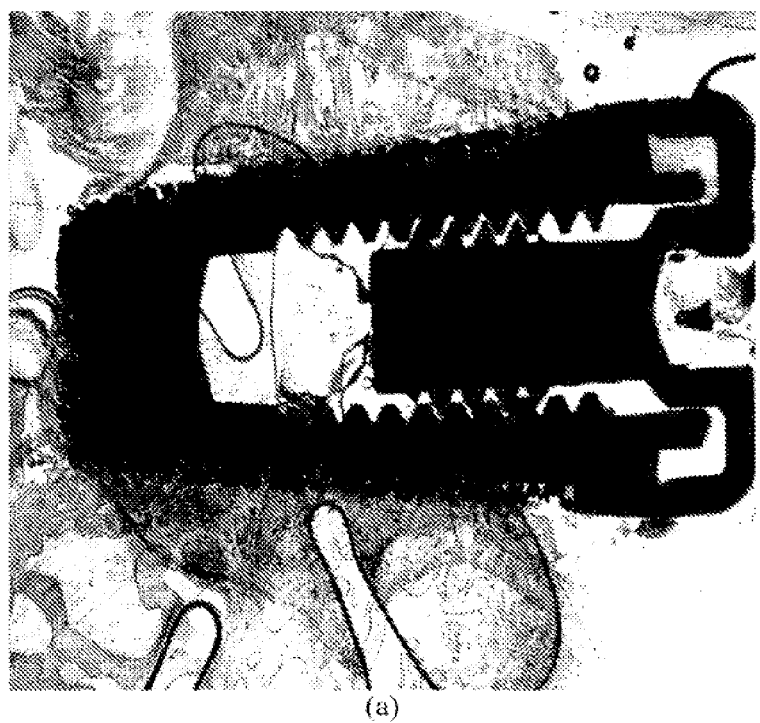
FIGS. 40 (*a*) and (*b*) show the 16-day sintered porous-coated Ti6Al4V implant with 'Low' S-CP over-layer—(a) & (b) Sample 9C Right—Extensive new bone formation and ingrowth. [Sample embedding artifacts (air bubbles) seen in (a)].
Figure 40:
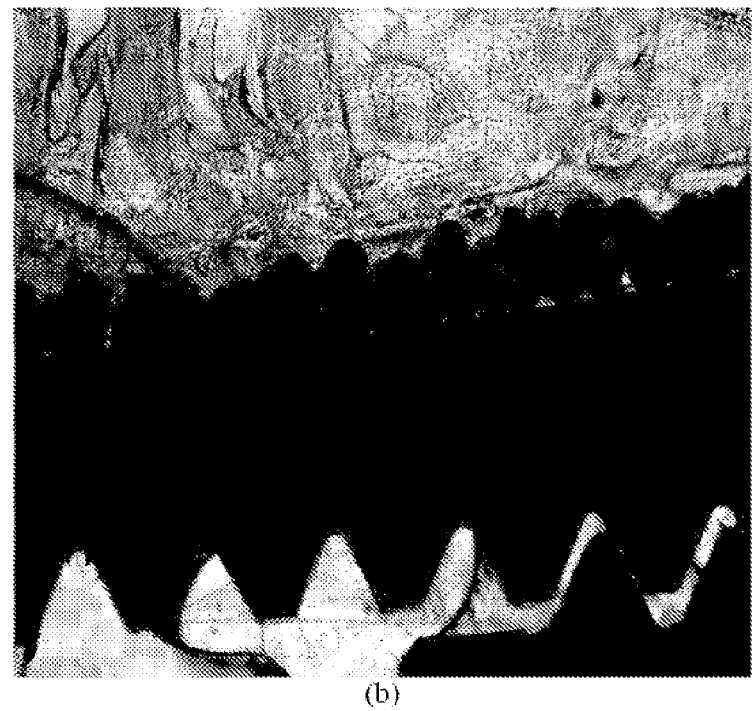
Figure 41:
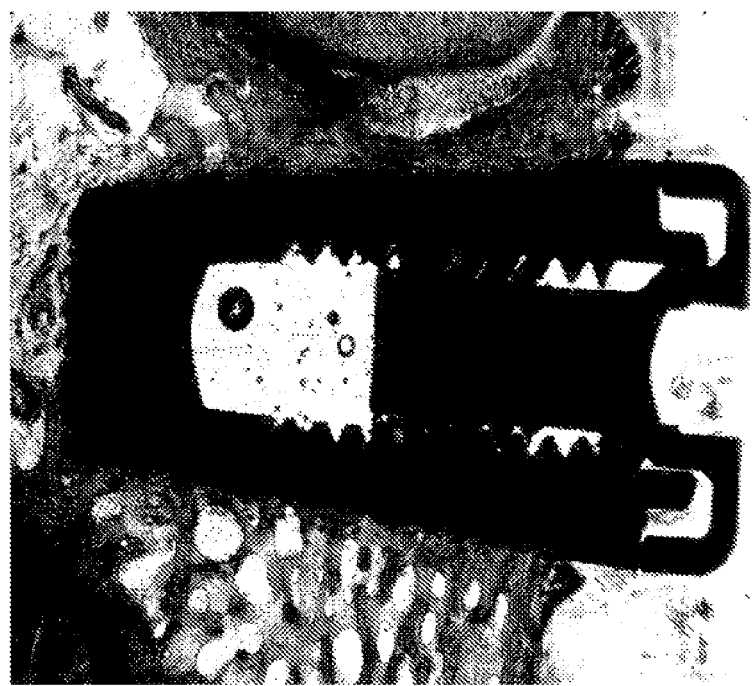
FIGS. 41 (*a*) and (*b*) show the 16-day sintered porous-coated Ti6Al4V implant with 'High' S-CP over-layer—(a) & (b) Sample 8D Right—Good bone ingrowth along implant length.
Figure 41:
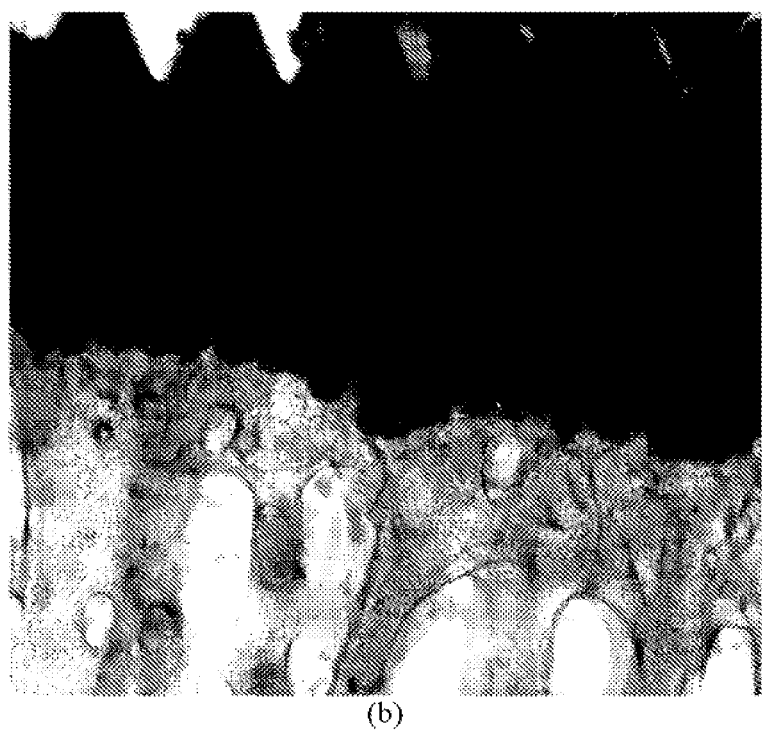

Results: The surface morphology is shown in FIGS. 23, 24, and 25. The surface composition was analyzed using EDXA and the result was shown in Table 12.

TABLE 12

EDXA result of the top PLGA coating

| Element | Wt % |
|---|---|
| CK | 63.76 |
| OK | 26.16 |
| PK | 3.53 |
| AgL | 1.54 |
| CaK | 5.01 |

Example 5

Release profiles

The release of Ag, Ca, and Bupivacaine from the prepared coating was confirmed by ICP analysis and UV spectrometry, respectively.

The coated samples were immersed in 3 mL PBS for 24 and 48 hours at 37° C. At each time point, the release of bupivacaine was measured spectrophotometrically (Nanodrop, Thermo) at 265 nm. The Bupivacaine standard was prepared by dissolving appropriate amounts of the drug in PBS. PBS was used as blank. The Bupivacaine concentration is shown in Table 13.

TABLE 13

The Bupivacaine concentration in PBS at 24 and 48 hours

|  | Bupivacaine Concentration (ppm) |
| --- | --- |
| 24 Hours | 126 |
| 48 Hours | 141 |

The Ag, Ca, and P concentration in PBS at 24 and 48 hours were shown in Table 14.

TABLE 14

The silver and calcium concentration (ppm) in PBS at 24 and 48 hours

|  | Ag | Ca |
| --- | --- | --- |
| 24 Hours | 0.393 | 1.58 |
| 48 Hours | 0.392 | 1.35 |

The degradation study confirmed the coating was able to release Bupivacaine for analgesic effect, Ag ions for anti-microbial effect, and Ca for osteoconductive effect.

Example 6

Example of Method of Synthesis and Characterization

Synthesis
1). VPS gradient coating: Ti6Al4V substrate+pure VPS HA layer+3% VPS AgHA layer
2). Dissolve PLGA (85:15) pellets in dichloromethane and stir overnight
3). Soak and stir β-TCP in silver nitrate solution for 2 hours to allow ion-exchange reaction
4). Add Bupivacaine into the above TCP+silver nitrate solution
5). Dry the Bupivacaine+TCP+silver nitrate solution overnight
6). Add the dry powder of Bupivacaine+TCP+silver nitrate to the dissolved PLGA solution and stir overnight
7). Dip coat the VPS gradient coating using the above PLGA solution with Bupivacaine+TCP+silver nitrate
Characterization
1). SEM top view and cross section
2). EDAX—elemental composition of top layer and cross section (Ca, P, Ag)
3). XRD-Phase composition of the top layer (mainly to detect bupivacaine)
4). Alternative to XRD: dissolution of top layer in PBS (3 days) and subsequent spectroscopic analysis of bupivacaine

Example 7

Further Example of Method of Synthesis and Characterization

Synthesis
1). Sol-gel dip coating process to make a Ag graded coating, i.e. Ti6Al4V substrate+pure Ca—P layer+2% Ag—Ca—P layer
2). Dissolve PLGA (85:15) pellets in Chloroform
3). Add analgesic (e.g. over counter Tylenol) and Ag—CaP (2 wt % Ag) powders into the PLGA
4). Dip coat the sol-gel Ag—Ca—P sample using the prepared PLGA polymer solution.
Characterization
1). SEM top view before and after degradation in PBS and SBF
2). ToF-SIMS to obtain depth information
3). XRD-Phase composition
4). In vitro bioactivity evaluation in SBF (3 days)
5). Dissolution in PBS (24 h, 48 h, 72 h) to measure Ag concentration.

Example 8

Osseointegration of Porous-Surfaced Implants with Modified Anti-Microbial Calcium Phosphate Coatings The results of mechanical pull-out testing of Ti6Al4V alloy porous-surfaced implants prepared with or without sol-gel-formed Ag-modified calcium phosphate thin film overlayers (approximately 1 micron thick) are reported herein. Briefly summarizing, the study used 4 groups of 10 rabbits that had porous-surfaced implants (Endopore® dental implants acquired from Innova-Sybron Dental Products) implanted transversely in their medial femoral condyles, (porous region interfacing with cancellous bone). Implant positioning and implantation procedures were similar to those described in Tache et al (2004), Int J Oral Maxillofac Implants, 19:19-29; Gan et al (2004), Part II: Short-term in vivo studies, Biomaterials. 25:5313-5321; Simmons et al (1999), J Biomed Mater Res., 47: 127-138, all of which are herein incorporated by reference. 'Test' implants (one per animal in either the right or left leg—random placement) were prepared with Ag-modified calcium phosphate coatings overlaying the sintered porous surface of the Ti alloy implants. The porous surface region consisted of approximately three layers of Ti6Al4V alloy powders (44 to 150 micron particle size) sintered so as to form a porous layer approximately 300 micron thick with 35 volume percent porosity (approximate) and with average pore size in the 75 to 100 microns range. The interconnected open-pored structure was suitable for achieving implant fixation by uninhibited bone ingrowth. It is noteworthy that this particle and pore size is somewhat smaller than that conventionally used with orthopedic implants but has proved acceptable and, in fact, is preferred for dental implant applications where dimensional constraints arise.

The sol-gel-formed calcium phosphate overlayer had been studied previously (but minus the Ag+ modification) and, in the unmodified form, was observed to promote faster bone ingrowth (i.e. enhanced osseointegration). Based on these earlier studies, Ag-modified calcium phosphate coatings were proposed and developed by Smith & Nephew as antimicrobial and osteoconductive coatings that would both increase bone ingrowth into porous-surfaced implants as well as reduce the possibility of infection at an implant site during the early post-implantation period. This increased infection resistance during the crucial early post-implantation healing period is desirable since microbial ingress resulting in local infection and inflammatory response would inhibit bone ingrowth and potentially result in implant failure. Therefore, reducing the probability of bacterial infections during this early period would be of considerable benefit in improving the reliability of orthopaedic implants designed for fixation through bone ingrowth.

Materials & Methods

Two different Ag+-containing calcium phosphate formulations were investigated. These are designated in this report as 'Low' and 'High' Ag levels. (In the results presented below LC=low Ag+ (0.9 wt %) calcium phosphate and HC=high Ag+ (2.5 wt %) calcium phosphate coatings). The animal study was designed such that the LC implants were placed in femoral condyles of 20 rabbits with 'control' implants (i.e. no calcium phosphate (NC) sol-gel coating) in the other femur while the HC implants were placed similarly against 'control' implants in the remaining 20 rabbits. Ten rabbits from each group were maintained for 9 days following implant placement and then euthanized while another ten rabbits were maintained for 16 days prior to sacrifice. This provided 10 LC implants after 9-day implantation for comparison against 10 NC 9-day implants and a similar number of LC implants for comparison with NC implants at 16 days. Similarly two groups of 10 HC implants were studied after 9- and 16-day implant residence periods and compared with NC implants.

Implant performance in terms of effective bone ingrowth leading to secure implant fixation was assessed by mechanical pull-out testing (as in the previously reported studies as discussed above) as well as histological examination and assessment of some of the implant-tissue samples after animal sacrifice. Additionally, some of the pulled out implants were examined by secondary electron imaging in the scanning electron microscope to characterize the implant-tissue interface region and to identify any bone-like or fibrous tissue features that might be present. The virtue of the mechanical pull-out testing is that this test provides information on the complete interface rather than the selected area that is observed through microscopic examination. All specimens for mechanical testing were stored in saline solution following animal euthanization and dissection of the femoral condyle region and tested within 2 hours of sacrifice.

Eight of the 10 samples per group as described above were mechanically tested with the remaining two specimens being used for histological sample preparation. Pull-out testing involved mounting the bone-implant samples in a custom-made fixture that ensured proper alignment of the implant and applying a pull-out force under displacement control at a rate of 1 mm/min. The tapered shape of the porous-surfaced implant and the careful sample alignment ensured that frictional forces acting at the bone-implant junction that might have contributed to measured pull-out force and interface stiffness were avoided. Maximum pull-out force and maximum tangential slope of the load-displacement curve were used to determine pull-out resistance and the interface zone stiffness.

Two of the 10 samples per group as described above were collected after rabbit sacrifice and fixed in 10% buffered formalin and processed for embedding in methyl methacrylate. The resulting blocks were sectioned using a diamond wafering blade to produce sections approximately 200 micrometers in thickness along the long axis of the implants at their mid-plane. These samples were then mounted on glass slides and carefully ground and polished to provide non-decalcified sections approximately 30 to 40 microns in thickness. The 'thin' sections were stained with a 1:1 mixture of 0.3% Toluidine blue and 2% sodium borate at 50° C. for 15 minutes, and then stained in 0.3% light green in 2% acetic acid at room temperature for 3 minutes. The sections were examined by light microscopy and appearance recorded as described below.

Statistical analyses (Analysis of Variance with implant design as the one variable parameter) of the maximum pull-out force and measured interface zone stiffness values for the calcium phosphate coated 'test' implants versus the non-coated 'control' implants for the different pairs of implants were undertaken. Thus, the 9-day LC implants were compared with the corresponding 9-day NC implants placed in the contralateral rabbit femoral condyle, the 9-day HC implants were compared with the corresponding 9-day NC implants and the 16-day paired implants were compared in the same way. In addition, the 9-day NC implants were compared with the 16-day NC implants and the 9-day HC implants and 16-day HC implants were compared similarly.

Results & Discussion

The mechanical test results from the current study are presented in Table 15

TABLE 15

Summary of Mechanical Pull-out Tests

| Sample Type | Implant Period (days) | Interface Stiffness (N/mm) (Mean ± SD) | Pull-out Force (N) (Mean ± SD) |
| --- | --- | --- | --- |
| Low Ag-CP | 9 | 311 ± 140 | 192 ± 116 † |
| High Ag-CP | 9 | 355 ± 158 | 193 ± 69 # |
| Control-No CP | 9 | 307 ± 99 * | 177 ± 66 ‡ |
| Low Ag-CP | 16 | 355 ± 89 | 402 ± 118 † |
| High Ag-CP | 16 | 432 ± 75 | 413 ± 147 # |
| Control-No CP | 16 | 371 ± 75 * | 469 ± 120 ‡ |

* Significant Difference (p = 0.048)
†, ‡, # Significant Difference between pairs (p < 0.01)

The statistical tests indicated that there were no significant differences for both maximum pull-out force and interface stiffness between the 'test' and 'control' implants for all pairs of samples (significant differences corresponding to $p<0.05$). However, there was a highly significant increase in pull-out force for the 16-day implants compared with the 9-day samples for both the LC and HC implants ($p<0.01$). The interface zone stiffness also showed an increase from 9 days to 16 days and while this increase was significant ($p=0.048$), the difference was not nearly as great as that observed for pull-out resistance. This interesting result suggests that the interface zone develops a stronger resistance to crack propagation and fracture as more extensive tissue and bone ingrowth develops (i.e. a 'tougher' interface zone develops) from 9 to 16 days. The increase from the 9- to 16-day implantation period is consistent with previously reported results with this rabbit femoral condyle implantation model.

Interestingly, the Ag+-modified calcium phosphate overlayer resulted in interface stiffness values after the 16-day implantation period that, while higher on average than the values for the 9-day implants, were not significantly different. The resistance to implant removal by 9 days for both the as-sintered, non-calcium phosphate-coated and the Ag+-modified calcium phosphate coating (Low and High Ag+) indicated that tissue (bone) ingrowth had occurred for the coated implants.

SEM Examination of Pulled Out Implants

Some of the 9-day implants that had been mechanically tested were examined by secondary electron emission scanning microscopy.

FIGS. 26 through 29 show eight of the collected images. FIGS. 26a&b show images of a calcium phosphate-coated, lower Ag+ implant (CL-9) extracted from the 9-day implanted rabbit #1 A. While this implant exhibited lower interface stiffness and pull-out force, the secondary electron images nevertheless show extensive tissue attachment and ingrowth with areas displaying the characteristics of mineralized tissue. FIGS. 27a&b are images of the noncoated 'control' implant (NCL-9) extracted from the other knee of the same animal. This implant displayed higher stiffness and pull-out values compared to the coated implant (CL) from the contralateral limb and showed the expected extensive tissue attachment and mineralized tissue ingrowth by the 9-day implant period. FIGS. 28a&b and 29a&b are images of the extracted higher Ag+-containing calcium phosphate coated implant (FIGS. 28a&b) and the corresponding non-coated 'control' implant (FIGS. 29a&b); (Rabbit #1B i.e. containing implants CH-9 and NCH-9 respectively).

BS-SEM Examination of Non-mechanical Testing Implants

BS-SEM was used to collect images of the tissue-implant interface zone with quantitative image analyses being performed on the examined sections. For the quantitative assessment (Quantimet Image Analysis program), an envelope approximately 220 micrometers wide from the implant substrate along the length of its porous-coated region was selected (i.e. an envelope width that approached the extremity of the porous coat along the implant length but excluded more peripheral regions; the implant ends were also excluded). This region was analyzed using the Quantimet image analysis software. The percent area of bone within the pores was determined (i.e. % [bone area/pore area]). The program also allowed a determination of the percent porosity of the porous coat that was nominally designed to be 35 to 40 volume percent.

FIGS. 30 to 35 show typical BS-SEM images for all sample types. The BS-SEM images clearly show mineralized tissue (bone) ingrowth (light grey regions) at the two time periods for implants with CP over-layers as well as 'control' implants. The results of the quantitative image analysis for percent bone within available porosity are presented in Table 16. For the sections analyzed, the implant length was divided into four sections for analysis thereby allowing higher magnification images for the analysis. The four measurements were then averaged to give a percent bone ingrowth (and percent porosity) for each implant. The data from all the sections is included in Table 16 and indicates the variation that was observed along the implant length. This is not surprising in view of the structure of the cancellous bone into which the implants were placed. For each implant, a mean and standard deviation was determined. A one-way ANOVA was undertaken to determine if there were statistical differences between implants in the contralateral limbs for each rabbit. Statistical significance was considered at $p<0.05$. The different regions (bone, Ti alloy particles and unfilled pores, or at least not filled with bone) were readily distinguished by the Quantimet imaging software allowing an objective determination of the percent bone fill within the available pores. Only intra-animal comparisons were made (i.e. left and right legs within each animal). This provided seven sets for comparison including all the different conditions (Low S-CP, High S-CP, control at 9 days and 16 days) with two animals assessed for each condition with one exception. Unfortunately, the one lost implant (Rabbit 2C) could not be included.

TABLE 16

Summary of quantitative image analysis of BS-SEM examination

| | 9-day implants | | | | | | | |
|---|---|---|---|---|---|---|---|---|
| % bone/pores | 4AL-9dc | 4AR-9dl | 8AR-9dc | 9AL-9dl | 5BR-9dc | 5BL-9dh | 8BR-9dc | 8BL-9dh |
| | 33.47 | 13.03 | 14.60 | 17.30 | 22.81 | 16.42 | 9.42 | 12.77 |
| | 18.45 | 12.02 | 8.76 | 27.09 | 27.50 | 35.50 | 7.24 | 15.10 |
| | 32.30 | 23.57 | 9.46 | 16.37 | 30.66 | 35.13 | 8.18 | 23.57 |
| | 27.05 | 30.56 | 13.76 | 26.87 | 36.42 | 38.41 | 10.20 | 25.18 |
| mean | 27.97 | 20.02 | 11.63 | 21.93 | 29.37 | 31.37 | 8.76 | 19.15 |
| SD | 6.82 | 8.66 | 2.91 | 5.85 | 5.70 | 10.07 | 1.31 | 6.13 |
| ANOVA-p | 0.20 | | 0.02 | | 0.74 | | 0.02 | |

| | 16-day implants | | | | | | |
|---|---|---|---|---|---|---|---|
| | 9CL-16dc | 9CR-16dl | 2CL-16dc | 1DL-16dc | 1DR-16dh | 8DL-16dc | 8DR-16dh |
| | 44.44 | 26.61 | 39.34 | 41.53 | 26.25 | 34.67 | 48.21 |
| | 53.18 | 48.12 | 40.77 | 31.68 | 33.39 | 52.00 | 53.03 |
| | 42.44 | 50.70 | 50.63 | 42.12 | 38.59 | 42.00 | 53.06 |
| | 30.45 | 29.50 | 53.47 | 44.40 | 43.15 | 46.51 | 55.14 |
| mean | 42.63 | 38.75 | 47.63 | 39.96 | 36.35 | 43.82 | 52.36 |
| SD | 9.36 | 12.42 | 6.11 | 6.88 | 7.26 | 7.36 | 2.94 |
| ANOVA-p | 0.64 | | | 0.36 | | 0.075 | |

Despite the small number of samples analyzed, the quantitative image analysis does suggest some interesting additional findings.

The 9-day data indicates that in two rabbits (8A and 8B), % bone ingrowth was significantly higher for the S-CP-modified implants (8A, low S-CP and 8B high S-CP) compared to their respective 'control' implants (no CP over-layer). The other two 9-day rabbits that were analyzed did not show significant differences.

There were no significant differences in bone ingrowth between the CP-modified and 'control' implants at 16 days.

As before, these findings indicate that the S-CP-over-layers do not inhibit bone ingrowth. In fact, the BS-SEM images and the quantitative image analysis suggest that the addition of the S-CP over-layer may promote faster rates of bone ingrowth.

Quantitative image analysis was also used to confirm the percent porosity of the implants. The percent porosity as determined using the Quantimet software for the 17 sections analyzed was equal to 43.1±2.7%.

Histological Assessment of Rabbit Implants

The sections examined were prepared from 16 tissue-implant blocks harvested from 8 rabbits selected from the 40 rabbits and used in the study. Of these 16 samples for histology section preparation, the implant was not present in one block. That implant (sample 2C, 16-day 'Low' Ag+), presumably, had not osseointegrated but had migrated from the implant site after placement. The remaining 64 implants were mechanically tested (pull-out tests) to determine the shear strength and interface stiffness of the implant-bone interface zone as discussed above.

There was no obvious difference between implants that have been treated either high or low and controls (non-treated). Maturation of bone ingrowth over time was the same in all animals. No reaction was observed to implants that have been treated and no obvious cell death in surrounding bone. FIGS. 36 to 41 show representative micrographs of each condition indicating regions of bone ingrowth for all implants. This finding is consistent with the mechanical pull-out test results reported above.

Summary & Conclusions

1. The pull-out test results and the SEM images of the pulled out implants confirm that tissue ingrowth resulting in secure implant fixation occurs by 9 days for porous-surfaced implants with an overlayer of Ag+-modified calcium phosphate sol-gel-formed coatings.

2. The pull-out tests suggest that the modified coatings with the lower or higher Ag+-additions perform similarly.

3. As expected, the pull-out force for implant removal increased with increasing implantation period with significantly higher pull-out forces being recorded for the 16-day implanted samples compared with the 9-day samples. However, the interface zone stiffness values were not significantly different for the 9- and 16-day implanted samples although the mean values were higher for the 16-day implants.

4. While the recorded pull-out forces for the modified calcium phosphate-coated implants from the present study were not significantly different from those reported in a previous study (Tache et al), significantly higher interface zone stiffness values were observed. The higher interface stiffness may have been due to the longer implants used in the previous study (9 mm versus 7 mm length).

5. The addition of Ag+ to a sol-gel calcium phosphate film deposited over a porous-coated Ti-6Al-4V implant does not inhibit bone ingrowth. The two concentrations of silver that were tested appeared to give similar results.

Example 9

Antimicrobial Activity of HA-Ag Coatings

Method

The coatings from Example 2 were evaluated for antimicrobial activity. In addition, a negative control (uncoated Ti6Al4V substrate) and a positive control (Acticoat 7 (Smith and Nephew)—a nanocrystalline silver containing wound dressing known to have antimicrobial properties) were also evaluated.

Sample Culture Method

A suspension of the test organism containing approximately $10^4$ cfu/ml was prepared, by harvesting an overnight slope culture. The test coupons were tested on a method based on ASTM standard E2149-01 (Standard Test Method for Determining the Antimicrobial Activity of Immobilized Antimicrobial Agents Under Dynamic Contact Conditions).

Samples were placed into a 24 well sterile tissue culture plate flat bottom with low evaporation lid, four of each sample type were prepared for each time point tested. In addition a positive control sample of Acticoat 7 and negative culture control were set up (3 replicates each per time point). Each sample was inoculated with 2 ml of test organism suspension and plates were sealed with parafilm to minimise culture evaporation. The samples were incubated at 37° C. with agitation at 150 rpm for the relevant time period, sonicated counts were taken at 24, 48 and 72 hours. Sonicated counts were not suitable for the positive and negative method control samples. Time 0 samples were not taken for sonicated counts as without time for colonisation to occur they would not have yielded any relevant information.

For additional supporting information, showing any activity displayed away from the surface, counts were taken from the test inoculum at 0, 24, 48 and 72 hours to calculate the log reduction in count in the suspension. 3 replicates were sampled at all time points as this was all time constraints would allow.

Sonicated Counts

Sonication in a detergent solution is a recognised method of removing attached cells from metal surfaces to assess their numbers. Here it was used to determine if different levels of bacterial growth were seen on samples with silver-containing HA coating and non silver-containing HA controls.

Coupons were washed in PBS then the excess was aspirated off, this process was repeated 5 further times to give 6 washes in all. The coupons were placed in 9 ml of STS (0.85% salt & 1% Tween 20 & 0.4% sodium thioglycolate) in 15 ml Falcon tubes and floated in a sonicating water bath using a polystyrene float. Samples were then sonicated for 10 minutes at 60 Hz.

The resulting sonicate was diluted down to $10^{-5}$ in Maximum Recovery Diluent (MRD) and all dilutions were plated out on duplicate Aerobic Count Petrifilm (3M). Resulting films were then incubated for at least 48 hours at 32° C. before enumeration using the petrifilm reader.

Sonicated Counts Results

Figure 42:
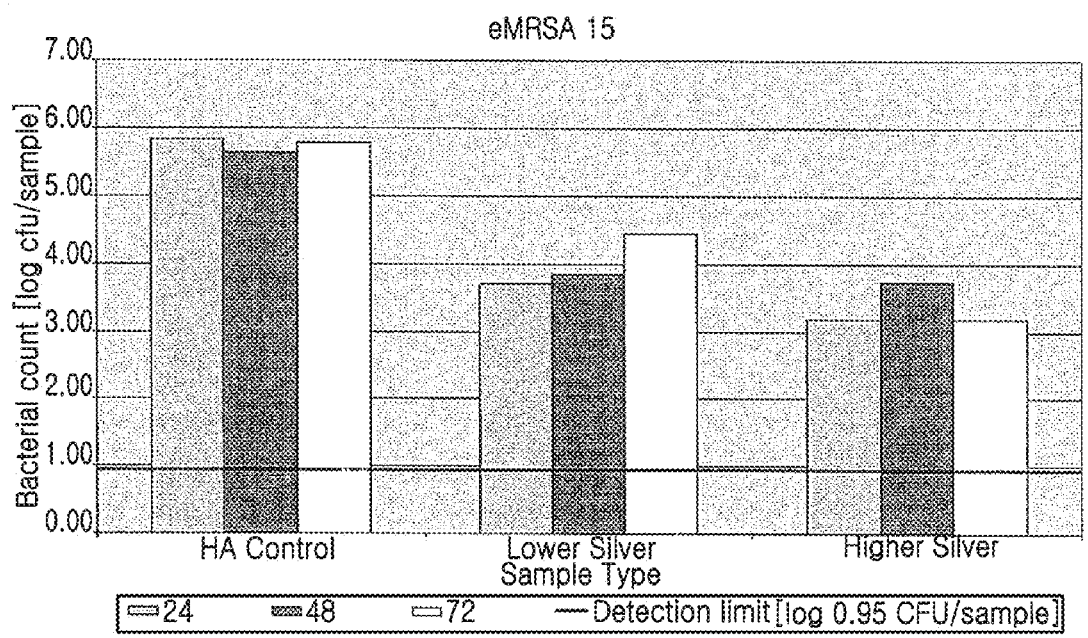
FIGS. 42 and 43 show results of sonicated counts for microbiological activity.
Figure 43:
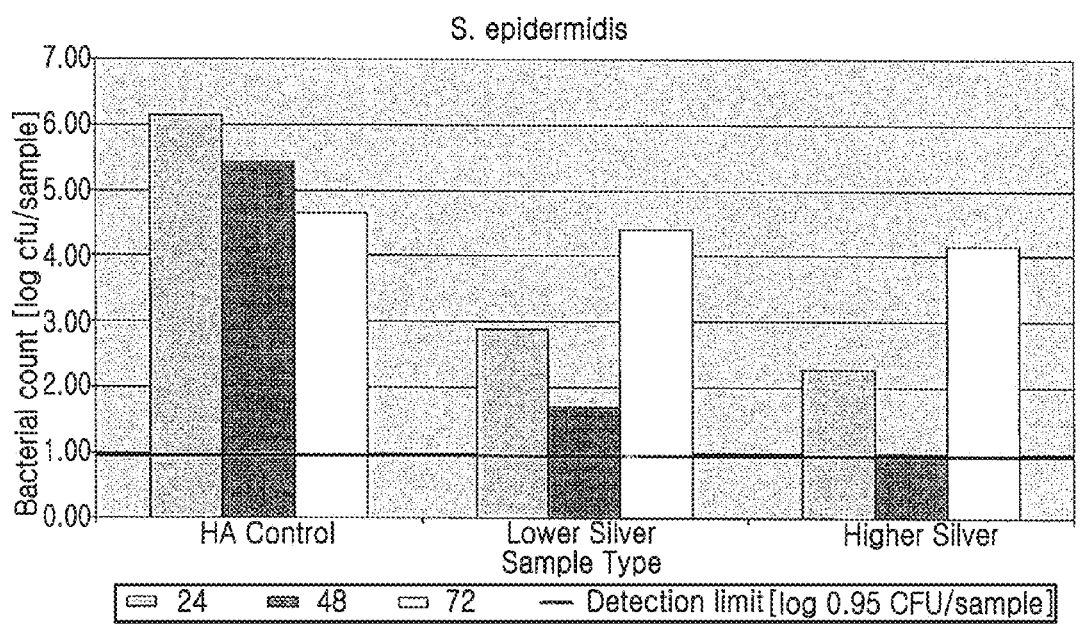

FIGS. 42 and 43 show the results of the sonicated counts. A larger reduction in surface count was seen against *S. epidermidis* than eMRSA 15 (epidemic MRSA 15, a UK hospital isolate) though grow back was seen at the 72 hour timepoint to levels equivalent to the initial inoculation and the equivalent control.

Counts from Suspension

After the appropriate time period 1 ml of the inoculum was sampled from reps 1 to 3 (of all samples and added to 9 ml of STS). 1 ml of this was then plated in duplicate and 1ml was serially diluted, to $10^{-4}$ at time 0, $10^{-5}$ at 24 hours and $10^{-6}$ thereafter for negative controls, and $10^{-5}$ at all time points for coated samples and positive controls, in MRD.

For uncoated samples and culture controls at 0 and 24 hours dilutions from $10^{-2}$ downwards and $10^{-3}$ downwards respectively were plated out on duplicate Aerobic Count Petrifilm (3M). For coated samples all dilutions were plated in duplicate on Aerobic Count Petrifilm (3M). The resulting plates were incubated at 32° C. or at least 48 hours before counting.

Suspension Counts Results

Figure 44:
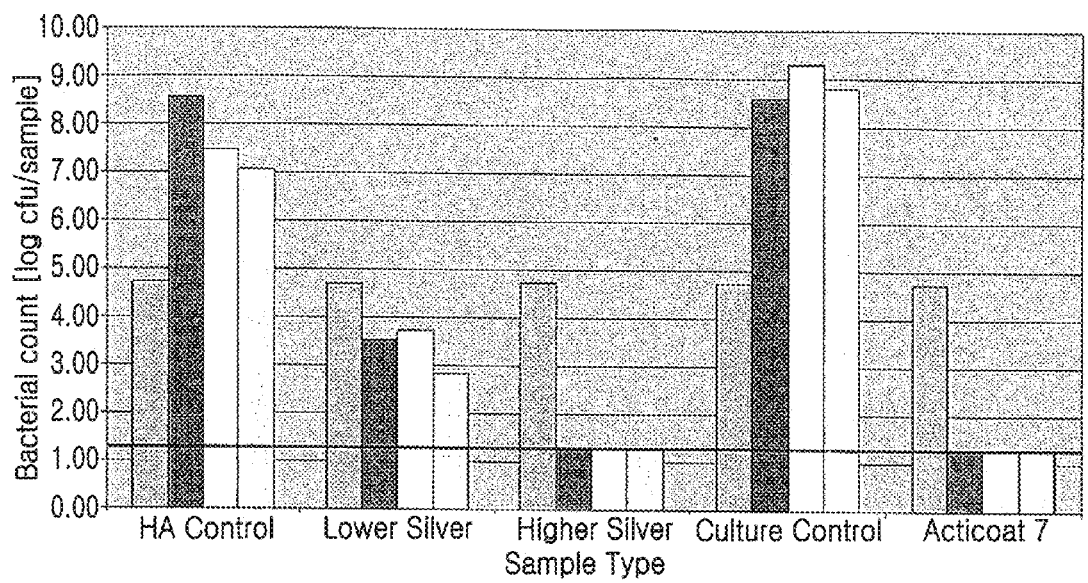
FIGS. 44 and 45 show results of suspension counts for microbiological activity.
Figure 45:
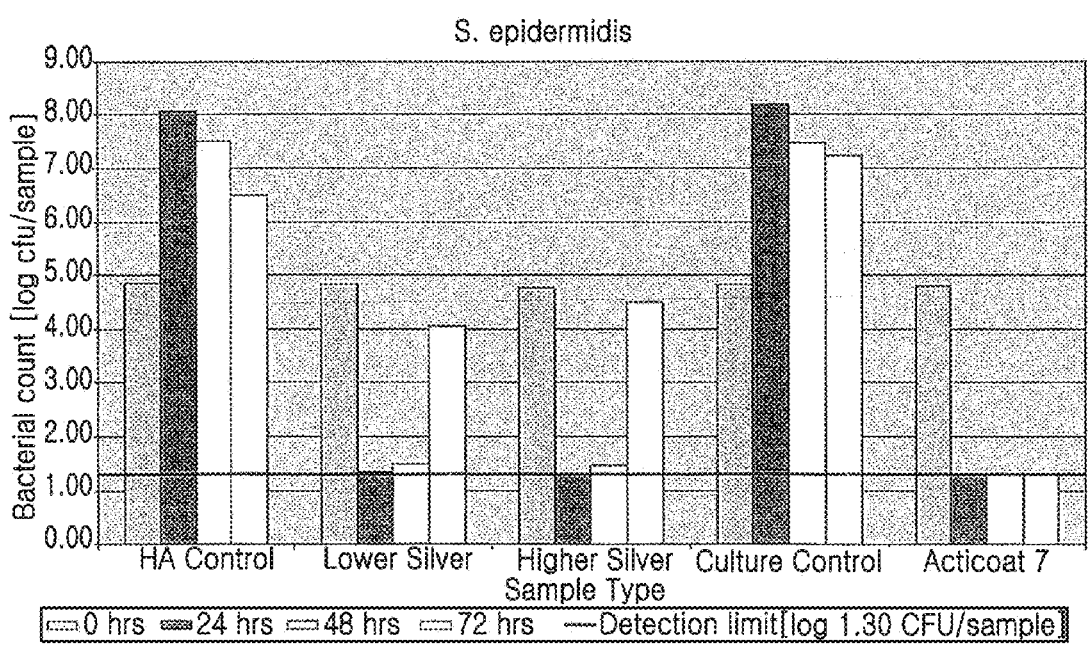

FIGS. 44 and 45 show the results of the suspension counts. Counts from the suspension can be used to calculate a reduction in count from time 0 and therefore a log reduction. Against eMRSA 15 the lower dose silver showed little kill but did keep numbers in suspension static. The higher silver dose killed to the limit of detection and maintained numbers there. Both doses of silver HA initially killed *S. epidermidis* down to a low level but there was grow back of the organism to levels comparable with the initial organism at 72 hours.

Example 10

Cytotoxicity Testing of VPS Ag/HA Samples

The coatings from Example 2 were evaluated for cytotoxicity. In addition, uncoated Ti6Al4V coupons (negative control known to be non-cytotoxic) were also evaluated.
Method
Materials
Uncoated Ti6Al4V coupons
VPS-Hydroxyapatite (HA) coupons—Batch TO035A
VPS-HA with low dose silver (1%) (HA1)—Batch TO035B
VPS-HA with medium dose silver (2%) (HA2)—Batch TO035C
Polyvinyl chloride discs—Batch TO024-90-02-01
High Density Polyethylene discs—Batch TO024-90-02-02
Alpha—Minimum Essential Medium Eagles (alpha-MEM) plus 10% foetal calf serum—#9696, #9662, #9707
Trypsin-EDTA—Lot 058K2373
Trypan Blue—Sigma T8154 Lot 088k2379 and Lot 047k2349
Vectashield mounting medium for fluorescence with DAPI—Vector H—1200 Lot UO403
WST-1 reagent—Roche 11644807001 Lot 14473200
Preparation of Conditioned Media Using ISO10993 guidelines the surface area to volume ratio was calculated for all the test and control samples to determine the volume of media required per sample to produce liquid extracts of the samples (referred to as conditioned media). For the HA, HA1, HA2 and titanium coupons the volume of media required was 1.23 ml/coupon, four coupons were placed in a well of a 6-well plate (n=4) in a total volume of 4.92 ml. The volume of media required for the PVC and HDPE discs was 1.33 ml/disc, four discs were placed in a well of a 6-well plate (n=4) in a total volume of 5.32 ml. The layout of these groups in the 6-well plates was randomised to help reduce the effect of plate layout. Alongside these plates a 6-well plate had 5.32 ml/well of media added, acting as the tissue culture plastic group (TCP) as this group is only used as an assay control and therefore did not need to be included in the randomisation. The media incubated with the test materials was alpha-MEM; these five plates were incubated at 37° C., 5% CO2 for 7 days.

Cell Seeding

MC3T3-E1 cells were passaged for counting according to SOP/CB/006. The cells were required for seeding at $5\times10^4$/ $cm^2$. 168 wells were seeded over 2×96-well plates at this density, the cells were now P13. Cells were cultured for 48 hours at 37° C., 5% CO2.

Application of Conditioned Media

The media was removed from the 96-well plates and replaced with 100 μl of the appropriate conditioned media, n=6 per sample group per treatment/control group. The 2×96-well plates were incubated for 24-hours at 37° C., 5% CO2.

WST-1 Assay

Figure 46:
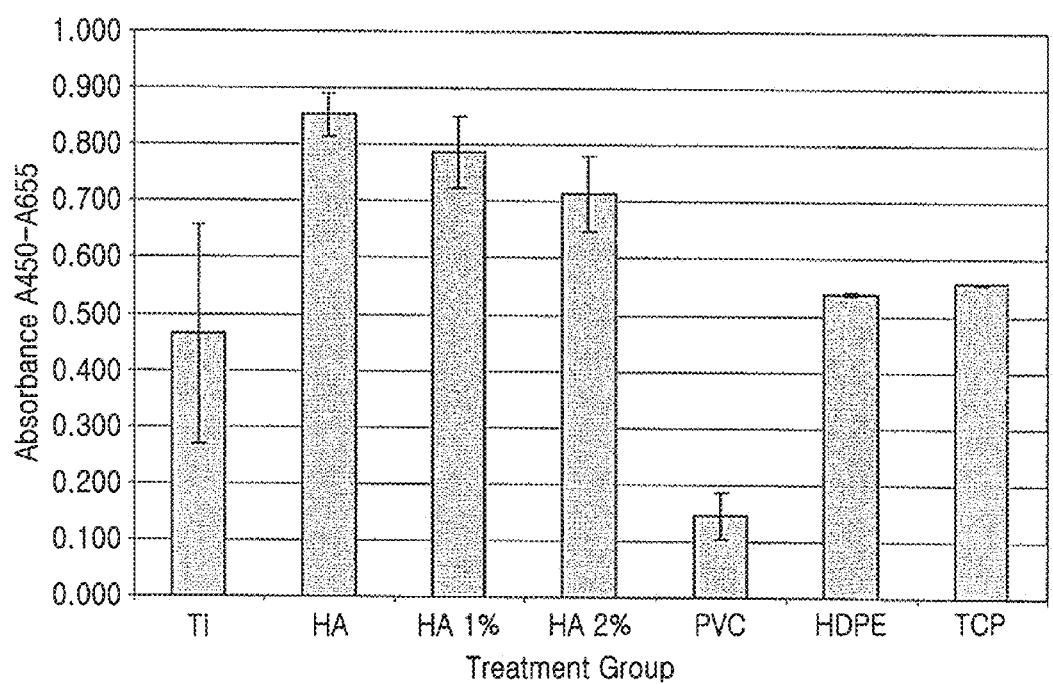
FIG. 46 shows the mean absorbance at A450 nm-A655 nm of MC3T3 cells cultured in Ag/HA cultured media. Error bars represent the standard deviations of the data.

WST-1 reagent is used to quantify the metabolic activity of the cells exposed to the conditioned media. 10 μl/well of WST-1 reagent was added to each of the 96-well plates. The plates were incubated for 1 hour at 37° C., 5% CO2 shaken for 1 minute and then read on the Multiskan plate reader (asset no. 00005247) at 450 nm and 650 nm for the test and reference wavelengths respectively. The reference wavelength was subtracted from the test wavelength for each well and the means for each group calculated and plotted to demonstrate the metabolic activity of the cells (see FIG. 46).

Results and Discussion
Mycoplasma Testing

Mycoplasma testing by DAPI staining was conducted according to SOP/CB/069. The cells used in this experiment were deemed mycoplasma negative.

WST-1 Assay

The HA1 and HA2 groups stimulated increased metabolic activity of MC3T3-E1 cells in this experiment compared to the positive cytotoxic control group PVC, and the negative control group HDPE. The metabolic activity of cells exposed to HA alone was however higher than either of the two Ag containing groups. The metabolic activity of cells exposed to the Ti6Al4V group was below that of all HA containing groups and the negative control HDPE. Ti6Al4V did however stimulate the mineralisation of cells to a level that was twice that of the positive control. The TCP group was used as cell control group and cells in this group metabolised at a similar level to the negative control HDPE. It was noted that the metabolic activity of cells in the titanium group was below that of the two negative controls however there was a large spread of data from this data set as shown by the error bars.

CONCLUSIONS

VPS Ag/HA samples at 1 and 2% silver increased the metabolic activity of MC3T3-E1 cells to levels above that of the positive and negative controls. However, the metabolic activity of cells from these groups was lower than cells in the HA alone group.

The skilled person will realize that the breadth and scope of the present invention should not be limited by any of the above-described exemplary embodiments but should be defined only in accordance with any claims appended hereto and their equivalents.

The invention claimed is:

1. A medical implant comprising an implant surface having a surface coating comprising a silver-substituted osseointegration agent and an antimicrobial metal agent, wherein the silver-substituted osseointegration agent has a silver concentration that exhibits homogeneity throughout a thickness of the surface coating, and wherein the antimicrobial metal agent is present in at least a part of the coating as discrete particles and are one or more of metallic silver, metallic copper and metallic zinc, the discrete particles exhibiting release kinetic characteristics that release the antimicrobial metal agent into a host tissue as metallic ions, metallic particles or metallic compounds, wherein the release of the antimicrobial metal agent into the host tissue is in the form of a burst release, a sustained release or a combined burst and sustained release and is at a concentration sufficient to have an anti-bacterial effect on the host tissue.

2. The medical implant of claim 1, wherein the antimicrobial metal agent in the surface coating is present at about 0.1 to about 10 weight percent.

3. The medical implant of claim 1, wherein the discrete particles are discrete metallic silver particles.

4. The medical implant of claim 3, wherein the metallic silver particles are spherical or irregular in shape.

5. The medical implant of claim 4, wherein the diameter of the metallic silver particles is about 15 nm to about 10 μm.

6. The medical implant of claim 1, wherein the silver-substituted osseointegration agent includes about 0.1 to about 10% by weight of silver.

7. The medical implant of claim 1, wherein the silver-substituted osseointegration agent includes about 0.5 to about 3.0% by weight of silver.

8. The medical implant of claim 1, wherein the osseointegration agent comprises hydroxyapatite, β-tricalcium phosphate, or a mixture of both.

9. The medical implant of claim 1, wherein the thickness of the surface coating is about 1 μm.

10. The medical implant of claim 1, wherein the thickness of the surface coating is about 10 μm to about 200 μm.

11. The medical implant of claim 1, wherein the thickness of the surface coating is about 30 μm to about 100 μm.

12. The medical implant of claim 1, wherein the tensile attachment strength of the surface coating to the implant surface is equal to or greater than about 15 MPa.

13. The medical implant of claim 1, wherein the surface coating further has osteoinductive, or osteopromotive properties.

14. The medical implant of claim 1, wherein the osseointegration agent further includes at least one of the following, carbonate, fluoride, silicon, magnesium, strontium, vanadium, lithium, copper, or zinc.

15. A medical implant comprising an implant surface having a surface coating, the surface coating having a thickness greater than about 1 μm and comprising a calcium derived osseointegration agent and an antimicrobial metal agent;
wherein the osseointegration agent comprises from about 0.1 to about 10% by weight of silver, and the antimicrobial metal agent is discrete metallic silver particles having a diameter of from about 15 nm to about 10 μm, the silver particles being distributed throughout the thickness of the surface coating and exhibiting release kinetic characteristics that release the antimicrobial metal agent into a host tissue as metallic ions, metallic particles or metallic compounds;
wherein the osseointegration agent has a silver concentration that exhibits homogeneity throughout the thickness of the surface coating; and
wherein the release of the antimicrobial metal agent into the host tissue is in the form of a burst release, a sustained release, or a combined burst and sustained release, and is at a concentration sufficient to have an anti-bacterial effect on the host tissue.

16. The medical implant of claim 15, wherein the osseointegration agent comprises hydroxyapatite, β-tricalcium phosphate, or a mixture of both.

17. The medical implant of claim 15, wherein the thickness of the surface coating is about 10 μm to about 200 μm.

18. The medical implant of claim 15, wherein the osseointegration agent further includes at least one of the following, carbonate, fluoride, silicon, magnesium, strontium, vanadium, lithium, copper, or zinc.

19. A medical implant comprising an implant surface having a plasma sprayed surface coating, the surface coating comprising an antimicrobial metal agent and a silver-substituted osseointegration agent, the osseointegration agent having a homogenously distributed silver concentration of from about 0.5% to about 3.0% by weight throughout the surface coating;
wherein the surface coating has a thickness of from about 30 μm to about 100 μm and exhibits a tensile attachment strength to the implant surface of 15 MPa or greater; and
wherein the antimicrobial metal agent is discrete metallic silver particles having a diameter of from about 15 nm to about 10 μm, the silver particles being distributed throughout the thickness of the surface coating and exhibiting release kinetic characteristics that release the antimicrobial metal agent into a host tissue as metallic ions, metallic particles or metallic compounds.

* * * * *